United States Patent
Abrams et al.

(10) Patent No.: US 9,643,180 B2
(45) Date of Patent: May 9, 2017

(54) METHOD FOR DETECTING ANALYTES

(75) Inventors: Ezra Abrams, Newton, MA (US);
Sadanand Gite, Arlington, MA (US);
Lisa Shinefeld, Lexington, MA (US);
Don Straus, Cambridge, MA (US);
Gordon Siek, Somerville, MA (US);
Greg Yantz, Somerville, MA (US)

(73) Assignee: First Light Biosciences, Inc., Bedford, MA (US)

( * ) Notice: Subject to any disclaimer, the term of this patent is extended or adjusted under 35 U.S.C. 154(b) by 0 days.

(21) Appl. No.: 13/120,516

(22) PCT Filed: Sep. 24, 2009

(86) PCT No.: PCT/US2009/058270
§ 371 (c)(1),
(2), (4) Date: Feb. 22, 2012

(87) PCT Pub. No.: WO2010/036827
PCT Pub. Date: Apr. 1, 2010

(65) Prior Publication Data
US 2012/0149007 A1    Jun. 14, 2012

Related U.S. Application Data

(60) Provisional application No. 61/099,830, filed on Sep. 24, 2008.

(51) Int. Cl.
| | |
|---|---|
| *G01N 21/64* | (2006.01) |
| *B01L 3/00* | (2006.01) |
| *A61B 5/157* | (2006.01) |
| *G01N 21/03* | (2006.01) |
| *G01N 21/25* | (2006.01) |
| *G01N 33/543* | (2006.01) |
| *A61B 5/15* | (2006.01) |
| *A61B 5/117* | (2016.01) |
| *A61B 5/151* | (2006.01) |

(Continued)

(52) U.S. Cl.
CPC ........ *B01L 3/502715* (2013.01); *A61B 5/157* (2013.01); *A61B 5/150022* (2013.01); *A61B 5/15113* (2013.01); *A61B 5/15186* (2013.01); *A61B 5/150213* (2013.01); *A61B 5/150221* (2013.01); *A61B 5/150274* (2013.01); *A61B 5/150305* (2013.01); *A61B 5/150343* (2013.01); *A61B 5/150351* (2013.01); *A61B 5/150412* (2013.01); *A61B 5/150503* (2013.01); *A61B 5/150786* (2013.01); *B01L 3/5029* (2013.01); *B01L 3/5082* (2013.01); *B01L 3/502761* (2013.01); *G01N 21/03* (2013.01); *G01N 21/253* (2013.01); *G01N 21/6452* (2013.01); *G01N 21/6458* (2013.01); *G01N 33/54373* (2013.01); *A61B 5/117* (2013.01); *A61B 5/151* (2013.01); *B01L 7/00* (2013.01); *B01L 9/52* (2013.01); *B01L 2200/025* (2013.01); *B01L 2200/026* (2013.01); *B01L 2200/027* (2013.01); *B01L 2200/0605* (2013.01); *B01L 2200/10* (2013.01); *B01L 2300/022* (2013.01); *B01L 2300/042* (2013.01); *B01L 2300/043* (2013.01); *B01L 2300/046* (2013.01); *B01L 2300/048* (2013.01); *B01L 2300/0654* (2013.01); *B01L 2300/0681* (2013.01); *B01L 2300/0864* (2013.01); *B01L 2400/043* (2013.01); *B01L 2400/0406* (2013.01); *B01L 2400/0409* (2013.01); *B01L 2400/0415* (2013.01); *B01L 2400/0457* (2013.01); *B01L 2400/0472* (2013.01); *B01L 2400/0481* (2013.01); *B01L 2400/0677* (2013.01); *B01L 2400/0683* (2013.01); *G01N 21/6428* (2013.01); *G01N 2021/0325* (2013.01); *G01N 2021/0346* (2013.01)

(58) Field of Classification Search
None
See application file for complete search history.

(56) References Cited

U.S. PATENT DOCUMENTS

| | | |
|---|---|---|
| 2,672,431 A | 3/1954 | Goetz |
| 2,761,813 A | 9/1956 | Goetz |
| 3,694,317 A | 9/1972 | Scher |

(Continued)

FOREIGN PATENT DOCUMENTS

| | | |
|---|---|---|
| AU | 760425 B2 | 3/2000 |
| CN | 101254482 | 9/2008 |

(Continued)

OTHER PUBLICATIONS

Graziani-Bowering et al., Journal of Immunological Methods, 1997, vol. 207, pp. 157-168.*

(Continued)

*Primary Examiner* — Mindy G Brown
(74) *Attorney, Agent, or Firm* — Clark & Elbing LLP

(57) ABSTRACT

The invention provides an improved method for sensitive and specific detection of target molecules, cells, or viruses. The inventive method uses large area imaging to detect individual labeled targets complexed with a target-specific selection moiety. The invention eliminates wash steps through the use of target-specific selection through one or more liquid layers that can contain optical dye and density agents. By eliminating washes the invention simplifies instrumentation engineering and minimizes user steps and costs. The invention uses sensitive image analysis to enumerate individual targets in a large area, is scalable, and can be deployed in systems ranging in complexity from manual to highly automated.

33 Claims, 47 Drawing Sheets

(51) Int. Cl.
  *B01L 7/00* (2006.01)
  *B01L 9/00* (2006.01)

(56) References Cited

U.S. PATENT DOCUMENTS

| | | | |
|---|---|---|---|
| 3,981,776 A | 9/1976 | Saxholm | |
| 4,097,586 A | 6/1978 | Gross | |
| 4,098,876 A | 7/1978 | Piasio et al. | |
| 4,115,535 A | 9/1978 | Giaever | |
| 4,125,375 A | 11/1978 | Hunter | |
| 4,129,419 A | 12/1978 | Hermann, Jr. | |
| 4,141,687 A | 2/1979 | Forrest et al. | |
| 4,157,323 A | 6/1979 | Yen et al. | |
| 4,177,253 A | 12/1979 | Davies et al. | |
| 4,222,744 A | 9/1980 | McConnell | |
| 4,436,826 A | 3/1984 | Wang | |
| 4,438,068 A | 3/1984 | Forrest | |
| 4,454,233 A | 6/1984 | Wang | |
| 4,455,370 A | 6/1984 | Bartelsman et al. | |
| 4,477,578 A | 10/1984 | Miles et al. | |
| 4,537,861 A | 8/1985 | Elings et al. | |
| 4,562,157 A | 12/1985 | Lowe et al. | |
| 4,565,783 A | 1/1986 | Hansen et al. | |
| 4,582,810 A | 4/1986 | Rosenstein | |
| 4,587,213 A | 5/1986 | Malecki | |
| 4,614,585 A | 9/1986 | Mehra et al. | |
| 4,693,972 A | 9/1987 | Mansour et al. | |
| 4,731,337 A | 3/1988 | Luotola et al. | |
| 4,745,077 A | 5/1988 | Holian et al. | |
| 4,777,137 A | 10/1988 | Lemonnier | |
| 4,777,145 A | 10/1988 | Luotola et al. | |
| 4,912,037 A | 3/1990 | Lemonnier | |
| 4,922,092 A | 5/1990 | Rushbrooke et al. | |
| 4,959,301 A | 9/1990 | Weaver et al. | |
| 4,981,783 A | 1/1991 | Augenlicht | |
| 4,988,302 A | 1/1991 | Smith et al. | |
| 4,988,618 A | 1/1991 | Li et al. | |
| 5,073,497 A | 12/1991 | Schwartz | |
| 5,089,413 A | 2/1992 | Nelson et al. | |
| 5,137,812 A | 8/1992 | Matner | |
| 5,190,666 A | 3/1993 | Bisconte | |
| 5,232,838 A | 8/1993 | Nelson et al. | |
| 5,238,810 A | 8/1993 | Fujiwara et al. | |
| 5,258,284 A | 11/1993 | Morris, Jr. et al. | |
| 5,262,526 A | 11/1993 | Sasamoto et al. | |
| 5,292,644 A | 3/1994 | Berg | |
| 5,306,420 A | 4/1994 | Bisconte | |
| 5,321,545 A | 6/1994 | Bisconte | |
| 5,355,215 A | 10/1994 | Schroeder et al. | |
| 5,366,867 A | 11/1994 | Kawakami et al. | |
| 5,464,749 A | 11/1995 | Schwarzberg et al. | |
| 5,474,910 A | 12/1995 | Alfano | |
| 5,510,246 A | 4/1996 | Morgan | |
| 5,538,857 A | 7/1996 | Rosenthal et al. | |
| 5,541,069 A | 7/1996 | Mortensen et al. | |
| 5,552,272 A | 9/1996 | Bogart | |
| 5,558,839 A | 9/1996 | Matte et al. | |
| 5,582,982 A | 12/1996 | Cubbage et al. | |
| 5,585,241 A | 12/1996 | Lindmo | |
| 5,604,351 A | 2/1997 | Bisconte | |
| 5,606,413 A | 2/1997 | Bellus et al. | |
| 5,624,850 A | 4/1997 | Kumar et al. | |
| 5,652,939 A | 7/1997 | Verlinden et al. | |
| 5,653,939 A | 8/1997 | Hollis et al. | |
| 5,663,057 A | 9/1997 | Drocourt et al. | |
| 5,672,880 A | 9/1997 | Kain | |
| 5,681,530 A | 10/1997 | Kuster et al. | |
| 5,681,712 A | 10/1997 | Nelson | |
| 5,694,478 A | 12/1997 | Braier et al. | |
| 5,705,402 A | 1/1998 | Leland et al. | |
| 5,736,405 A | 4/1998 | Alfano et al. | |
| 5,744,322 A | 4/1998 | Krejcarek et al. | |
| 5,766,868 A | 6/1998 | Seto | |
| 5,792,617 A | 8/1998 | Rotman | |
| 5,814,454 A | 9/1998 | Ju | |
| 5,821,066 A | 10/1998 | Pyle et al. | |
| 5,828,716 A | 10/1998 | Bisconte de Saint Julien | |
| 5,843,766 A | 12/1998 | Applegate et al. | |
| 5,852,498 A | 12/1998 | Youvan et al. | |
| 5,861,251 A * | 1/1999 | Park et al. | 435/6.12 |
| 5,861,270 A | 1/1999 | Nelis | |
| 5,891,394 A | 4/1999 | Drocourt et al. | |
| 5,914,245 A | 6/1999 | Bylina et al. | |
| 5,958,790 A | 9/1999 | Cerny | |
| 5,968,766 A | 10/1999 | Powers | |
| 5,976,892 A | 11/1999 | Bisconte | |
| 5,981,180 A | 11/1999 | Chandler et al. | |
| 5,985,675 A | 11/1999 | Charm et al. | |
| 5,989,835 A | 11/1999 | Dunlay et al. | |
| 5,993,740 A | 11/1999 | Niiyama et al. | |
| 6,048,723 A | 4/2000 | Banes | |
| 6,051,395 A | 4/2000 | Rocco | |
| 6,121,055 A | 9/2000 | Hargreaves | |
| 6,122,396 A | 9/2000 | King et al. | |
| 6,130,931 A | 10/2000 | Laurila et al. | |
| 6,140,653 A | 10/2000 | Che | |
| 6,165,742 A | 12/2000 | Øfjord et al. | |
| 6,171,780 B1 | 1/2001 | Pham et al. | |
| 6,200,762 B1 | 3/2001 | Zlokarnik et al. | |
| 6,214,560 B1 | 4/2001 | Yguerabide et al. | |
| 6,258,326 B1 | 7/2001 | Modlin | |
| 6,259,807 B1 | 7/2001 | Ravkin | |
| 6,268,222 B1 | 7/2001 | Chandler et al. | |
| 6,274,384 B1 | 8/2001 | Starzl et al. | |
| 6,306,589 B1 | 10/2001 | Muller et al. | |
| 6,309,822 B1 | 10/2001 | Fodor et al. | |
| 6,345,115 B1 | 2/2002 | Ramm et al. | |
| 6,358,730 B1 | 3/2002 | Kane | |
| 6,472,166 B1 | 10/2002 | Wardlaw et al. | |
| 6,582,912 B1 | 6/2003 | Rousseau et al. | |
| 6,623,983 B1 | 9/2003 | Terstappen et al. | |
| 6,664,528 B1 | 12/2003 | Cartlidge et al. | |
| 6,710,879 B1 | 3/2004 | Hansen et al. | |
| 6,727,071 B1 | 4/2004 | Dunlay et al. | |
| 6,764,648 B1 | 7/2004 | Roach et al. | |
| 6,792,132 B1 | 9/2004 | Hara et al. | |
| 6,852,527 B2 | 2/2005 | Chan et al. | |
| 6,919,960 B2 | 7/2005 | Hansen et al. | |
| 7,068,365 B2 | 6/2006 | Hansen et al. | |
| 7,160,687 B1 | 1/2007 | Kapur et al. | |
| 7,582,415 B2 | 9/2009 | Straus | |
| 7,763,405 B2 | 7/2010 | Wu et al. | |
| 7,820,430 B2 | 10/2010 | Weng et al. | |
| 8,021,848 B2 | 9/2011 | Straus | |
| 9,090,462 B2 | 7/2015 | Straus | |
| 9,290,382 B2 | 3/2016 | Straus | |
| 2001/0039060 A1 | 11/2001 | Siiman et al. | |
| 2002/0028471 A1 | 3/2002 | Oberhardt | |
| 2002/0055092 A1 | 5/2002 | Hochman | |
| 2002/0137106 A1 | 9/2002 | Leung et al. | |
| 2003/0068638 A1 | 4/2003 | Cork et al. | |
| 2003/0082516 A1 | 5/2003 | Straus | |
| 2003/0143580 A1 | 7/2003 | Straus | |
| 2003/0170613 A1* | 9/2003 | Straus | 435/5 |
| 2004/0048395 A1 | 3/2004 | Lee et al. | |
| 2004/0171121 A1 | 9/2004 | Leppla et al. | |
| 2004/0172000 A1 | 9/2004 | Roe et al. | |
| 2004/0246483 A1 | 12/2004 | Hansen et al. | |
| 2005/0013737 A1 | 1/2005 | Chow et al. | |
| 2005/0148085 A1 | 7/2005 | Larsen | |
| 2005/0191687 A1 | 9/2005 | Wang et al. | |
| 2005/0220670 A1 | 10/2005 | Palmieri et al. | |
| 2005/0221403 A1 | 10/2005 | Gazenko | |
| 2005/0225766 A1 | 10/2005 | Hansen et al. | |
| 2005/0226779 A1 | 10/2005 | Oldham et al. | |
| 2006/0006067 A1 | 1/2006 | Unger | |
| 2006/0051816 A1 | 3/2006 | Hsieh et al. | |
| 2006/0121055 A1 | 6/2006 | Campbell et al. | |
| 2006/0129327 A1 | 6/2006 | Kim et al. | |
| 2006/0188967 A1 | 8/2006 | Nalin et al. | |
| 2006/0210435 A1 | 9/2006 | Alavie et al. | |
| 2006/0216696 A1 | 9/2006 | Goguen | |
| 2006/0256340 A1 | 11/2006 | Hansen et al. | |
| 2006/0292552 A1 | 12/2006 | Haquette et al. | |

(56) References Cited

U.S. PATENT DOCUMENTS

| | | | |
|---|---|---|---|
| 2007/0014695 | A1 | 1/2007 | Yue et al. |
| 2007/0172899 | A1* | 7/2007 | Graham ................ G01N 33/80 435/7.21 |
| 2007/0184546 | A1 | 8/2007 | Farrelly et al. |
| 2007/0212681 | A1 | 9/2007 | Shapiro et al. |
| 2007/0212747 | A1 | 9/2007 | Browne et al. |
| 2008/0003571 | A1 | 1/2008 | McKernan et al. |
| 2008/0014576 | A1 | 1/2008 | Jovanovich et al. |
| 2008/0032328 | A1 | 2/2008 | Cline et al. |
| 2008/0038738 | A1 | 2/2008 | Weigum et al. |
| 2008/0200343 | A1 | 8/2008 | Clemens et al. |
| 2008/0206099 | A1 | 8/2008 | Aruga et al. |
| 2009/0315987 | A1 | 12/2009 | Straus |
| 2010/0248281 | A1 | 9/2010 | Straus |
| 2012/0045826 | A1 | 2/2012 | Yantz et al. |
| 2012/0046203 | A1 | 2/2012 | Walsh et al. |
| 2013/0011566 | A1 | 1/2013 | Colin et al. |

FOREIGN PATENT DOCUMENTS

| | | |
|---|---|---|
| DE | 19608320 A1 | 8/1997 |
| DE | 19631997 A1 | 2/1998 |
| DE | 19940810 A1 | 5/2000 |
| EP | 0171174 A2 | 2/1986 |
| EP | 0574977 A1 | 12/1993 |
| EP | 0753732 A2 | 1/1997 |
| EP | 1207394 A2 | 5/2002 |
| EP | 1508374 A2 | 2/2005 |
| JP | S62-501647 A | 7/1987 |
| JP | H02-502405 A | 8/1990 |
| JP | 3102240 A | 4/1991 |
| JP | H3-83598 A | 4/1991 |
| JP | 10-295362 A | 11/1998 |
| JP | H11-346795 A | 12/1999 |
| JP | 2000-509827 A | 8/2000 |
| JP | 2001-224355 A | 8/2001 |
| JP | 2001-512875 A | 8/2001 |
| JP | 2002-125656 A | 5/2002 |
| JP | 2003-294596 A | 10/2003 |
| JP | 2006-087336 A | 4/2006 |
| JP | 2006-162466 A | 6/2006 |
| JP | 2007-526807 A | 9/2007 |
| JP | 2008-96223 A | 4/2008 |
| JP | 2008-513022 A | 5/2008 |
| JP | 2009-513111 A | 4/2009 |
| WO | WO-83/01581 A1 | 5/1983 |
| WO | WO-86/04684 A1 | 8/1986 |
| WO | WO-89/05456 A1 | 6/1989 |
| WO | WO-92/05448 A2 | 4/1992 |
| WO | WO-97/40181 A1 | 10/1997 |
| WO | WO-97/44664 A1 | 11/1997 |
| WO | WO-98/38490 A1 | 9/1998 |
| WO | WO-98/50577 A1 | 11/1998 |
| WO | WO-99/08233 A1 | 2/1999 |
| WO | WO-99/20789 A1 | 4/1999 |
| WO | WO-99/35483 A1 | 7/1999 |
| WO | WO-99/36577 A1 | 7/1999 |
| WO | WO-99/58948 A2 | 11/1999 |
| WO | WO-00/04382 A1 | 1/2000 |
| WO | WO-00/47766 A1 | 8/2000 |
| WO | WO-01/57522 A2 | 8/2001 |
| WO | WO-01/61348 A1 | 8/2001 |
| WO | WO-03/036290 A1 | 5/2003 |
| WO | WO-03/073817 A2 | 9/2003 |
| WO | WO-2005/082254 A2 | 9/2005 |
| WO | WO-2006/032044 A2 | 3/2006 |
| WO | WO-2008/005998 A1 | 1/2008 |
| WO | WO-2010/036808 A1 | 4/2010 |
| WO | WO-2010/036827 A1 | 4/2010 |
| WO | WO-2010/036829 A1 | 4/2010 |
| WO | WO-2011/117545 A1 | 9/2011 |
| WO | WO-2013/070730 A2 | 5/2013 |
| WO | WO-2013/158666 A1 | 10/2013 |

OTHER PUBLICATIONS

Al-Hakiem et al., "Development of Fluoroimmunoassays for the Determination of Individual or Combined Levels of Procainamide and N-Acetylprocainamide in Serum." *J. Immunoassay* 3(1):91-110, 1982.

Allman et al., "Fluoroimmunoassay of Progesterone in Human Serum or Plasma" *Clin. Chem.* 27: 1176-1179, 1981.

The brain, <http://www.enchantedlearning.com/subjects/anatomy/_brain/neuron.html>, retrieved Nov. 4, 2007 (4 pages).

Clean Technology, 5(8), 60-61 (1995) (No english translation provided).

Colony Counter (<http://www.topac.com/acolyte.html>), retrieved Apr. 12, 2005 (3 pages).

Colony Counter Models and Specifications (<http://biologics-inc.com/cc-models.htm>), retrieved Apr. 15, 2005 (3 pages).

Corkidi et al., "COVASIAM: An Image Analysis Method That Allows Detection of Confluent Microbial Colonies and Colonies of Various Sizes for Automated Counting," *Appl. Environ. Microbiol.* 64(4):1400-1404, 1998.

Definition and Procedure for the Determination of the Method Detection Limit, Appendix B to 40 C.F.R. § 136, available at <http://access.gpo.gov> (retrieved Nov. 20, 2007), pp. 343-346.

Digital Multi-Purpose High-Resolution Colony and Plaque Counter (<http://www.loats.com/mla.html>) retrieved Apr. 12, 2005 (3 pages).

Esteban et al., "Improved Direct Epifluorescent Filter Technique for Rapid Bioburden Control in Intravenous Solutions," *J. Parenter. Sci. Technol.* 46: 146-149, 1992.

Frost, "Improved Technic for the Micro or Little Plate Method of Counting Bacteria in Milk," *J. Infect. Dis.* 28(2):176-184, 1921.

"Innovative Plate Holder for Colony Counter," <http://www.laboratorytalk.com> retrieved Oct. 16, 2002 (2 pages).

"Innovative Plate Holder for ProtoCOL," <http://www.synbiosis.com> retrieved Oct. 16, 2002 (2 pages).

Kamentsky, "Laser Scanning Cytometry," *Methods Cell Biol.* 63: 51-87, 2001.

Kroll et al. "A Laser-Light Pulse Counting Method for Automatic and Sensitive Counting of Bacteria Stained with Acridine Orange", *J. Appl. Bacteriol.* 66: 161-167, 1989.

Lamture et al., "Direct Detection of Nucleic Acid Hybridization on the Surface of a Charge Coupled Device," *Nucleic Acids Res.* 22(11): 2121-5, 1994.

Loats et al., "LAI High-Resolution Automated Colony Counting System—Mouse Lymphoma Assay: Performance Analysis," (<http://loats.com/docs/HRCCval/HRCCval.htm>), p. 1-11 (1990).

Logtenberg et al., "Enumeration of (Auto)Antibody Producing Cells in Human Using the 'Spot-ELISA,'" *Immunol. Lett.* 9: 343-347, 1985.

London et al., "An Automated System for Rapid Non-Destructive Enumeration of Growing Microbes," *PLoS One* 5(1):e8609 (16 pages) (2010).

Masuko et al., "A Novel Method for Detection and Counting of Single Bacteria in a Wide Field Using an Ultra-High-Sensitivity TV Camera Without a Microscope," *FEMS Microbiol. Lett.* 81: 287-290, 1991.

Masuko et al., "Rapid Detection and Counting of Single Bacteria in a Wide Field Using a Photon-Counting TV Camera," *FEMS Microbiol. Lett.* 83: 231-238, 1991.

Mignon-Godefroy et al., "Solid Phase Cytometry for Detection of Rare Events," *Cytometry* 27: 336-344, 1997.

Miraglia et al., "Homogeneous Cell-and Bead-Based Assays for High Throughput Screening Using Fluorometric Microvolume Assay Technology," *J. Biomol. Screen.* 4: 193-204, 1999.

Moore et al, "Lymphocyte fractionation using immunomagnetic colloid and a dipole magnet flow cell sorter," *J. Biochem. Biophys. Methods* 37: 11-33, 1998.

Nargessi et al., "Magnetizable Solid-Phase Fluoroimmunoassay of Thyroxine by a Sequential Addition Technique." *Clin Chem* 26(12): 1701-1703, 1980.

(56) References Cited

OTHER PUBLICATIONS

Nargessi et al., "Immunoassays for Serum C-Reactive Protein Employing Fluorophore-Labelled Reactants." *J. Immunol. Methods* 71: 17-24, 1984.

Nelis et al. "Enzymatic Detection of 1-15 Coliforms and *Escherichia coli* Within 4 Hours," *Water Air and Soil Pollut.* 123: 43-52, 2000.

PerkinElmer, Inc., GeneScreenTM Hybridization Transfer Membranes, Application Notes, available at <http://las.perkinelmer.com/>, retrieved Feb. 27, 2007.

Rousseau et al., "New Miniaturized Highly Sensitive Immunoassay Device for Quantitative Measurement of Soluble or Particular Antigen or Antibodies in a Liquid Sample," *Clin. Chem.* 45(9): 1685-1687, 1999.

Schultz et al., "Single Target Molecule Detection with Nonbleaching Multicolor Optical Immunolabels," *Proc. Natl. Acad. Sci. U.S.A.* 97(3): 996-1001, 2000.

Sorcerer Automated Colony Counting, Perceptive Instruments, 2002 (2 pages).

Susa et al., "Legionella Pneumophila Infection in Intratracheally Inoculated T Cell-Depleted or -Nondepleted A/J Mice," *J. Immunol.* 160: 316-321, 1998.

Loates Associates Inc., System Specifications (<http://www.loats.com/order_info.html>), retrieved Apr. 12, 2005, (1999) (7 pages).

Technical Specification (<http://www.perceptive.co.uk/products/_scc/techspec.html>), retrieved Apr. 12, 2005 (2 pages).

Thomas et al., "Making Gold Nanoparticles Glow: Enhanced Emission from a Surface-Bound Fluoroprobe," *J. Am. Chem. Soc.* 122: 2655-2656, 2000.

Tibbe et al., "Optical Tracking and Detection of Immunomagnetically Selected and Aligned Cells," *Nature Biotechnol.* 17: 1210-1213, 1999.

Van Poucke et al. "Solid Phase Cytometry-Based Enzymatic Detection of Coliforms in Drinking Water Within 4 h", *Water Supply* 17: 67-72, 1999.

Van Poucke et al. "Rapid Detection of Fluorescent and Chemiluminescent Total Coliforms and *Escherichia coli* on Membrane Filters" *J. Microbiol. Methods* 42: 233-244, 2000.

Van Poucke et al., "A 210-min Solid Phase Cytometry Test for the Enumeration of *Escherichia coli* in Drinking Water," *J. Appl. Microbiol.* 89: 390-396, 2000.

Vidon et al., "A Simple Chemiluminescence-Based Method for Rapid Enumeration of *Listeria* spp. Microcolonies," *J. Appl. Microbiol.* 90: 988-993, 2001.

Viinikka et al., "A Two-Site Immunofluorometric Assay for Human Placental Lactogen," *Clin. Chim. Acta.* 114: 1-9, 1981.

Wellman et al., "Magnetically-Assisted Transport Evanescent Field Fluoroimmunoassay," *Anal. Chem.* 78: 4450-6, 2006.

Wilson, "Use of the IUL Countermat Automatic Colony Counter for Spiral Plated Total Viable Counts," *Appl. Environ. Microbiol.* 61: 3158-3160, 1995.

Wolniak, 2004. BSCI 427 Principles of Microscopy Fall 2004 Syllabus, (<http://www.life.umd.edu/cbmg/faculty/wolniak_/wolniakmicro.html>), retrieved Nov. 8, 2007 (8 pages).

Yasui et al., "Imaging of *Lactobacillus brevis* Single Cells and Microcolonies Without a Microscope by an Ultrasensitive Chemiluminescent Enzyme Immunoassay with a Photon-Counting Television Camera," *Appl. Environ. Microbiol.* 63: 4528-4533, 1997.

Zhao et al., "Competitive Immunoassay for Microliter Protein Samples with Magnetic Beads and Near-infrared Fluorescence Detection." *Anal. Chem.* 76: 1871-1876, 2004.

International Search Report for International Application No. PCT/US2009/58270, mailed Dec. 2, 2009 (2 pages).

Written Opinion for International Application No. PCT/US2009/58270, mailed Dec. 2, 2009 (8 pages).

Extended European Search Report for European Patent Application No. 09816871, dated Mar. 14, 2012 (7 pages).

Patterson, "A wide angle camera for photographic search of the ocean bottom," SPIE. C-XII-1-8 (1966).

Findlay et al., "Automated closed-vessel system for in vitro diagnostics based on polymerase chain reaction," Clin Chem. 39(9):1927-33 (1993).

U.S. Appl. No. 15/057,393, Straus.

\* cited by examiner

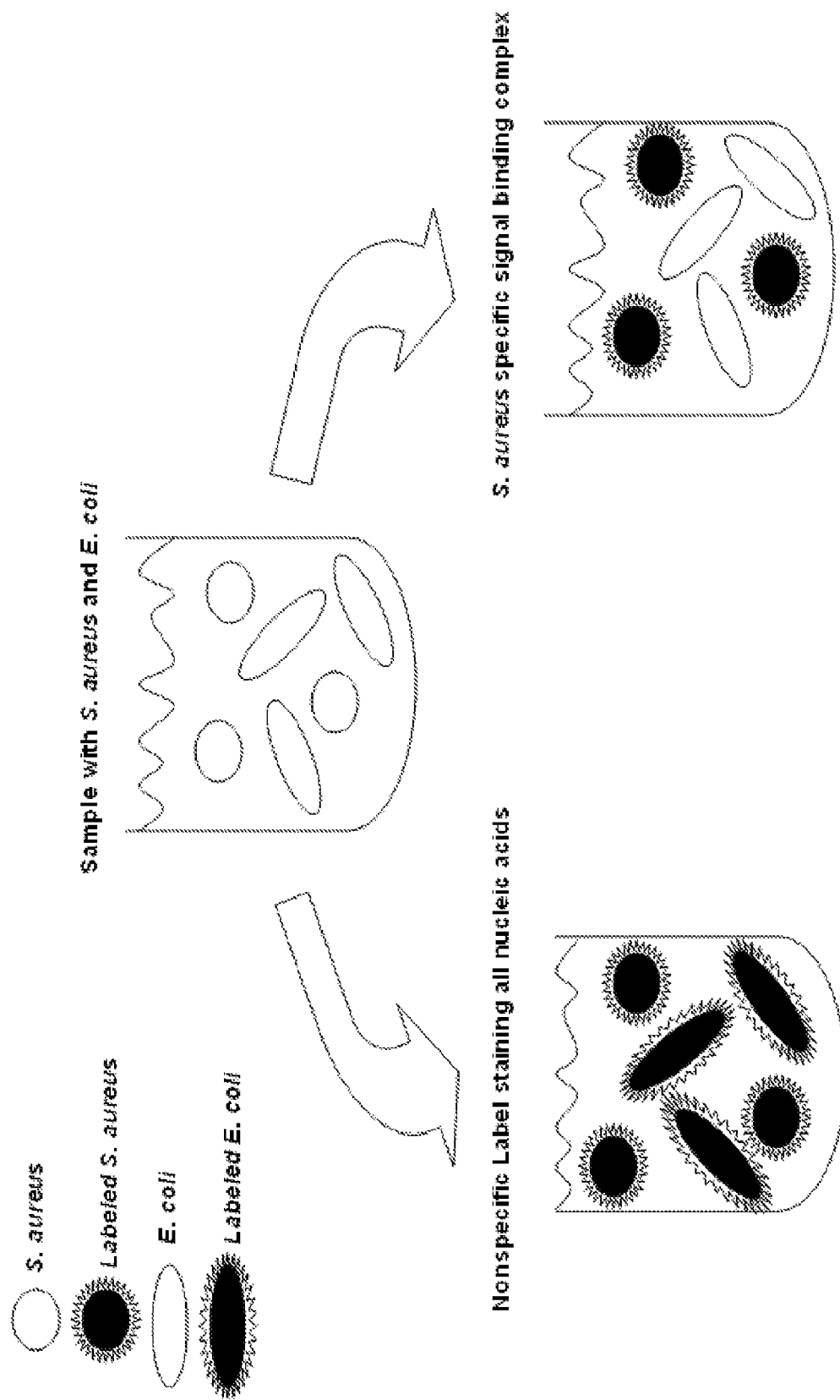
Fig. 1 Specific vs. Nonspecific Labeling.

| Sample | Label | Additional Components/ Diluents | Selection Agent | Additional Components/ Diluents |
|---|---|---|---|---|
| | | | | |

Separate Addition: Liquid | Liquid | Liquid | Liquid | Liquid

Combined Addition Liquid: Liquid | Liquid

Combined Addition Liquid: Liquid | Liquid

Some Reagents Dried: Liquid | Liquid | Dried | Liquid

All Reagents Dried: Liquid | Dried | Dried | Dried

All Reagents Dried and Combined: Liquid | Dried

Fig. 2 Methods for contacting the sample with other reaction components.

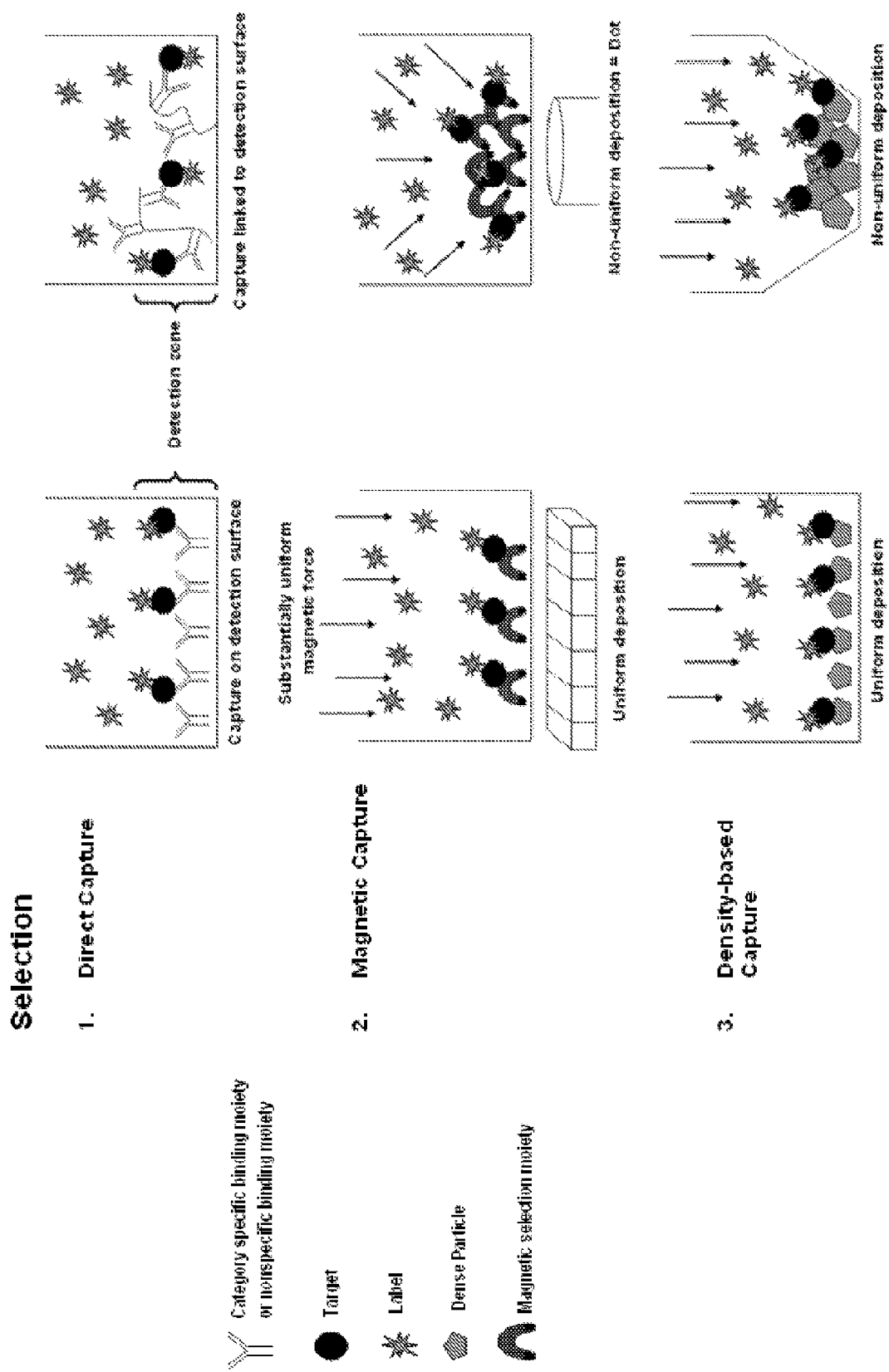
Fig. 3  Different methods for capture of targets.

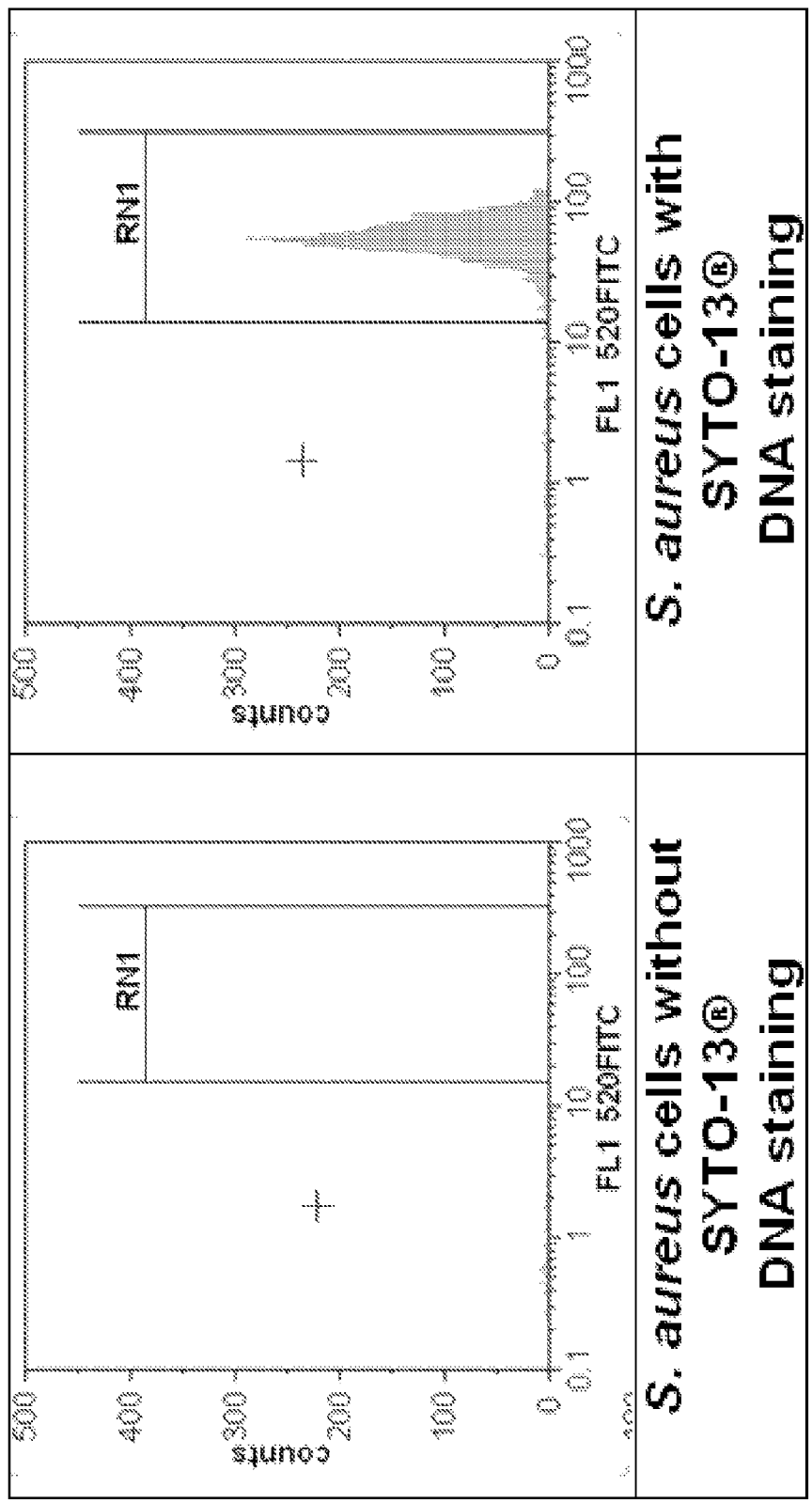
Fig. 4  Labeling of *S. aureus* with Fluorogenic DNA stain- Relative log fluorescence intensity of SYTO-13® staining of *S. aureus* DNA (Example 1).

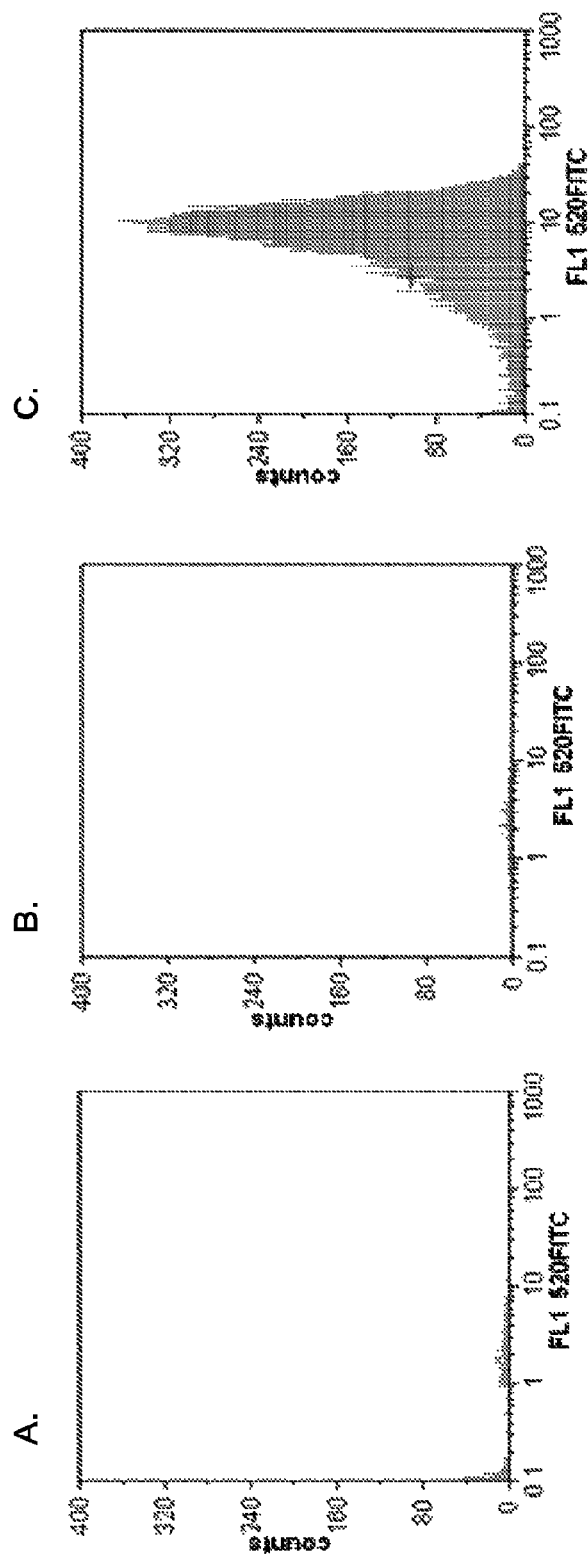
Fig. 5 Labeling of *Staphylococcus aureus* cells with chicken anti-protein A antibodies conjugated to fluorescent nanoparticles. Relative log fluorescence intensity of *S. aureus* cells stained by antibody coated fluorescent particles (Example 3).

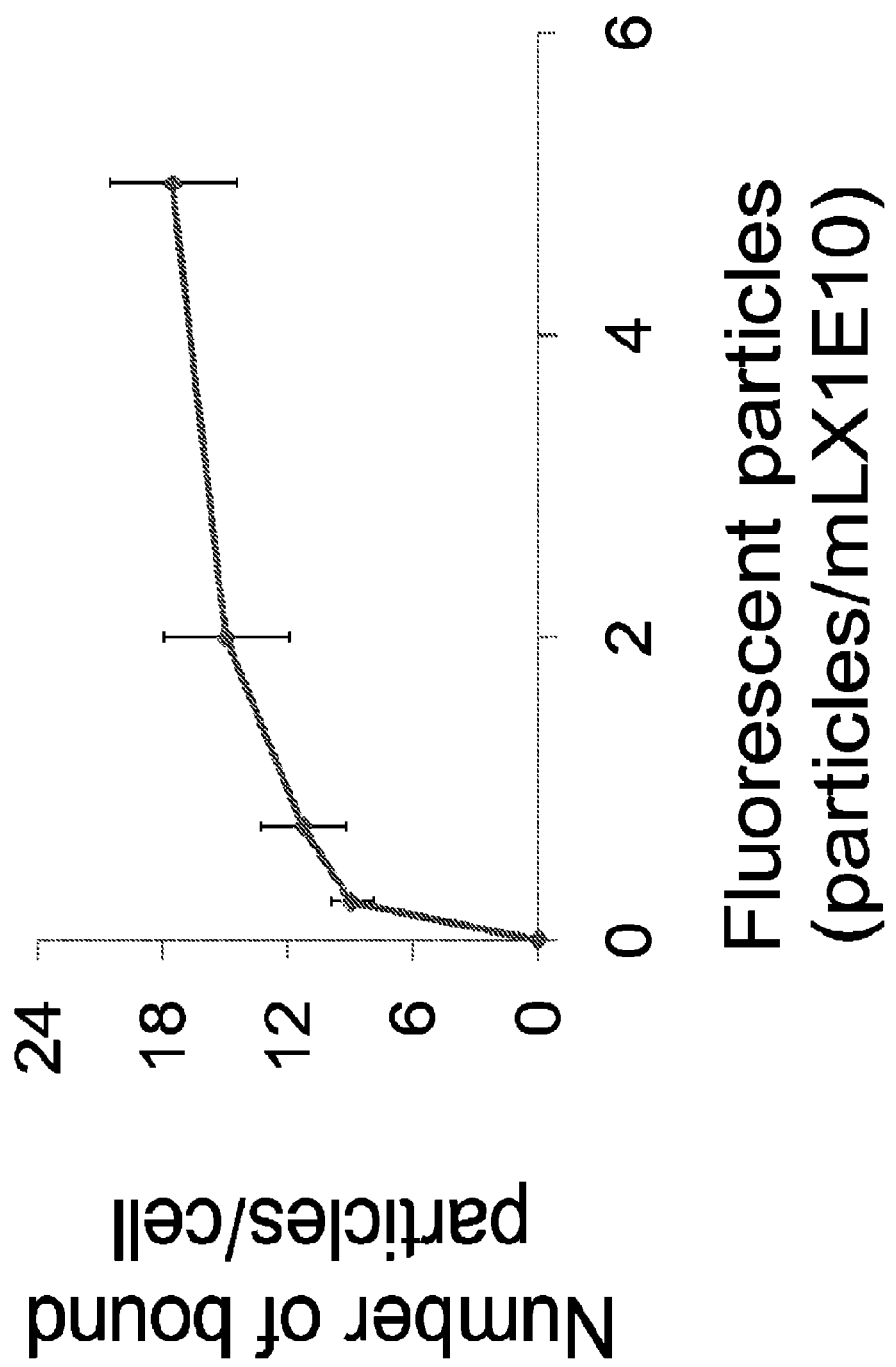
Fig. 6  Determining binding efficiency of *S. aureus* specific fluorescent particles by flow cytometry (Example 3).

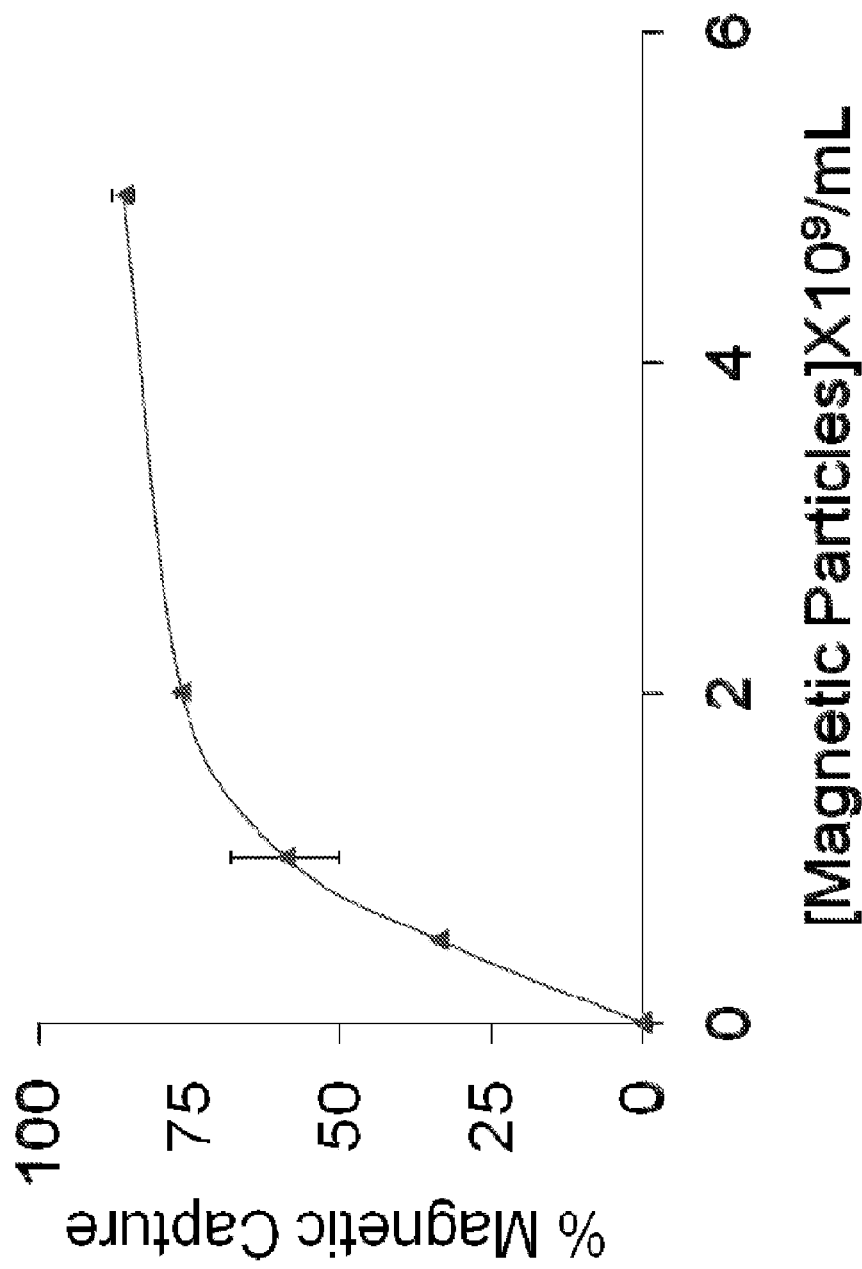
Fig. 7  Testing magnetic particles coated with anti-*Staphylococcus aureus* antibodies. Bioassay shows number of magnetic particles vs. percentage magnetic capture of *S. aureus* after magnetic selection (Example 4).

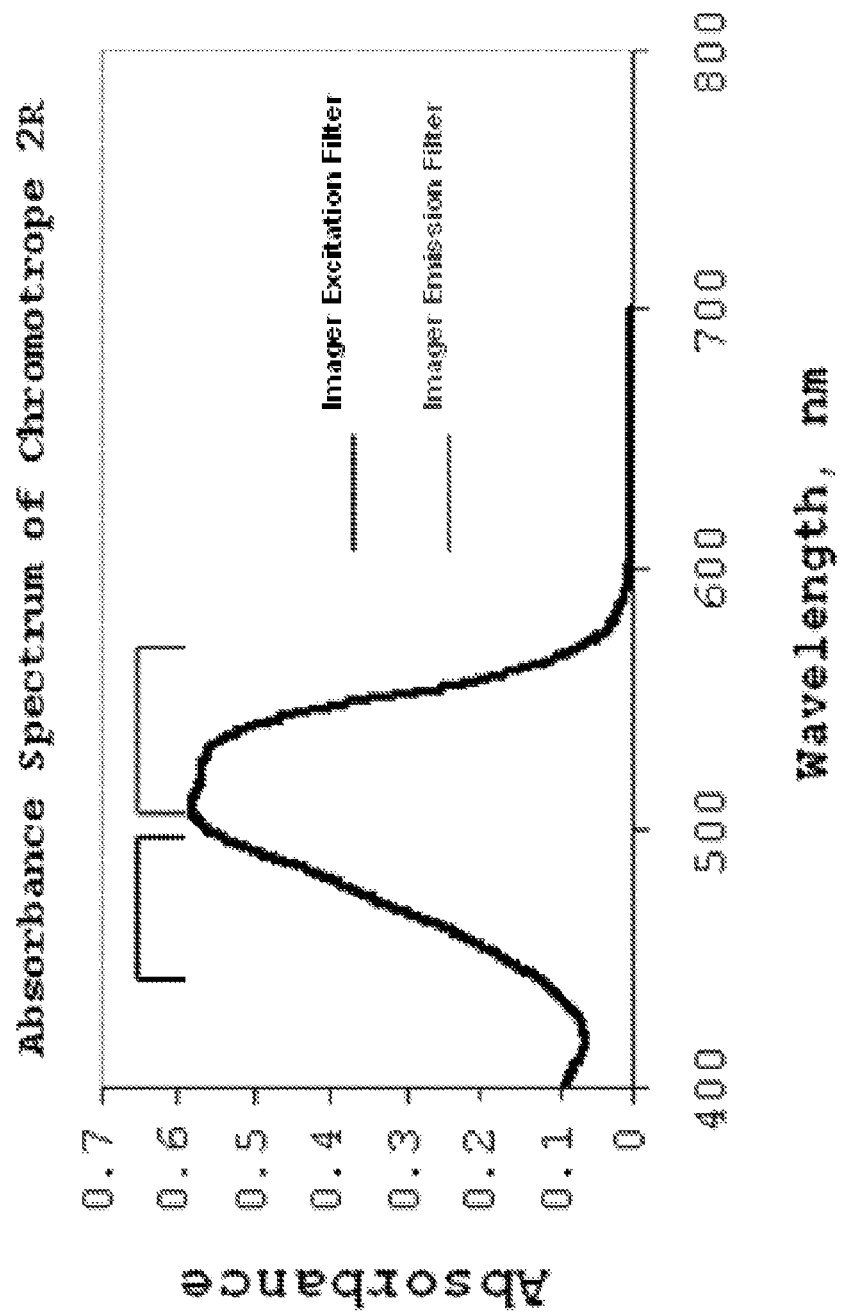
Fig. 8  Chromotrope 2R dye absorbs light at wavelengths corresponding to light passed by the excitation and emission filters used in the imager. (Example 5)

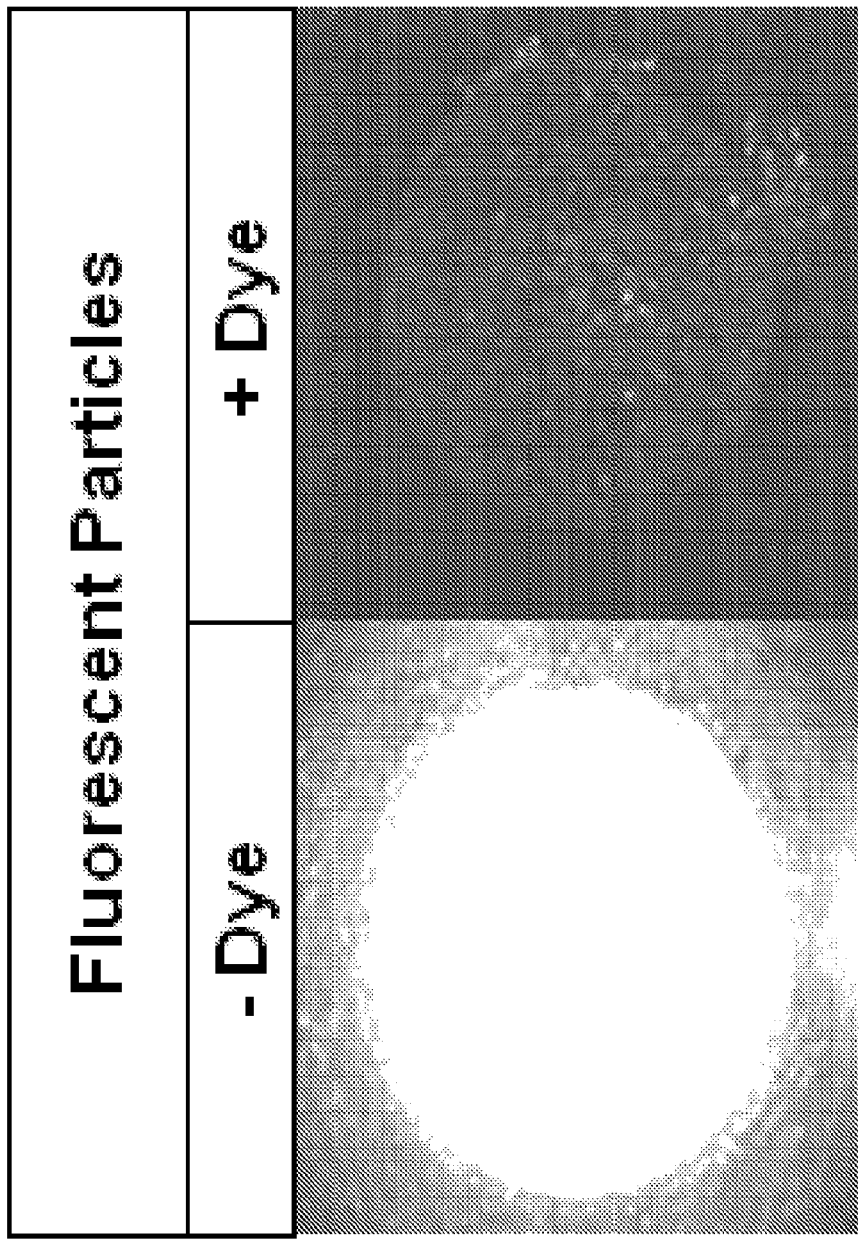
Fig. 9  Dye can be used to attenuate the signal from fluorescent particles. (Example 5)

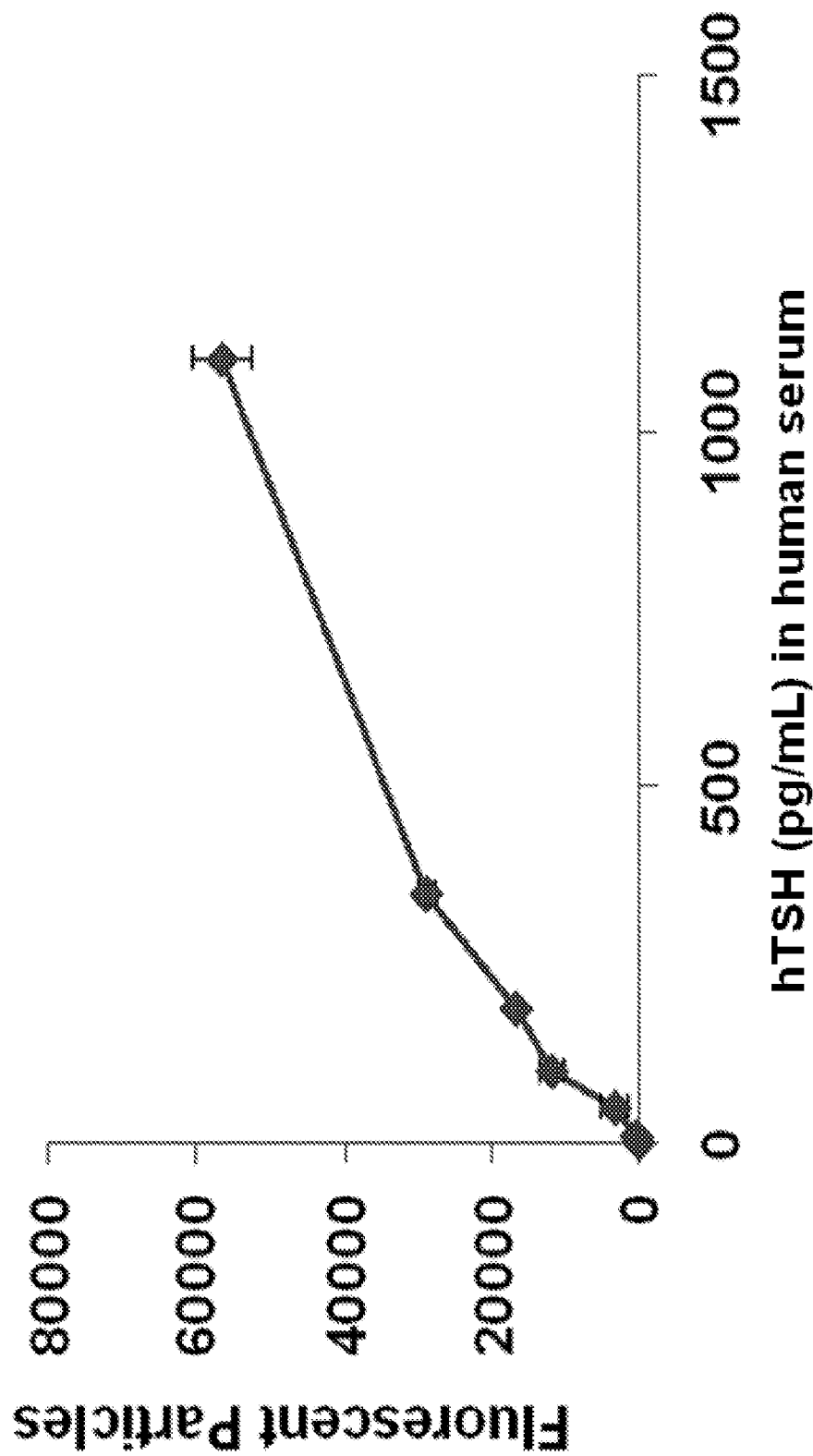
Fig. 10  Assay of Human Thyroid Stimulating Hormone (hTSH) in human serum using magnetic capture and dye. (Example 5)

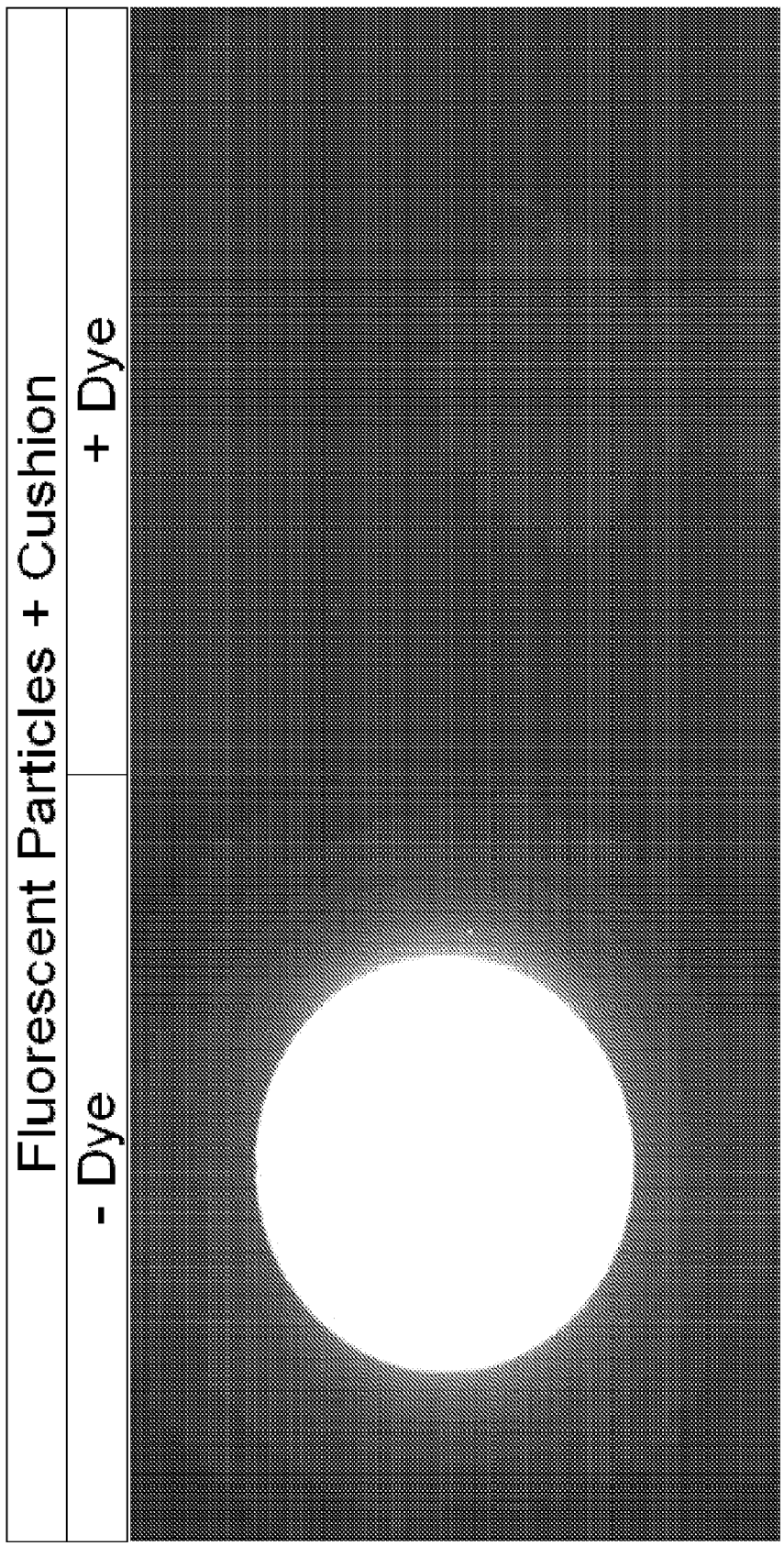
Fig. 11 Test of Dye-cushion reagent demonstrating the effect of dye and cushion using human Thyroid Stimulating Hormone assay reagents. (Example 6)

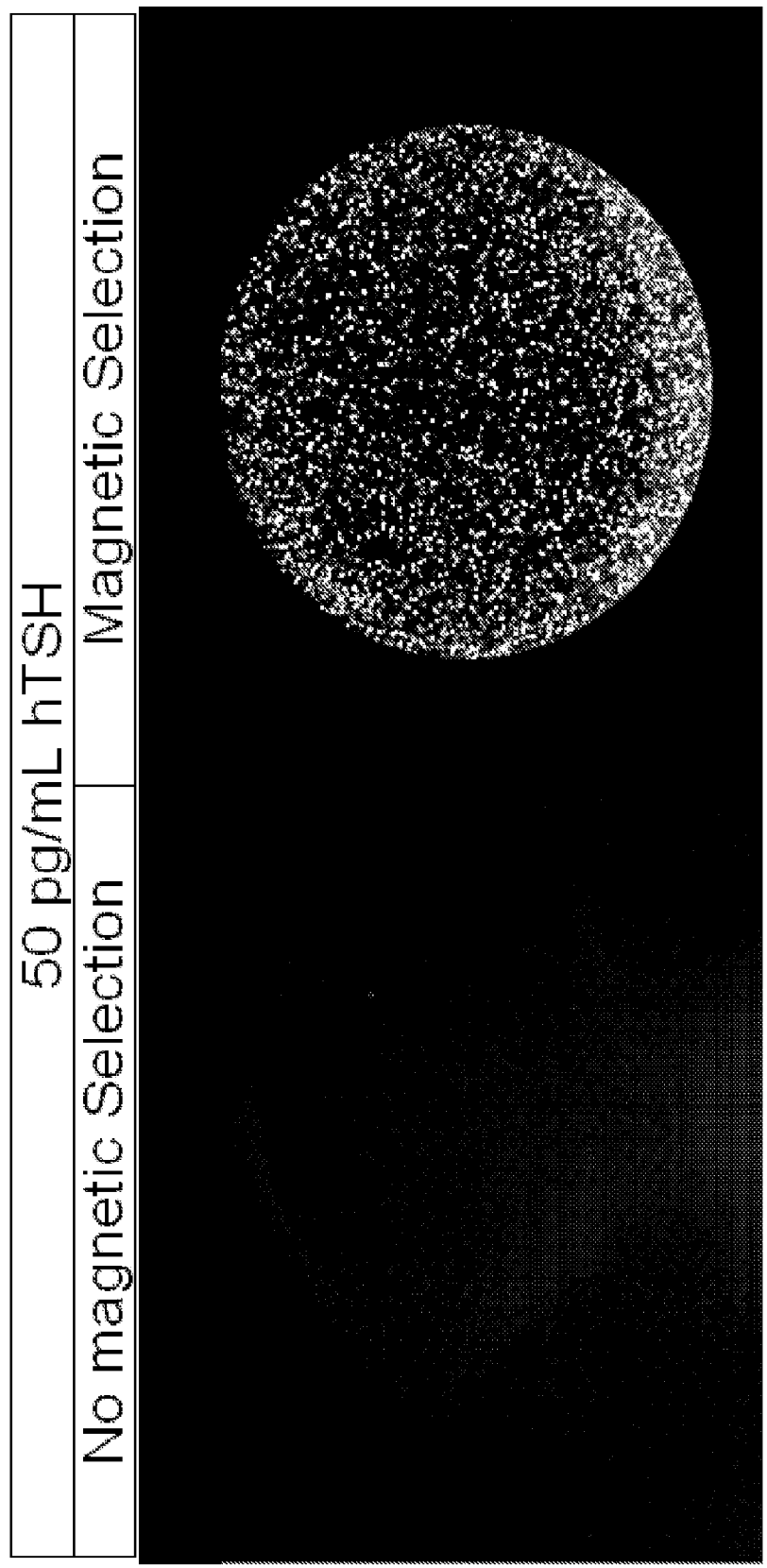
Fig. 12 Test of dye cushion reagent demonstrating the effect of dye and of cushion using TSH assay reagents- Magnetic selection experiment for hTSH. (Example 6)

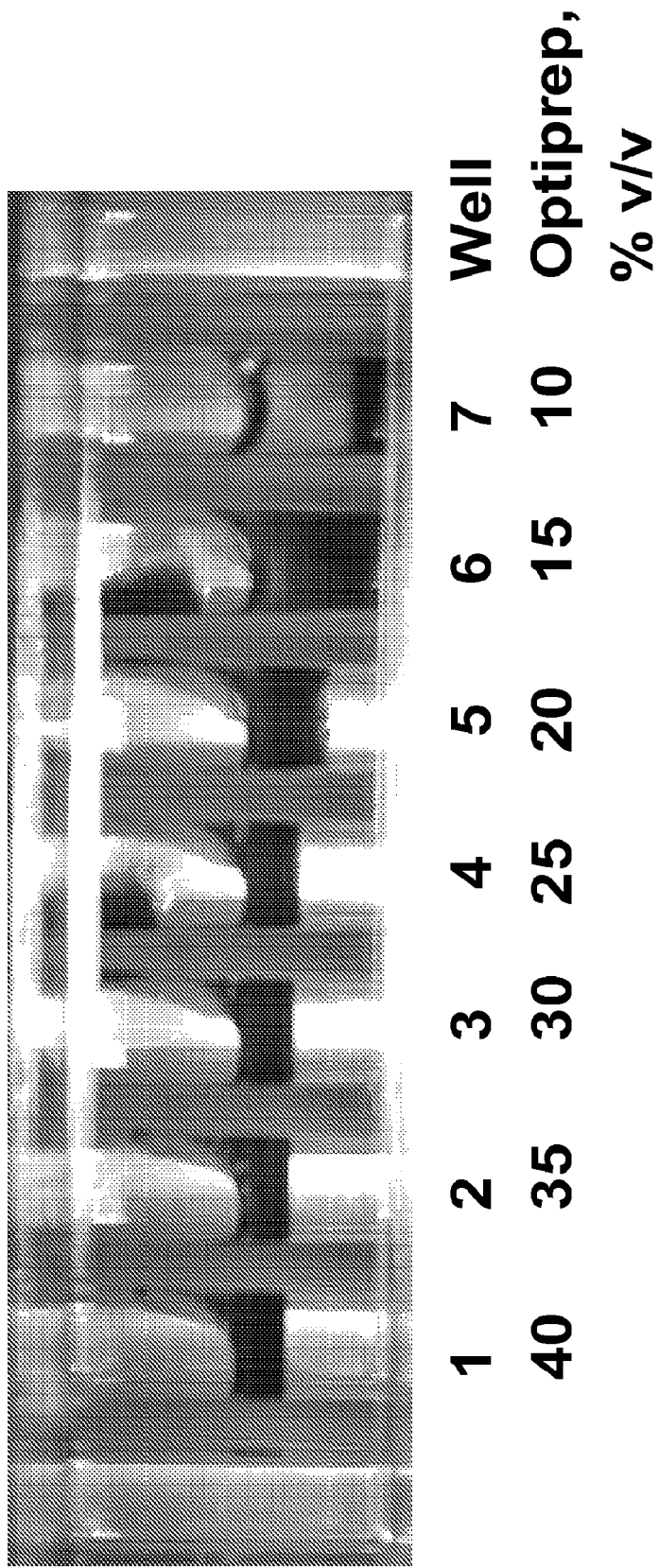
Fig. 13  Concentration of density agent needed to form a bilayer system when the sample is whole blood. (Example 7)

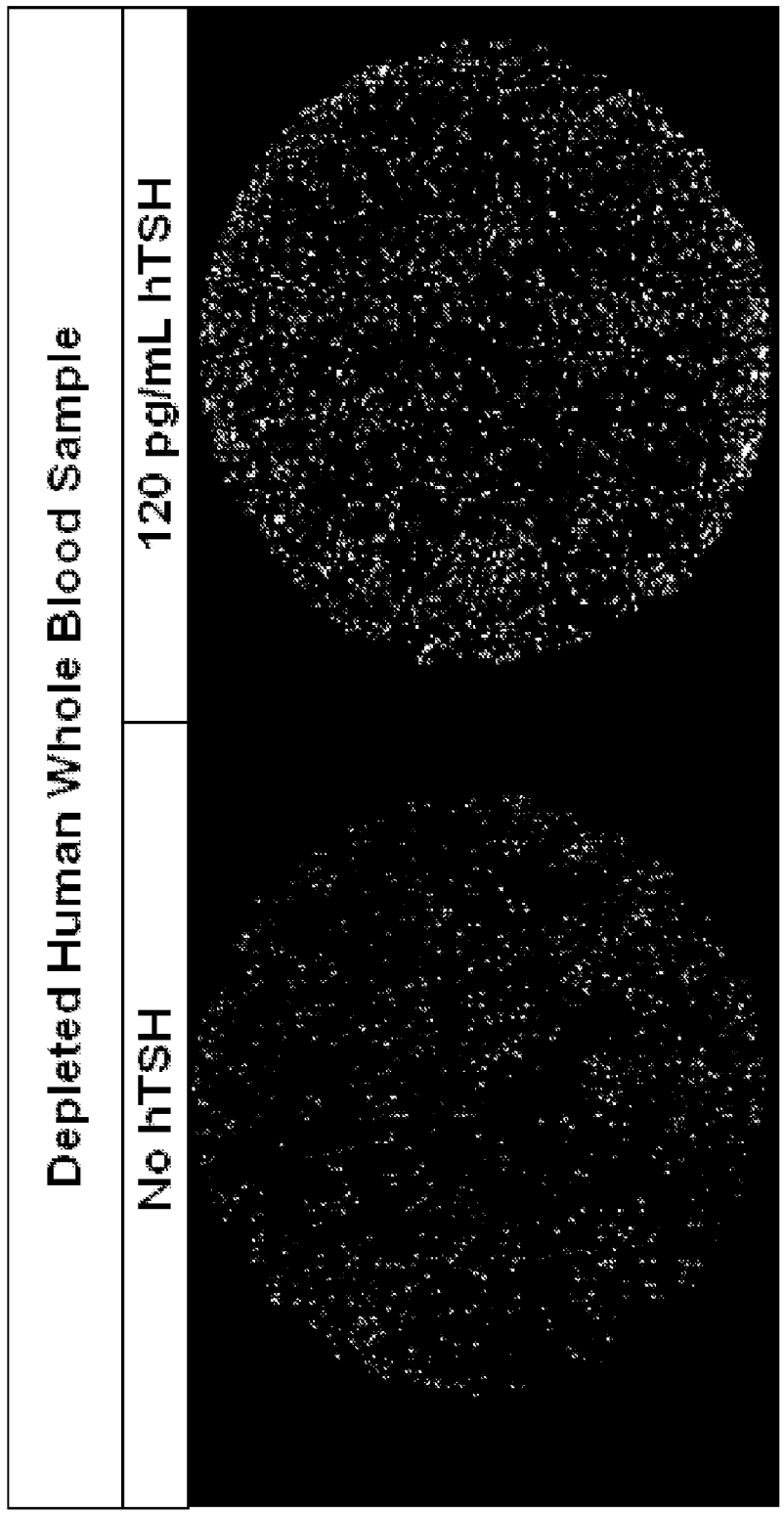
Fig. 14 Sensitive detection of hTSH in whole blood by enumeration of individual fluorescent microparticles after selection through a dye cushion. (Example 8)

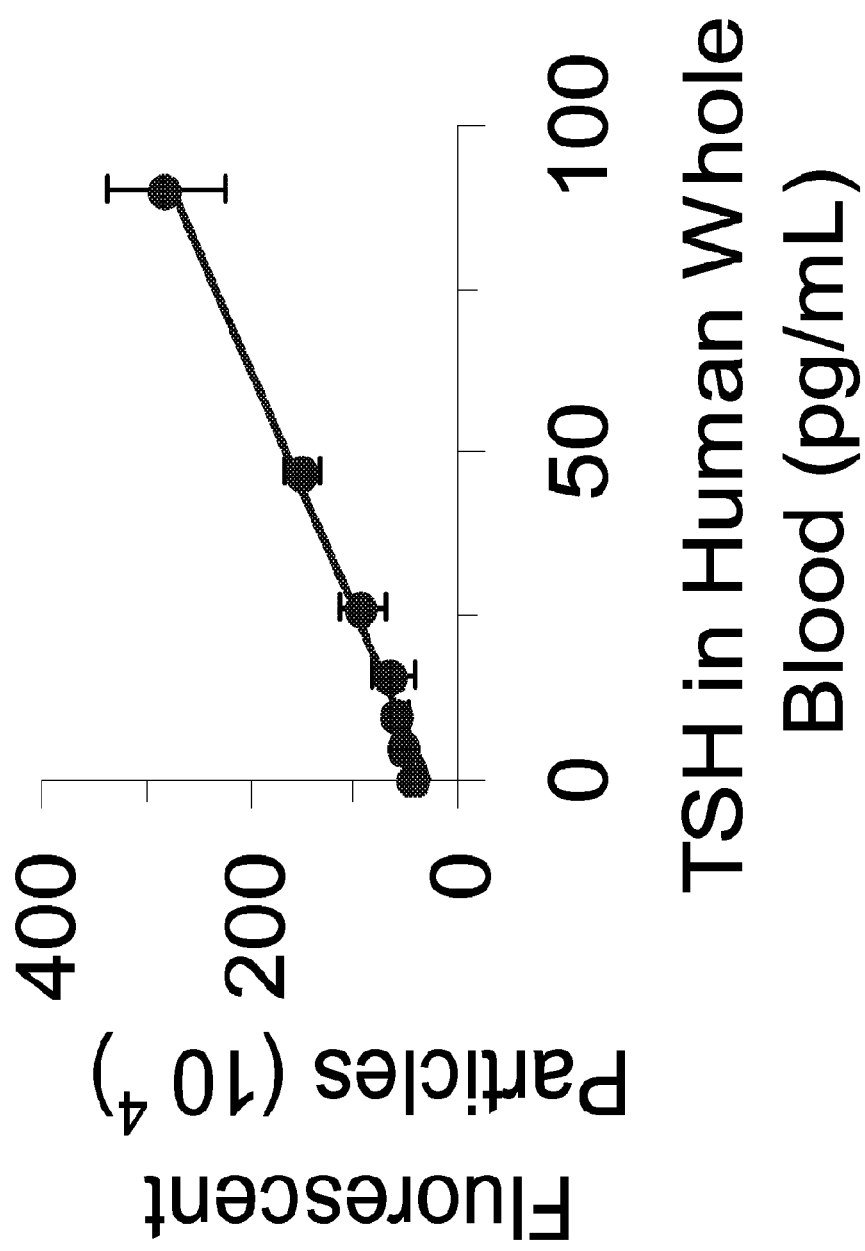
Fig. 15 Detection of human Thyroid Stimulating Hormone (hTSH) in human whole blood using magnetic capture, cushion dye reagent, carrier magnets. (Example 8)

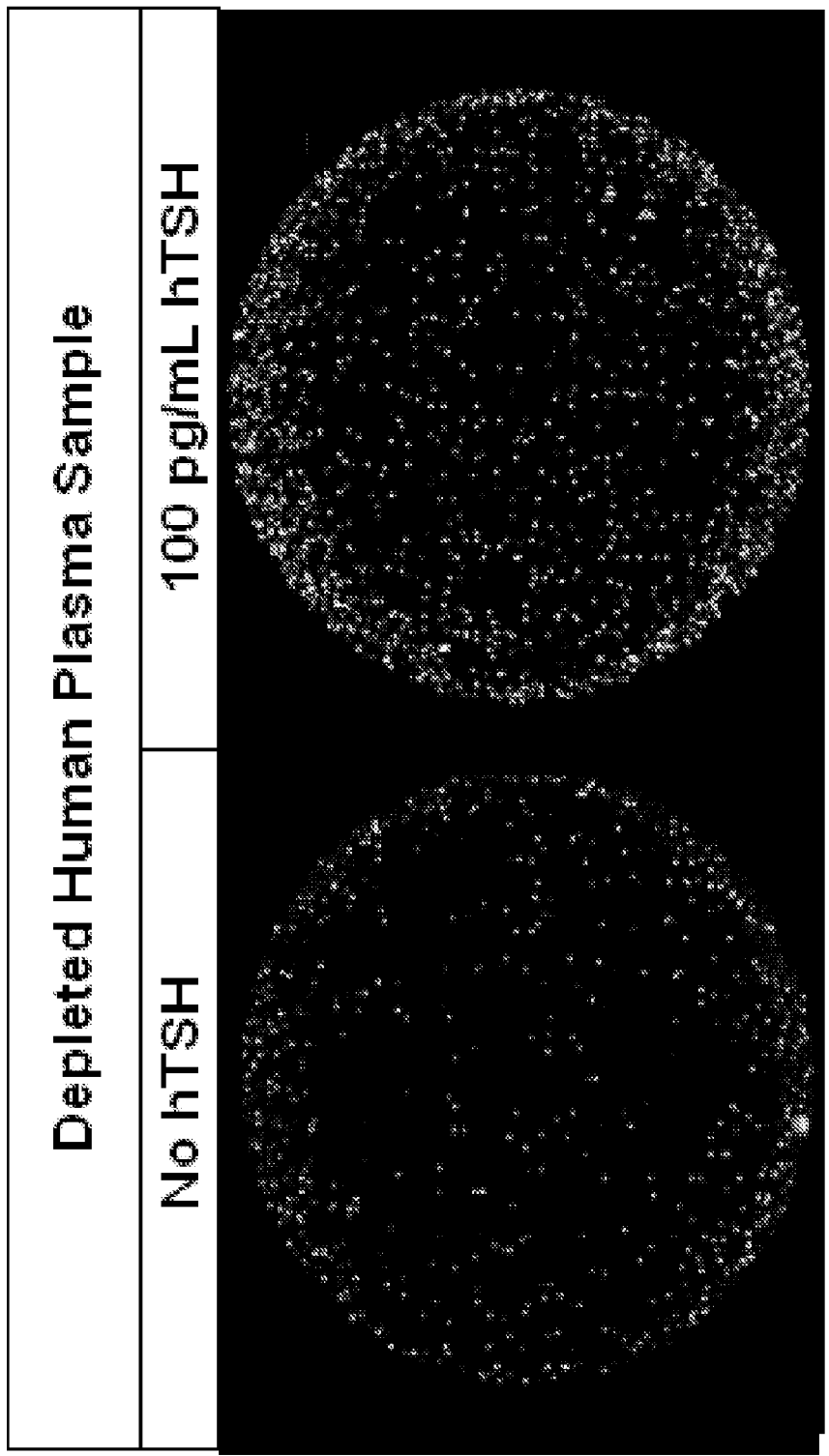
Fig. 16 Assay of Human Thyroid Stimulating Hormone (hTSH) in human plasma using dispersed magnetic capture and cushion dye reagent. (Example 9)

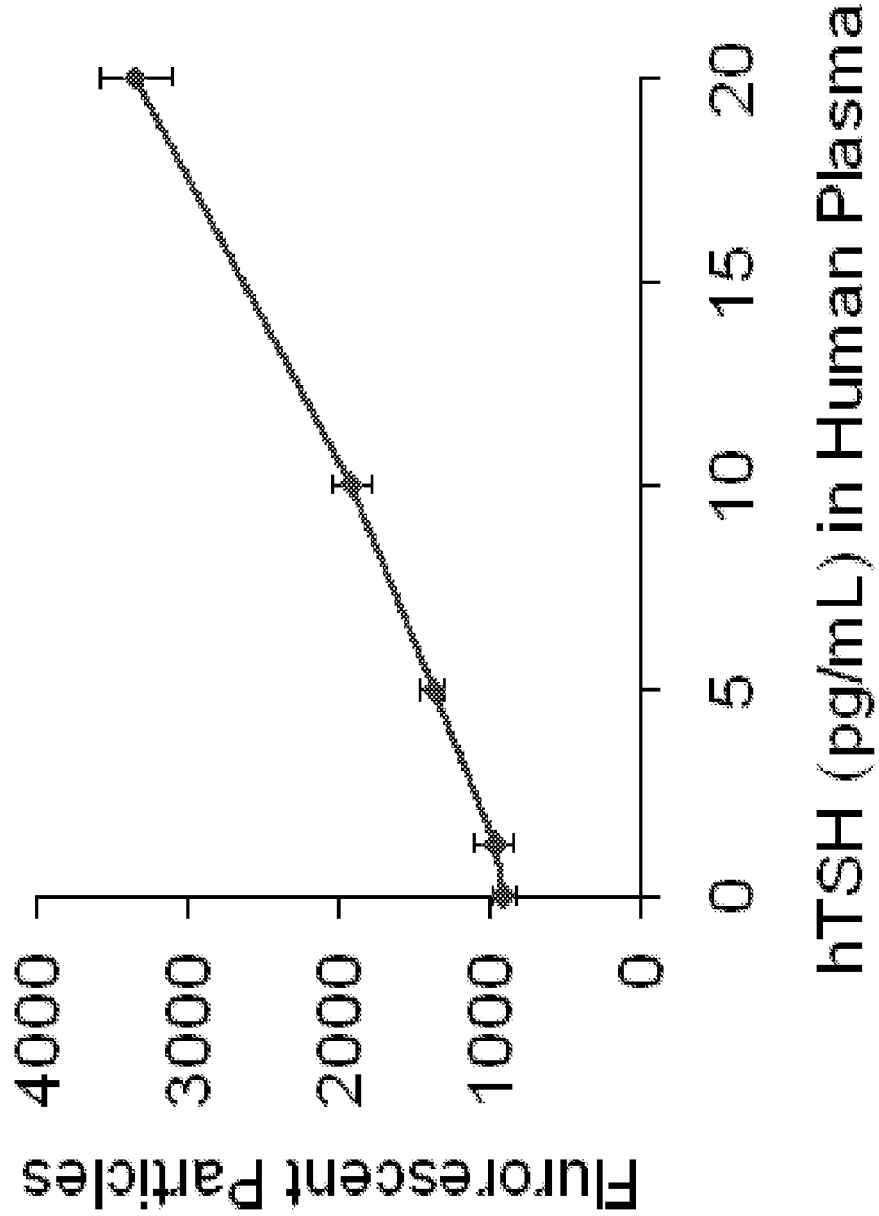
Fig. 17  Assay of Human Thyroid Stimulating Hormone (hTSH) in human plasma using dispersed magnetic capture and cushion dye reagent. (Example 9)

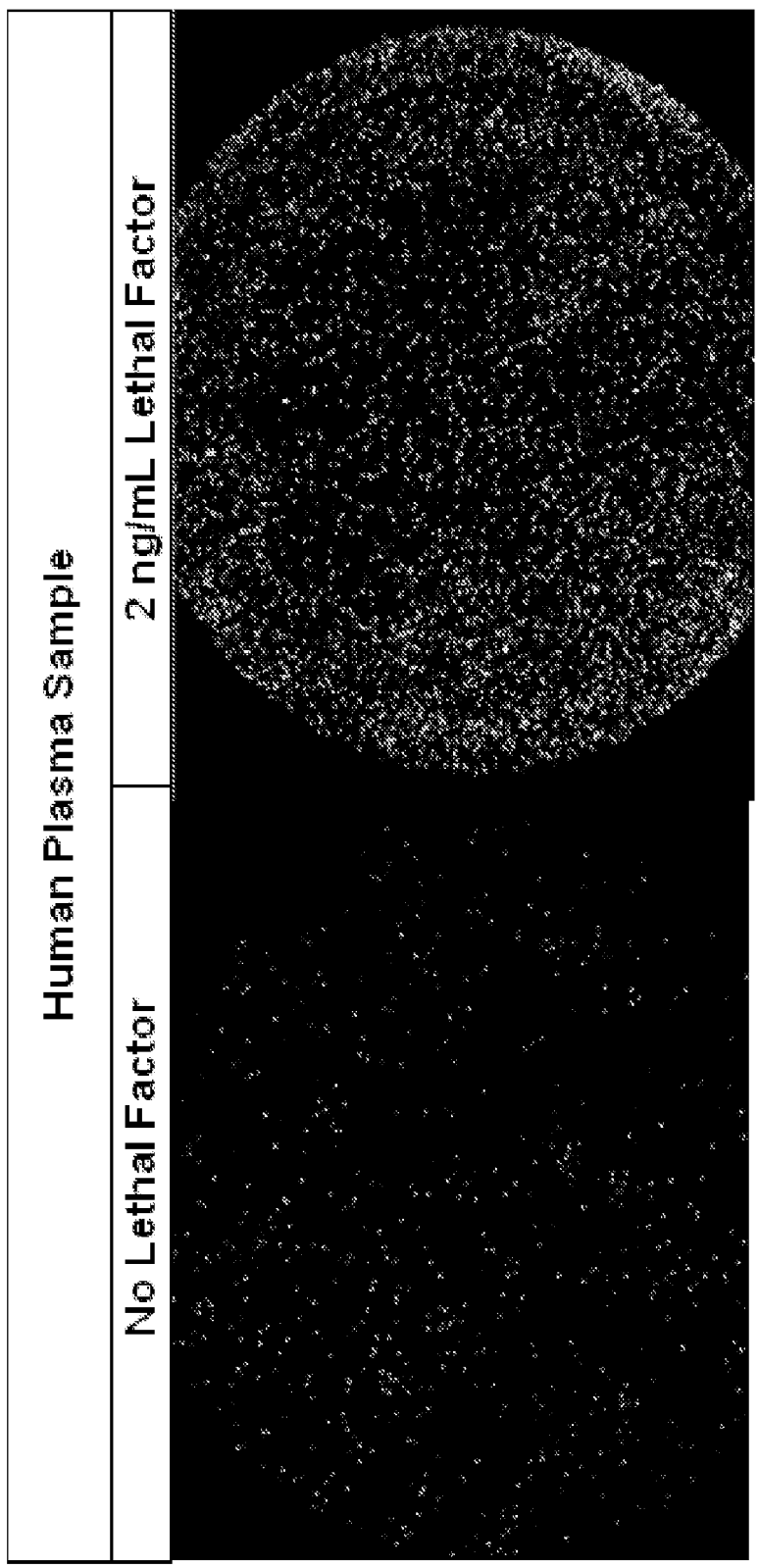
Fig. 18 Detection of *Bacillus anthracis* Lethal Factor (LF) in human plasma using magnetic capture and cushion dye re

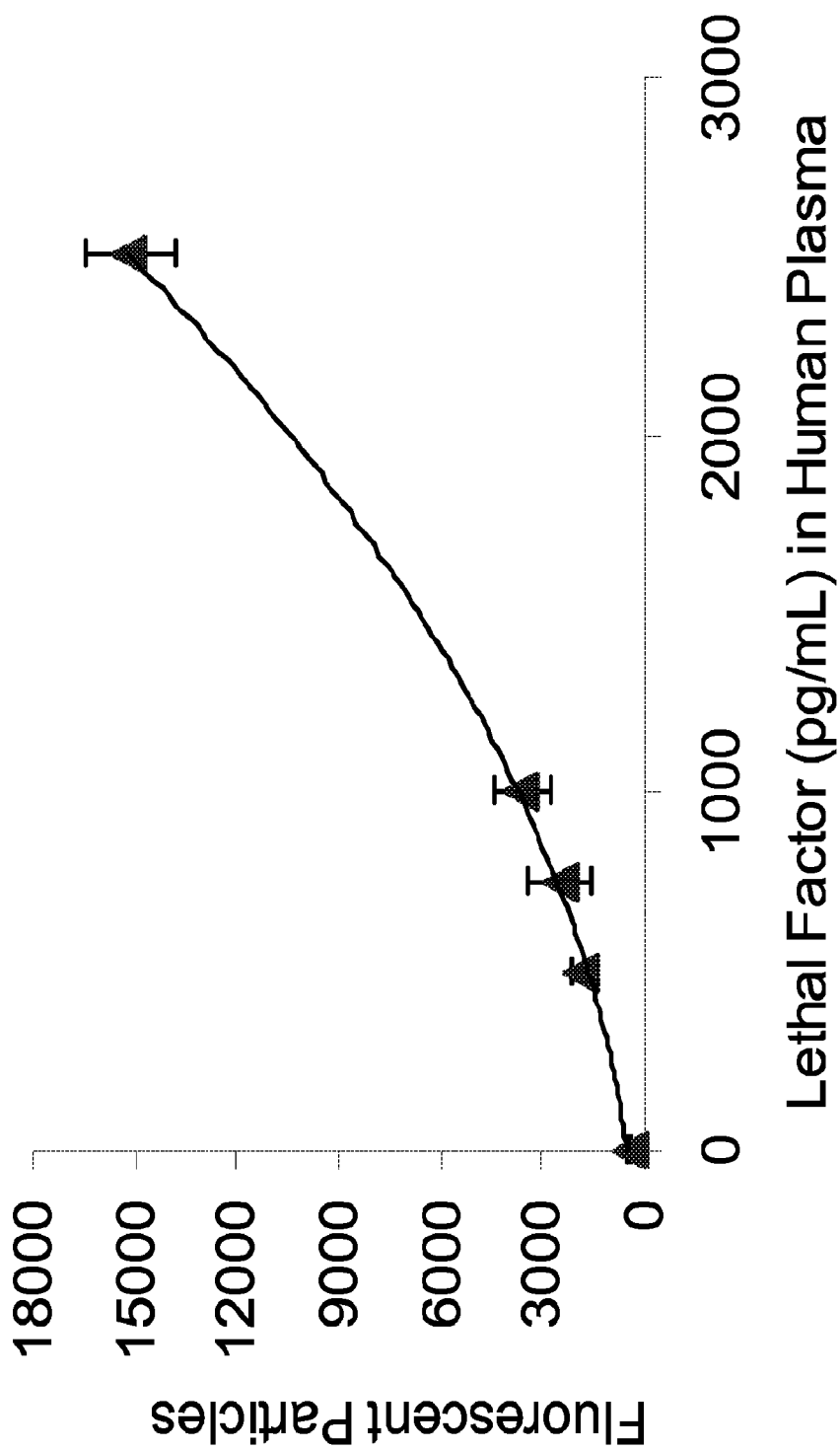
Fig. 19 Detection of *Bacillus anthracis* Lethal Factor (LF) in human plasma using magnetic capture and cushion dye reagent. (Example 10)

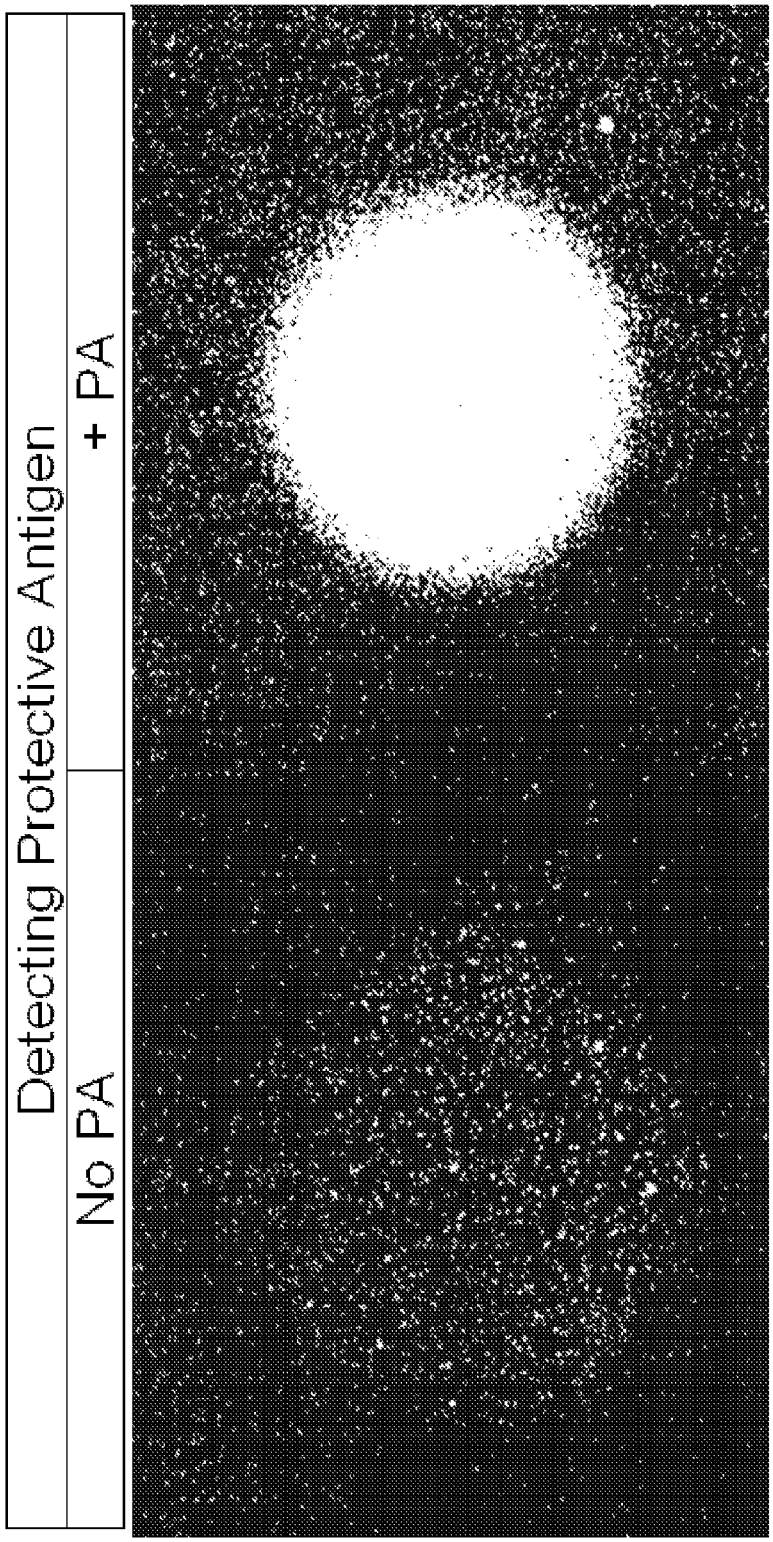
Fig. 20 Detection of *Bacillus anthracis* Protective Antigen (PA) in human plasma using magnetic capture and cushion dye reagent. (Example 11)

Fig. 21 Detection of *Bacillus anthracis* Protective Antigen (PA) in human plasma using magnetic capture and cushion dye reagent. (Example 11)

Fig. 22  Detection of *Bacillus anthracis* poly-D-γ-glutamic acid (PDGA) capsule polypeptide in human urine. (Example 12)

Fig. 23 Detection of *Bacillus anthracis* poly-D-γ-glutamic acid (PDGA) capsule polypeptide in human urine. (Example 12)

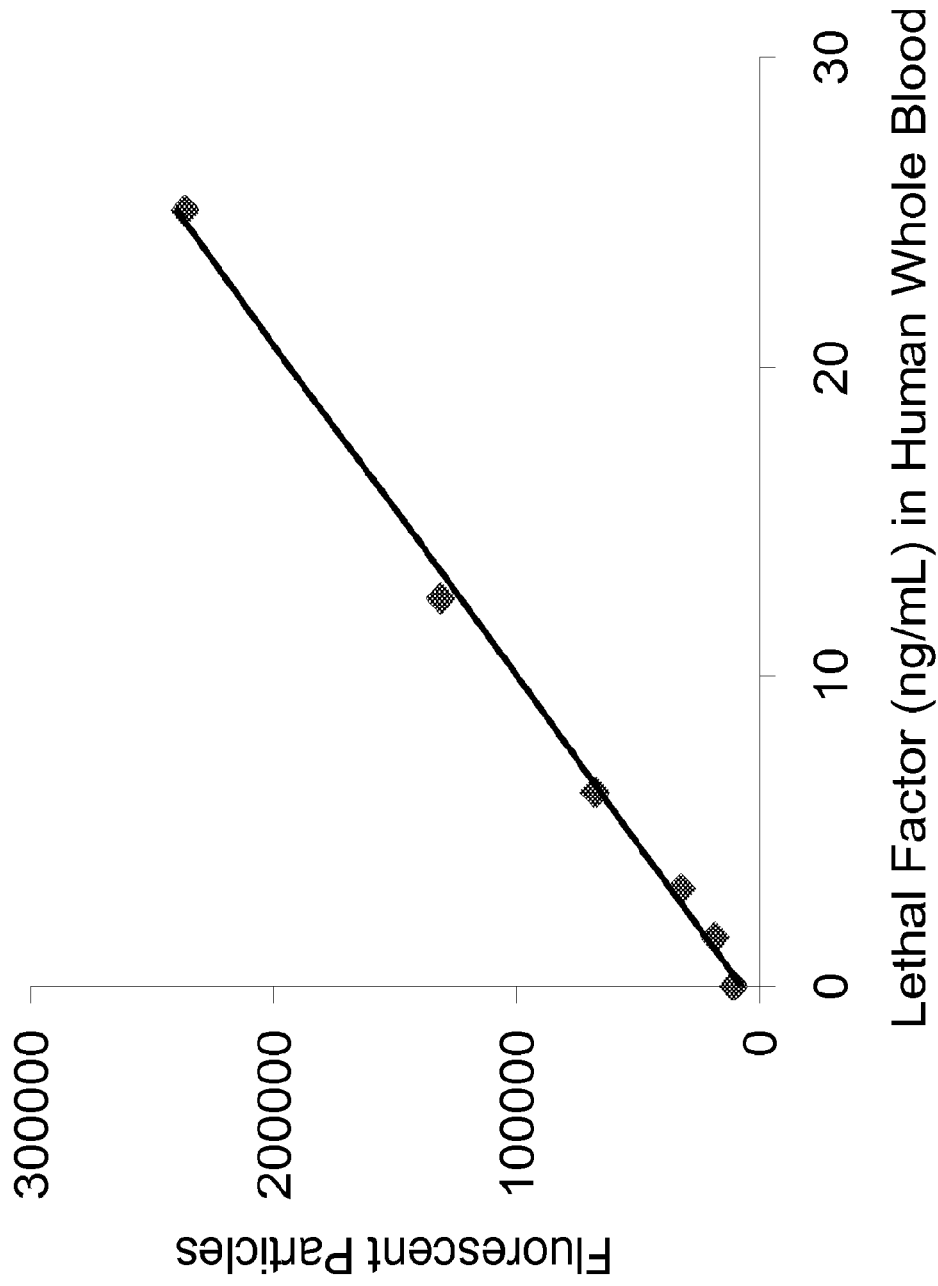
Fig. 24 Detection of *Bacillus anthracis* Lethal Factor in human whole blood by automated analysis. (Example 13)

Fig. 25  Competitive immunoassay for detection of *Bacillis anthracis* protein poly-D-γ-glutamic acid capsule polypeptide. (Example 14)

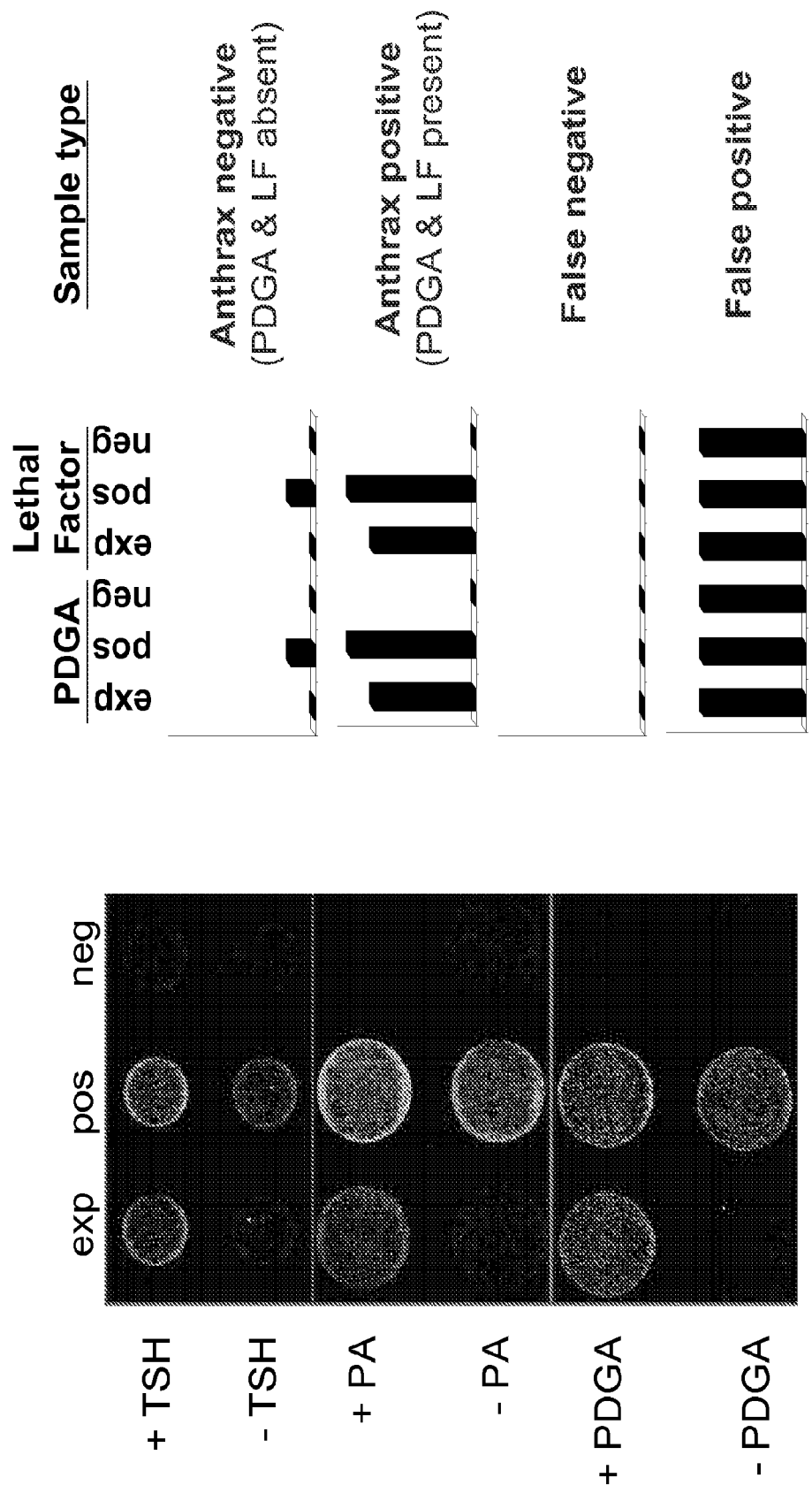
Fig. 26  Positive and negative internal assay controls for human TSH and *Bacillus anthracis* PA and PDGA. (Example 15)

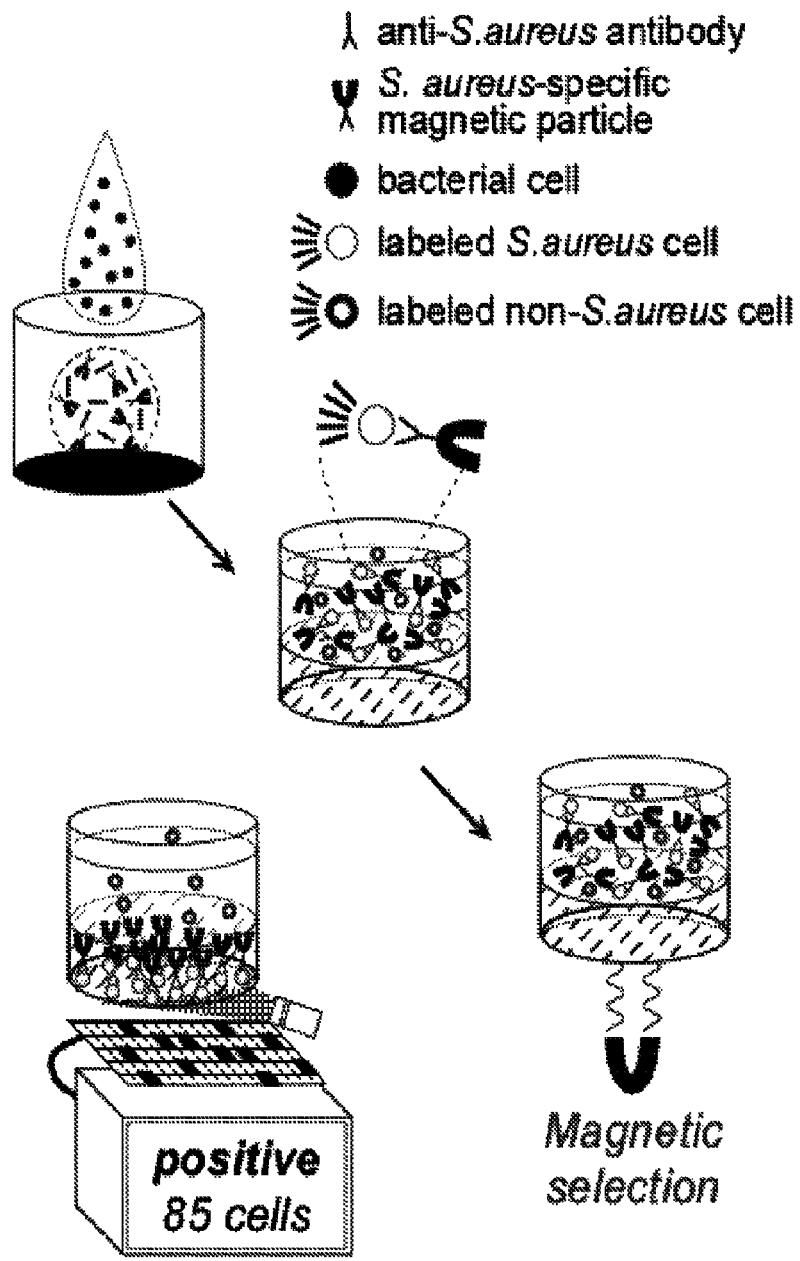
Fig. 27 Labeling of *Staphylococcus aureus* with Flourogenic DNA stain. The Multipath *S. aureus* assay counts individual labeled *S. aureus* cells using non-magnified digital imaging. The cell counting technology is the basis for determining antibiotic susceptibility by differential growth. (Example 16)

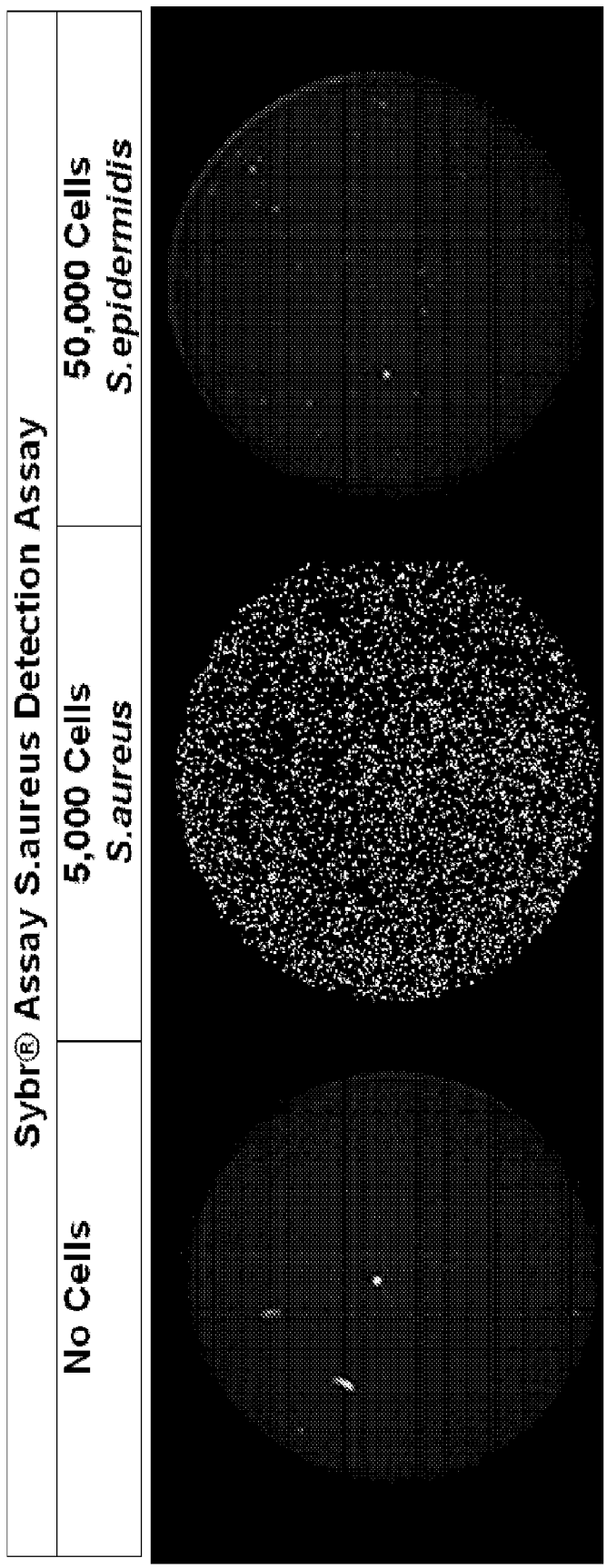
Fig. 28  Detection of *S. aureus* by detection with non-specific Sybr® Green DNA staining and Magnetic selection with dye cushion reagent. (Example 16)

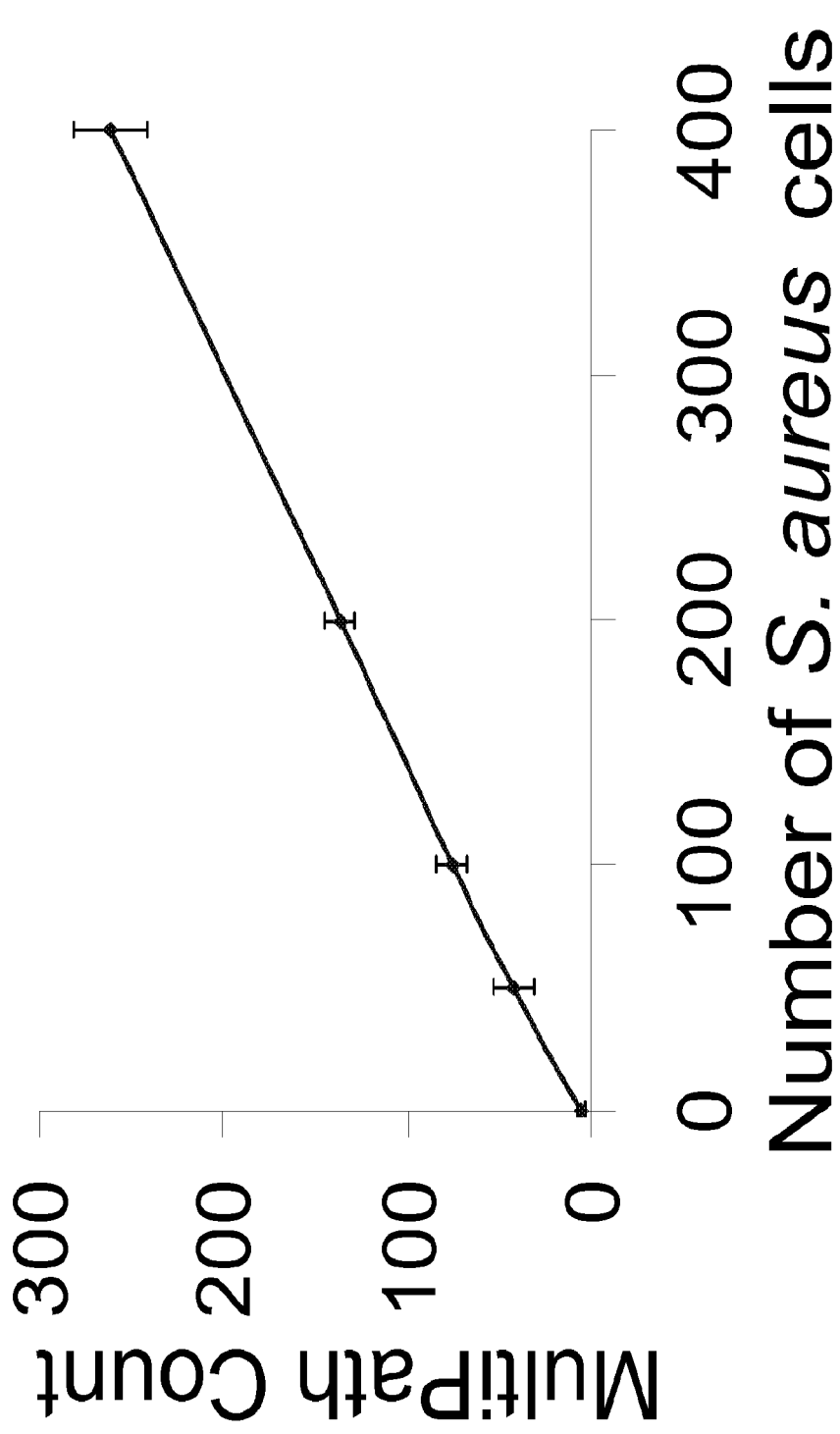
Fig. 29 Detection of *S. aureus* by detection with non-specific Sybr Green DNA staining and Magnetic selection with dye cushion reagent. (Example 16)

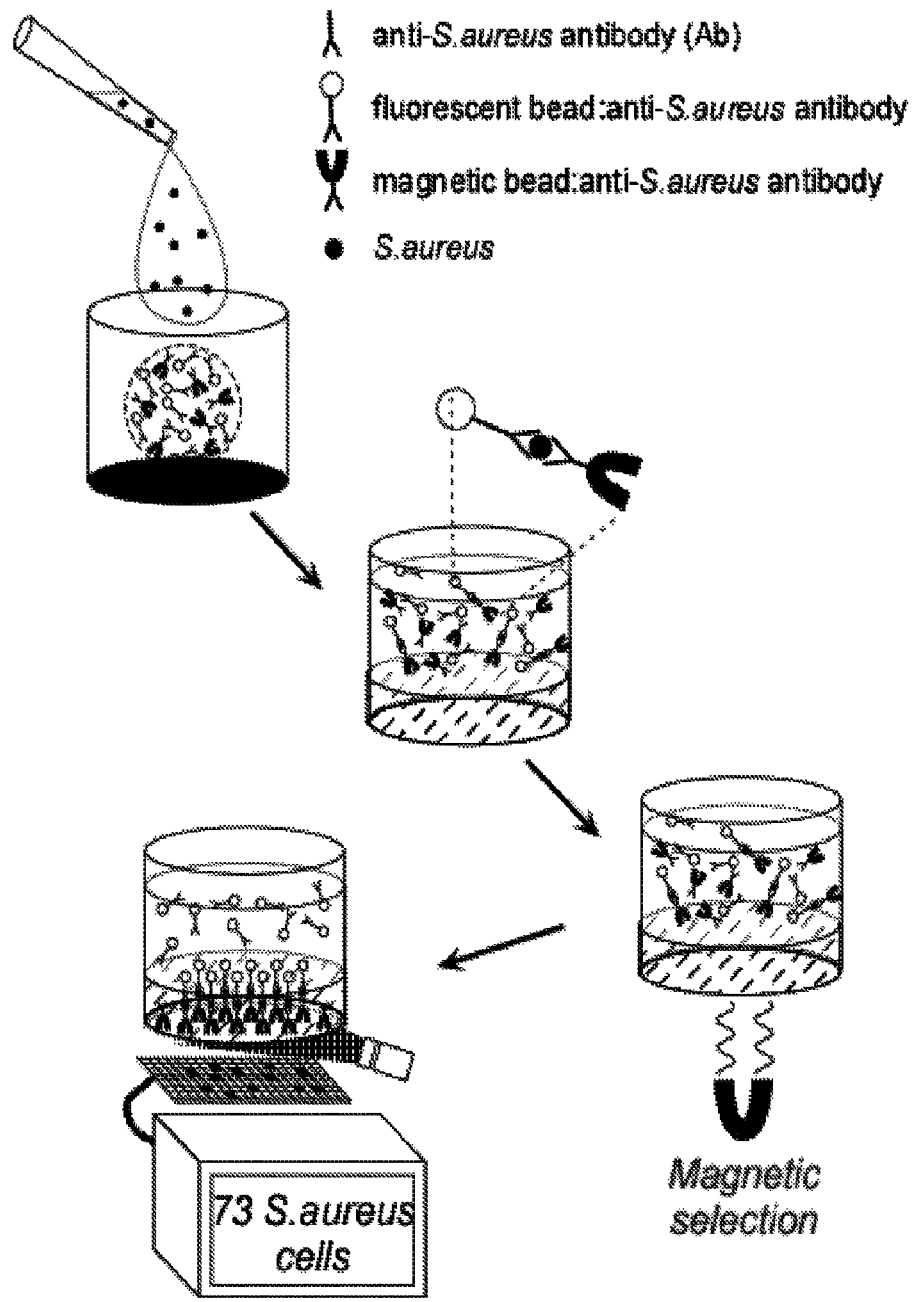
Fig. 30 Labeling of *Staphylococcus aureus* cells with chicken anti-protein A antibodies conjugated to fluorescent nanoparticles. (Example 17)

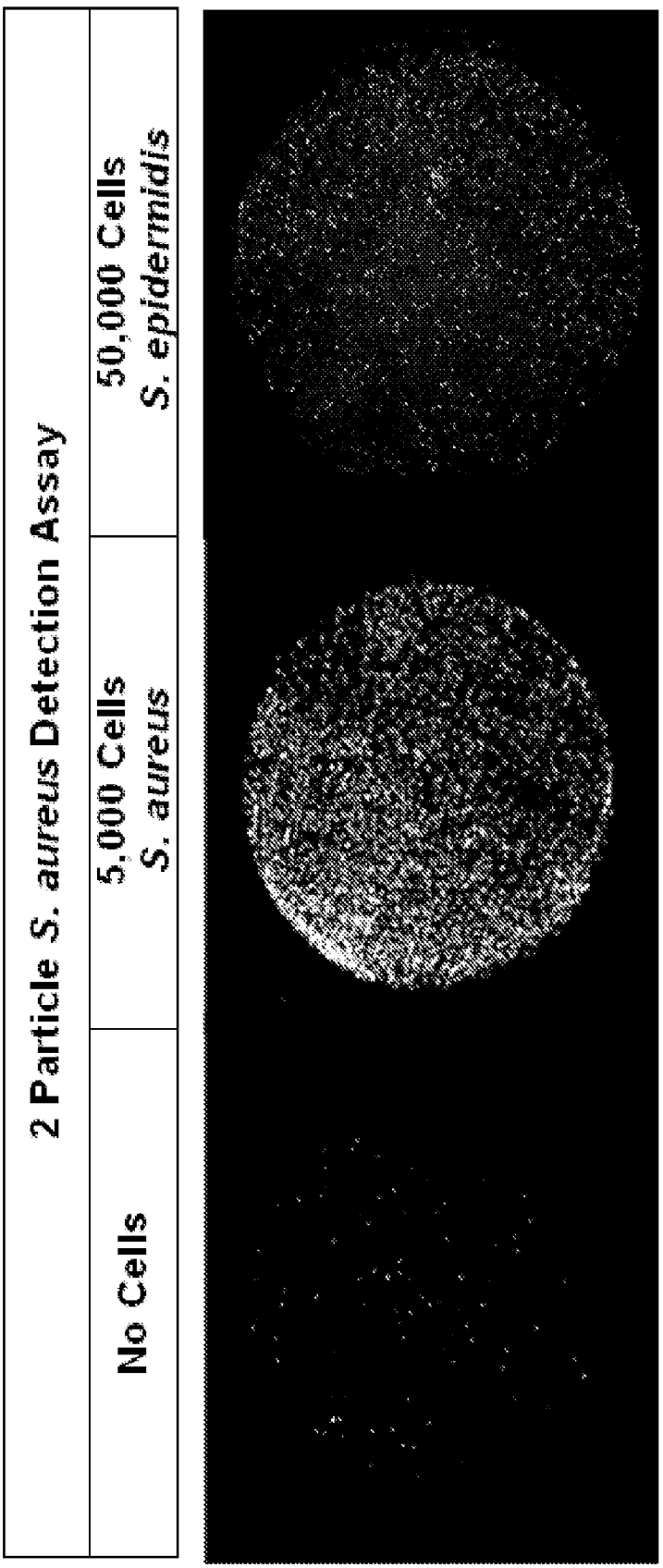
Fig. 31 Labeling of *Staphylococcus aureus* cells with chicken anti-protein A antibodies conjugated to fluorescent nanoparticles. (Example 17)

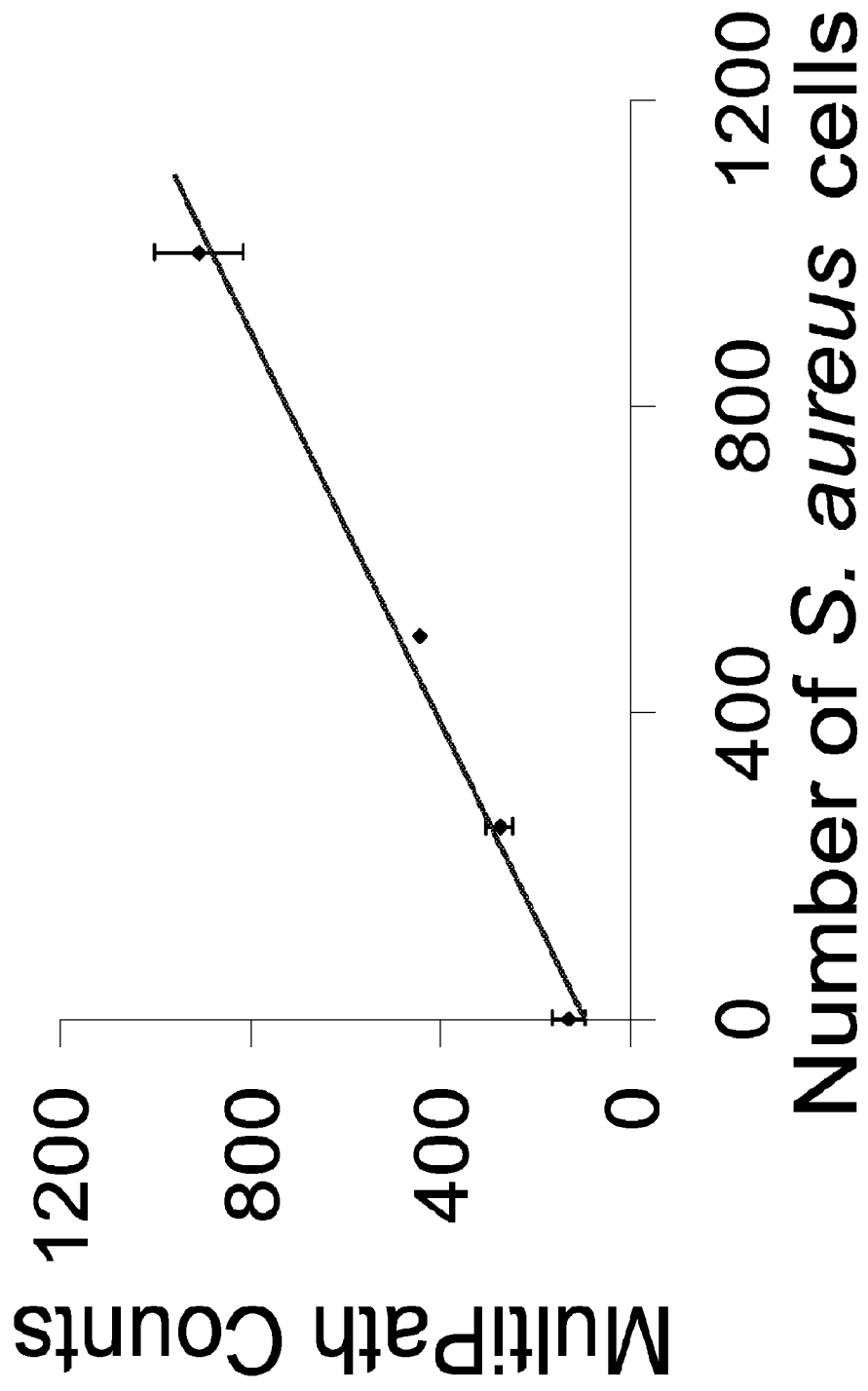
Fig. 32  Detection of S. aureus cells by detection with chicken anti-Protein A antibododies conjugated to Fluorescent Particles and Magnetic selection with dye cushion reagents. (Example 17)

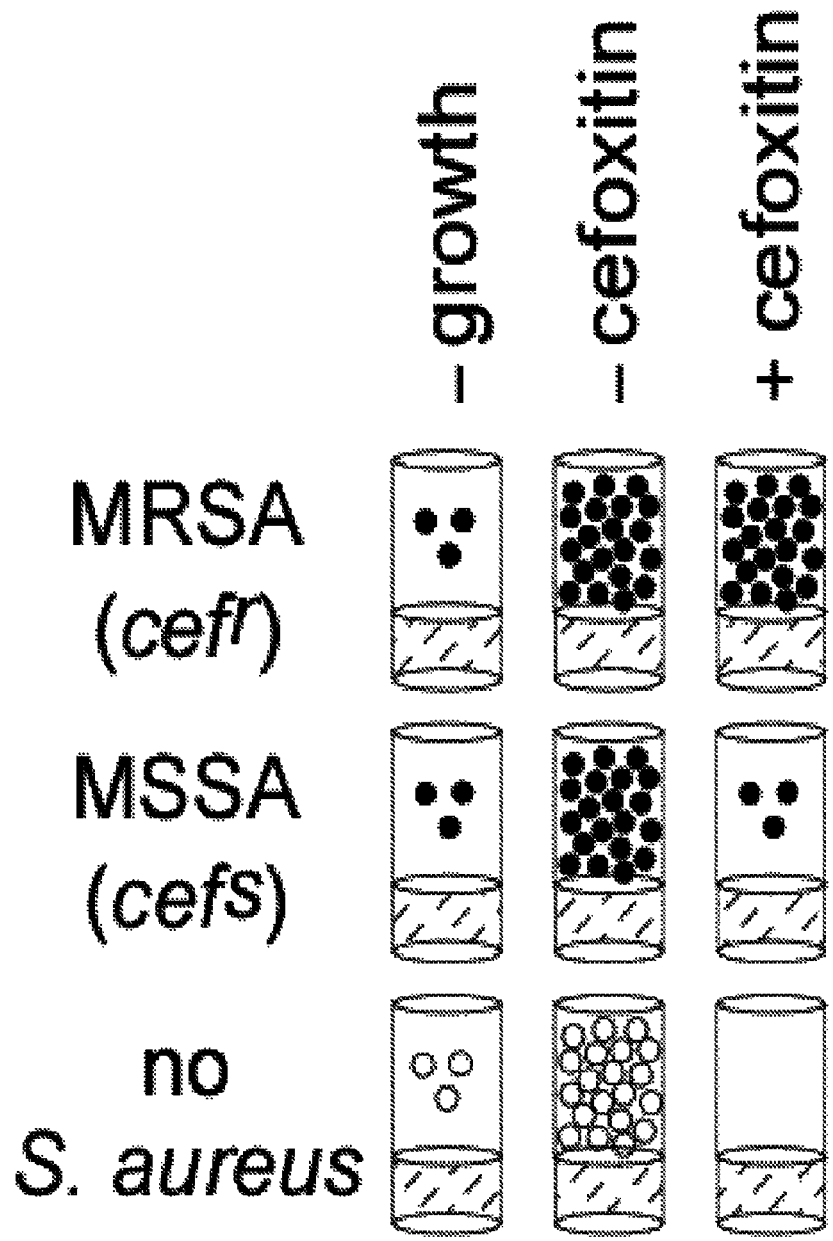
Fig. 33 Protocol for detection of methicillin resistant
S.aureus (MRSA) through selective growth and
immunodetection of cells. (Example 18)

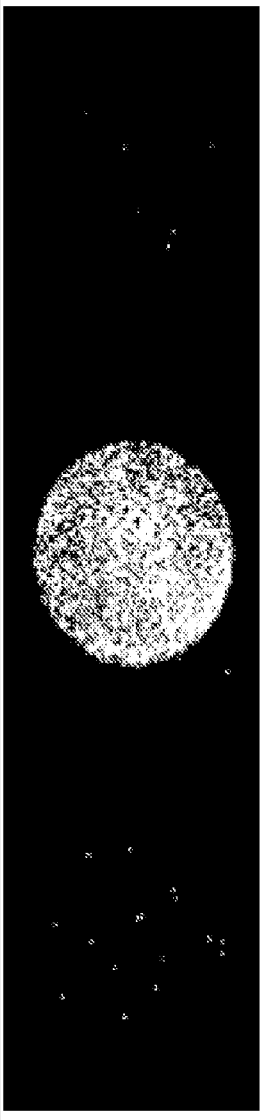
Fig. 34  Detection of methicillin resistant S.aureus (MRSA) through selective growth and immunodetection of cells. (Example 18)

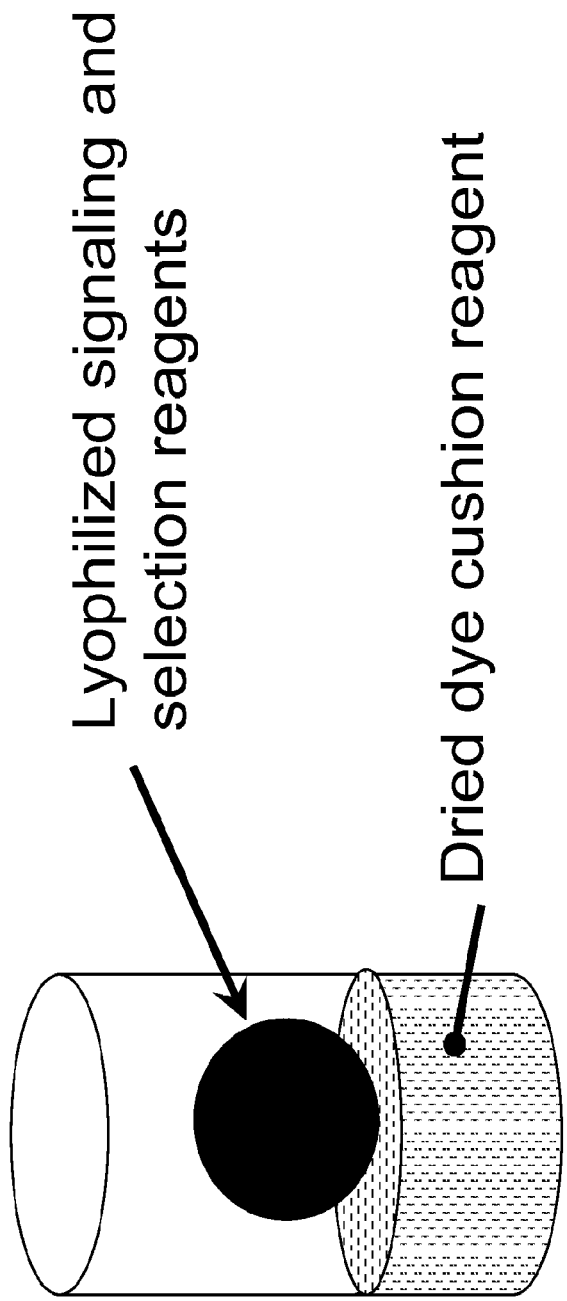
Fig. 35   Stabilization of Reagents-Lyophilization of human Thyroid Stimulating Hormone reagents. (Example 19)

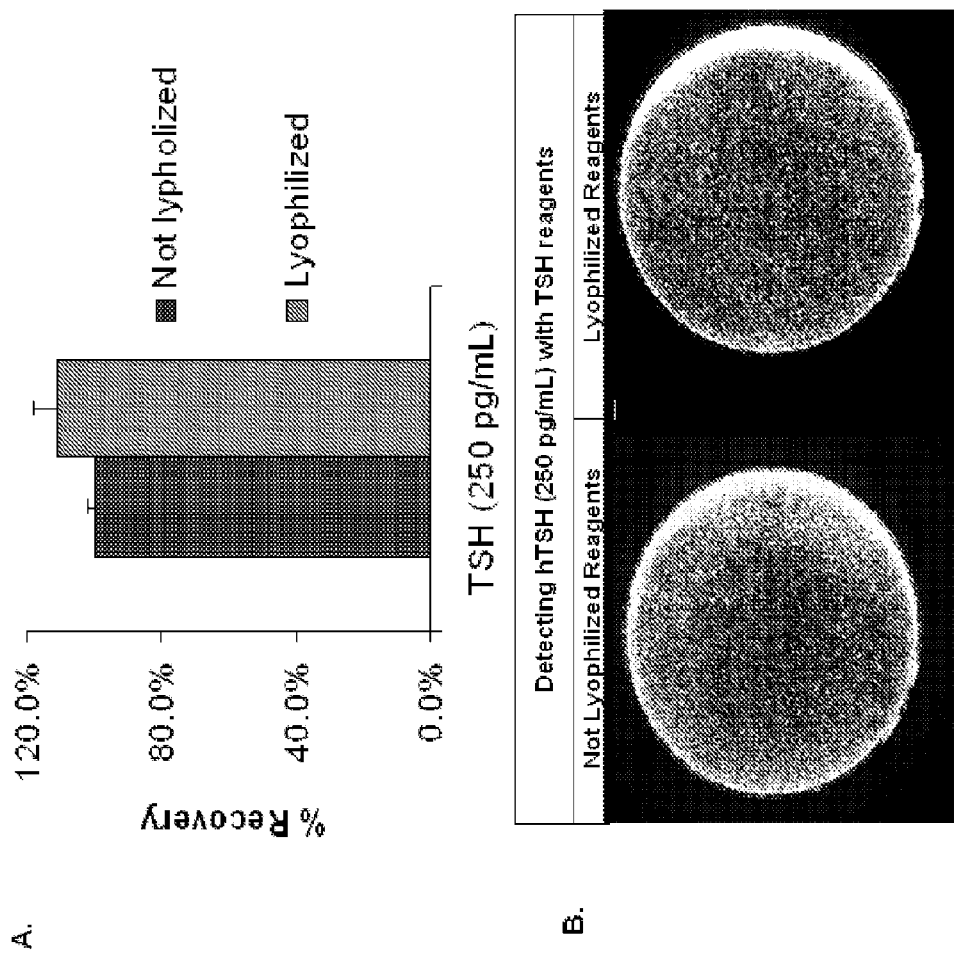
Fig. 36 Assay of human Thyroid Stimulating Hormone utilizing lyophilized reagents. (Example 19)

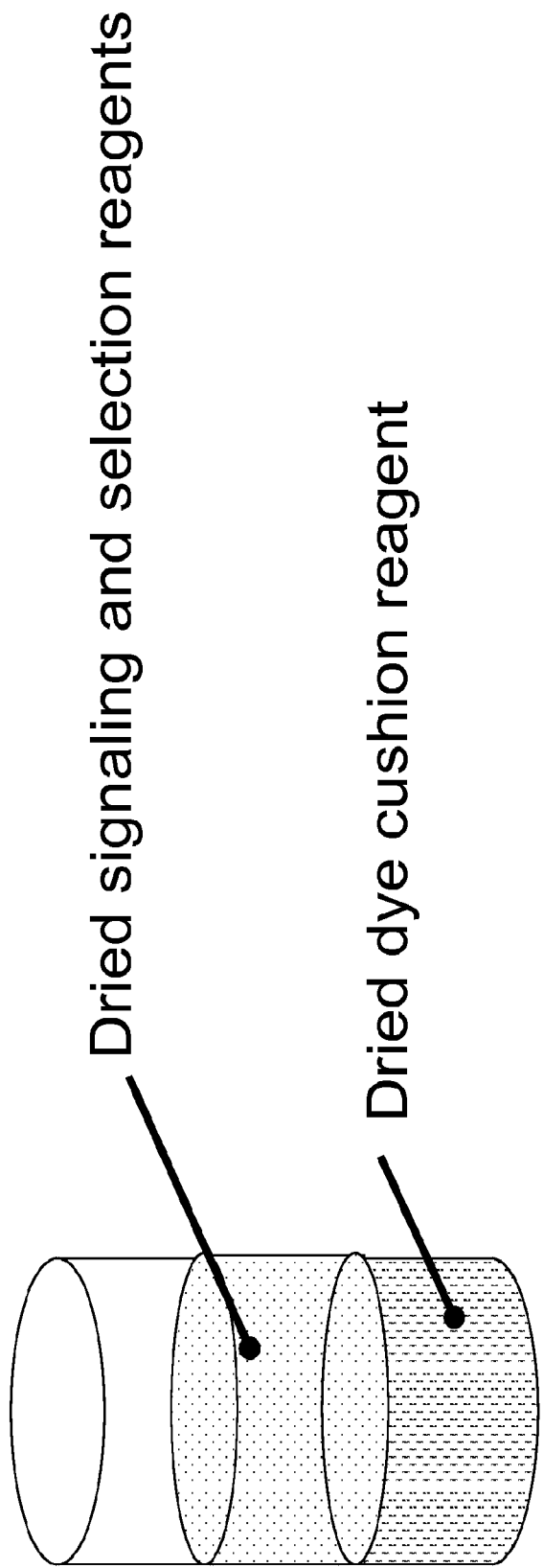
Fig. 37  Stabilization of reagents-Lyophilization of Methicillin resistant *S. aureus* reagents. (Example 20)

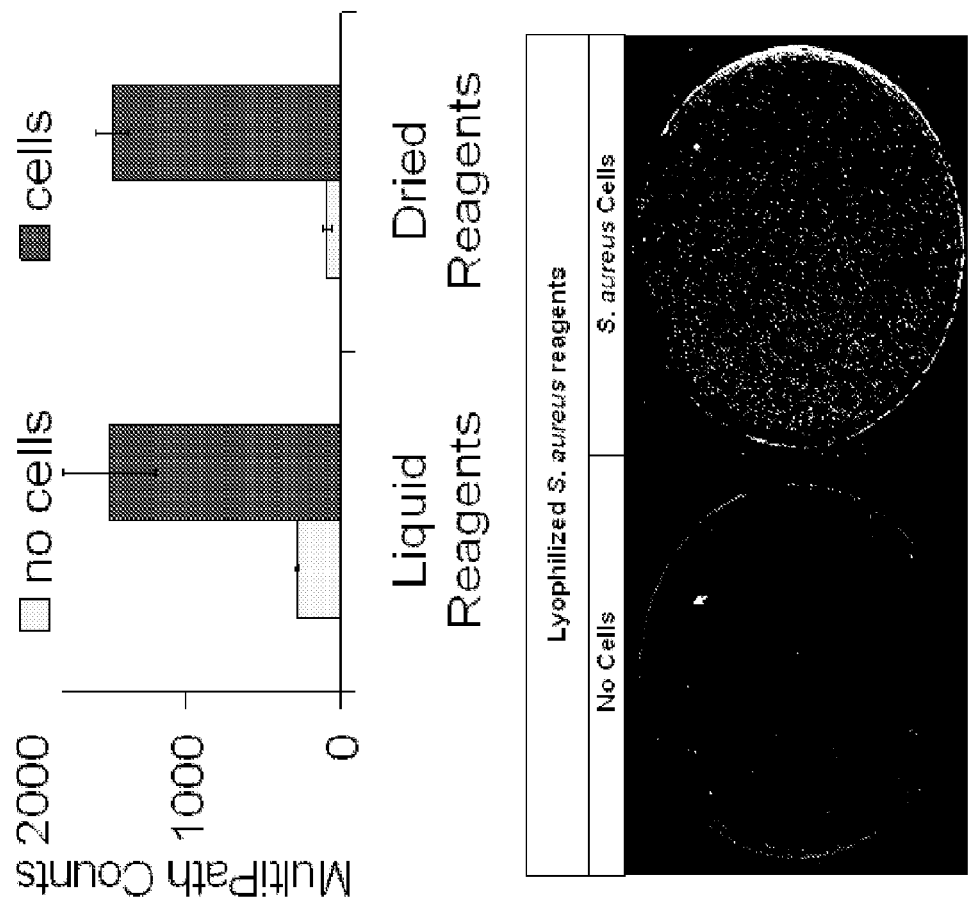
Fig. 38 Assay for *S. aureus* utilizing lyophilized reagents. (Example 20)

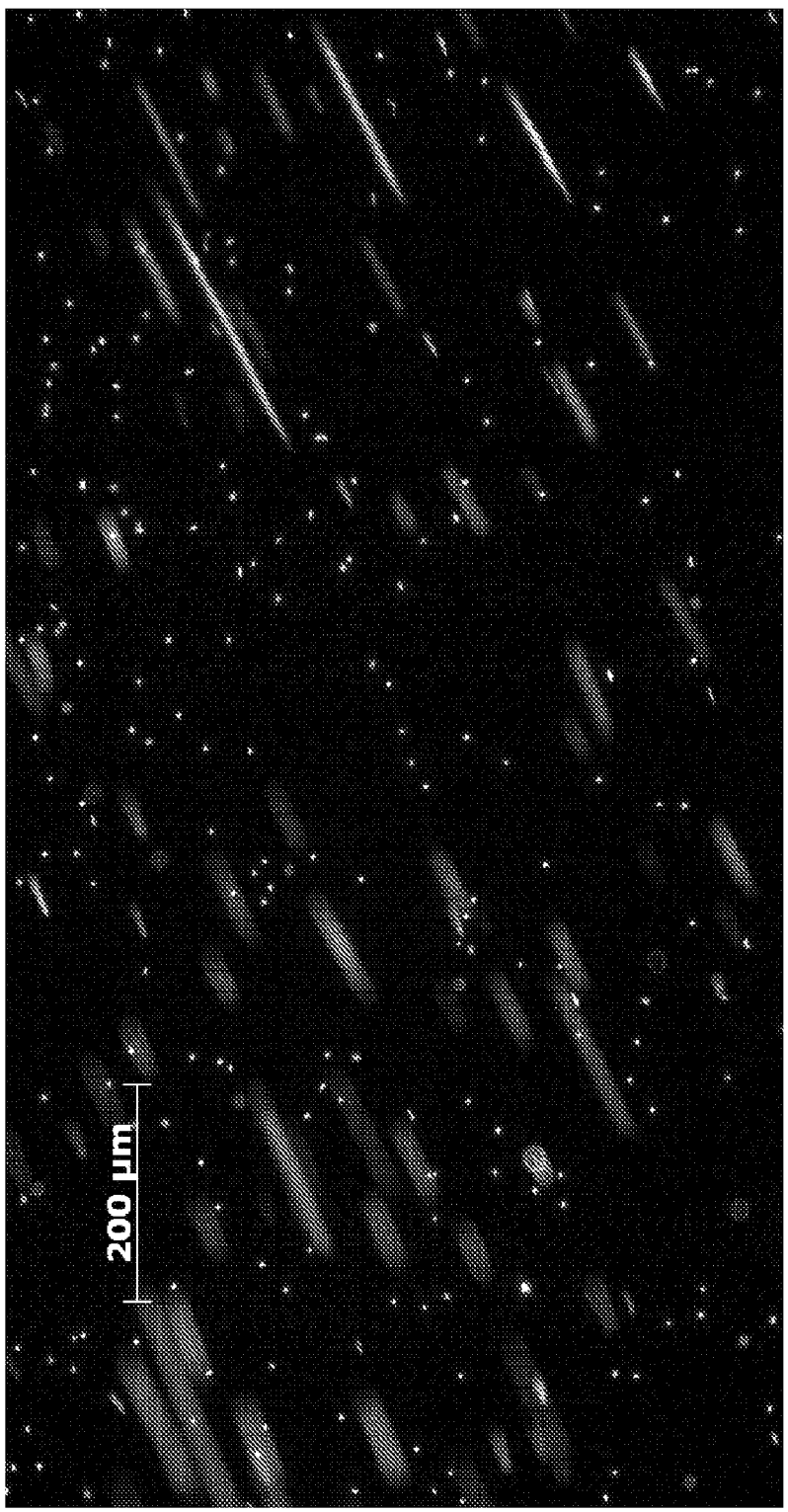
Fig. 39  Specific detection of biotin by movement of the selected complexes. (Example 21)

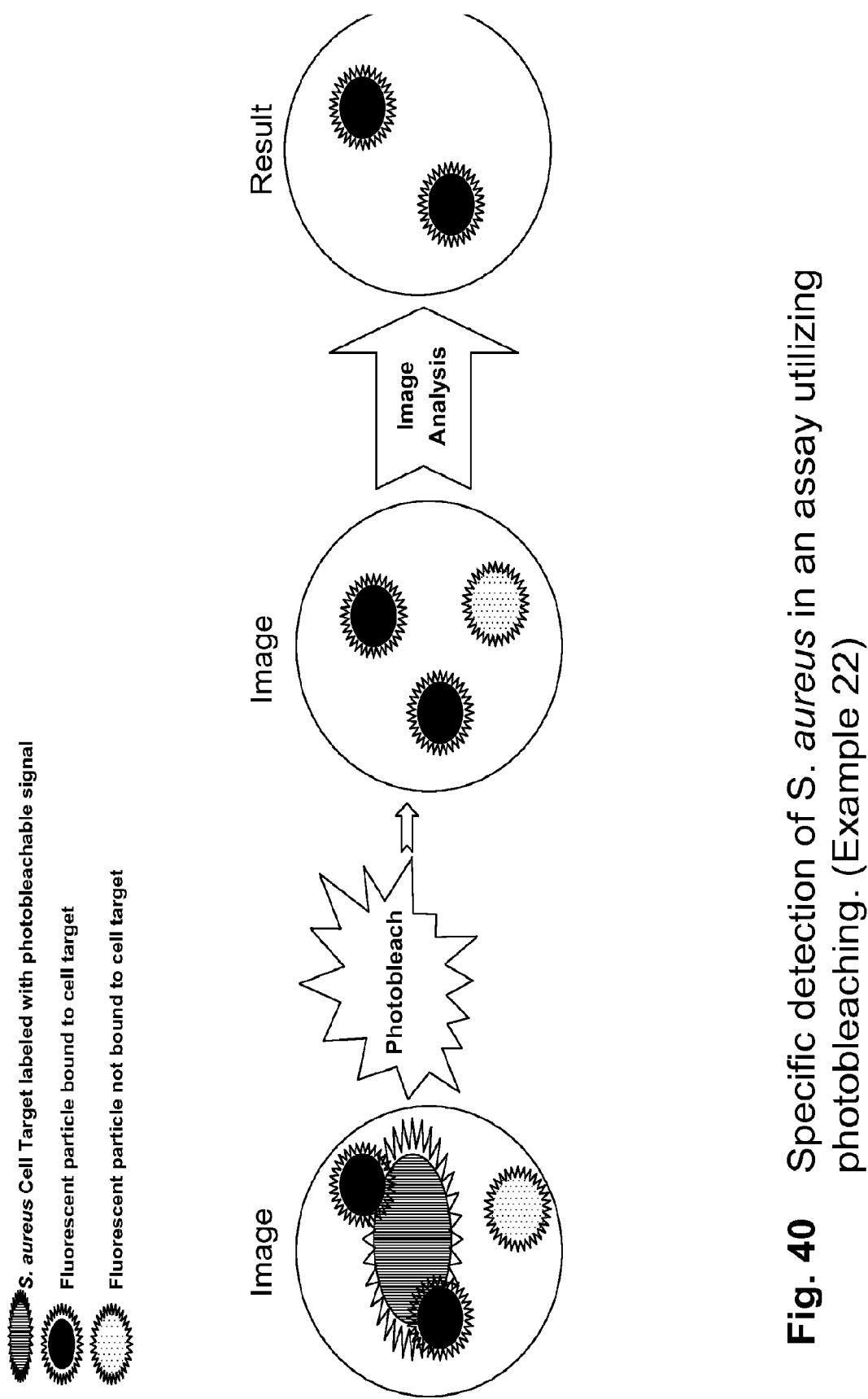
Fig. 40  Specific detection of *S. aureus* in an assay utilizing photobleaching. (Example 22)

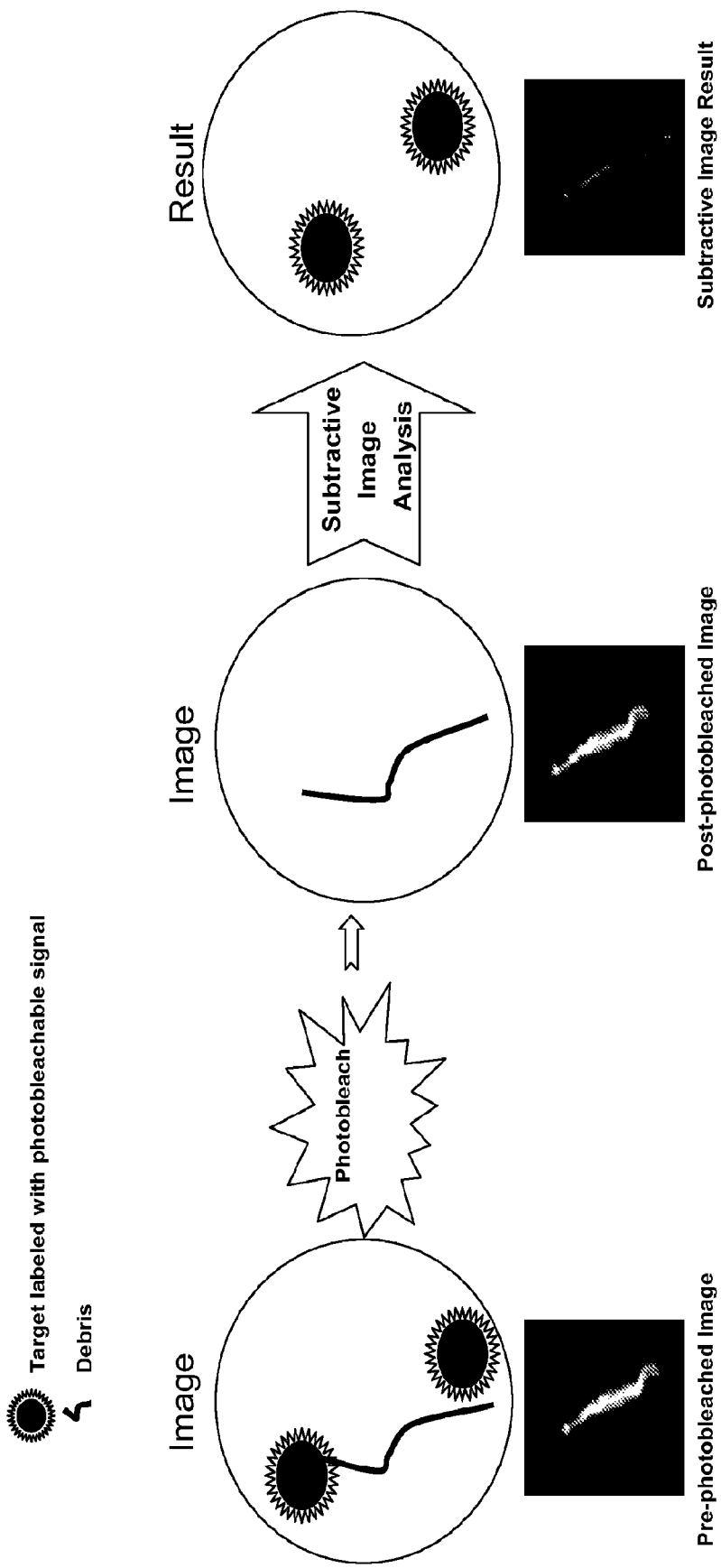
Fig. 41  Use of photobleaching to identify debris in an image where the label is susceptible to photobleaching. (Example 23)

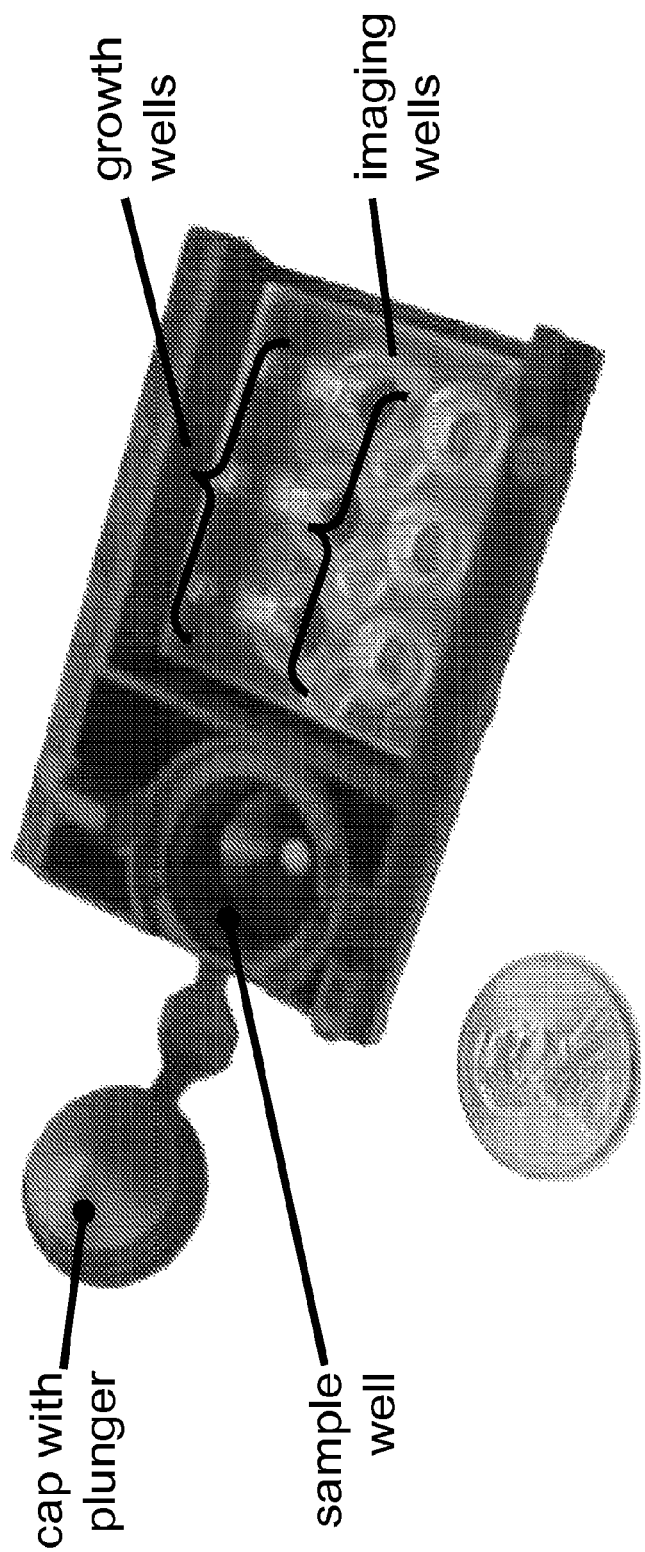
Fig. 42 Cartridge embodiment. (Example 9)

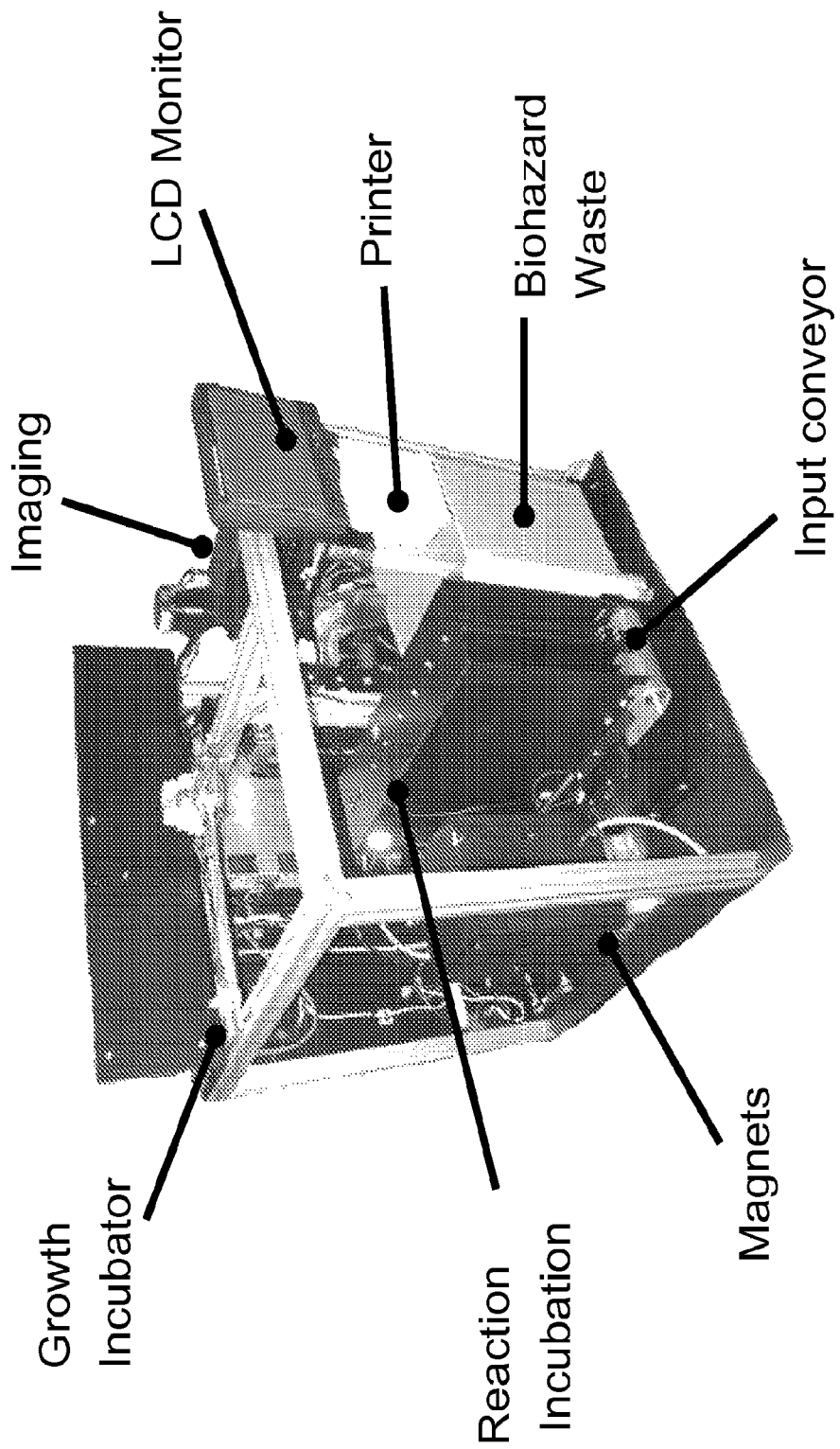
Fig. 43   Analyzer photograph (Example 14)

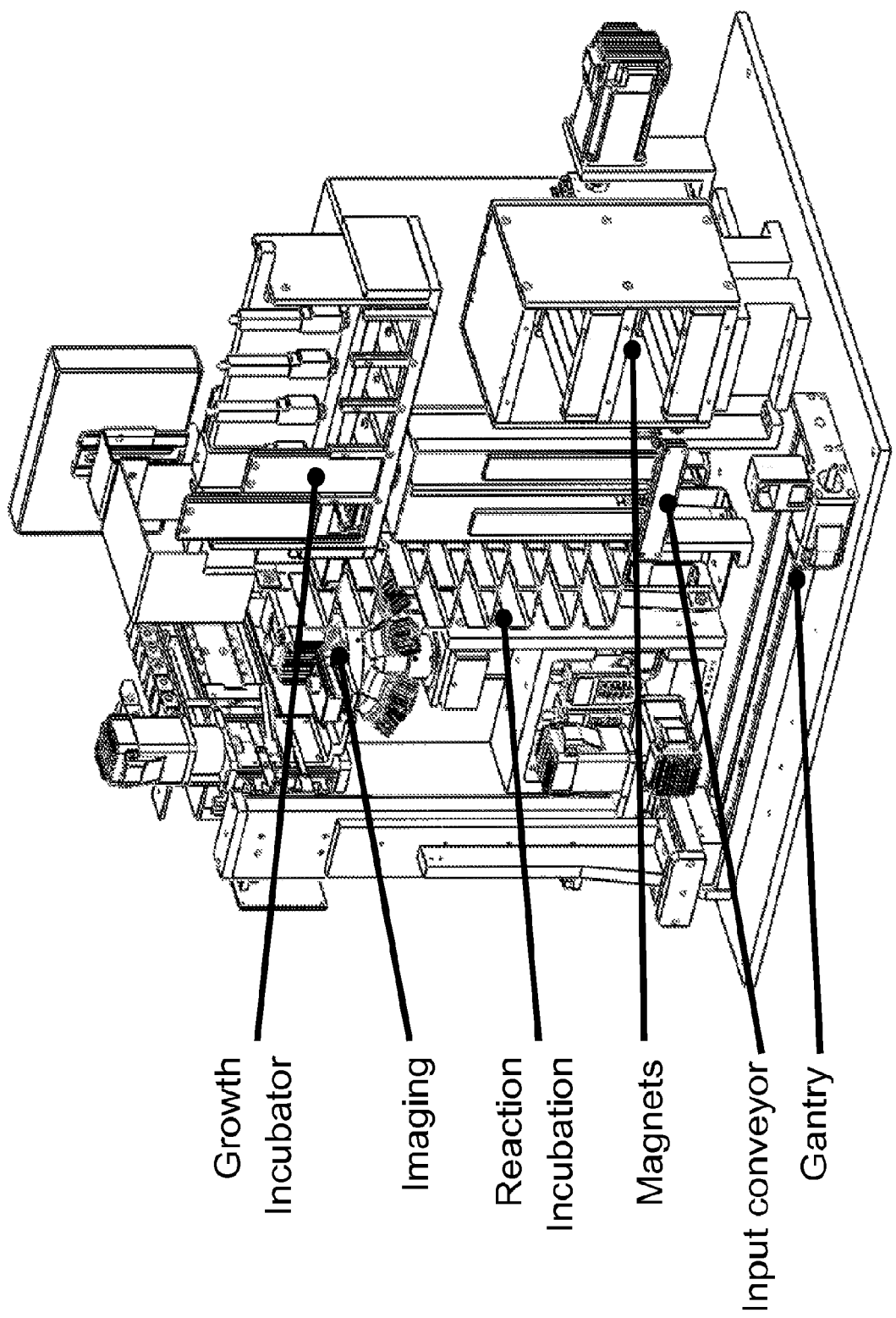
Fig. 44  Analyzer CAD Subassemblies (Example 14)

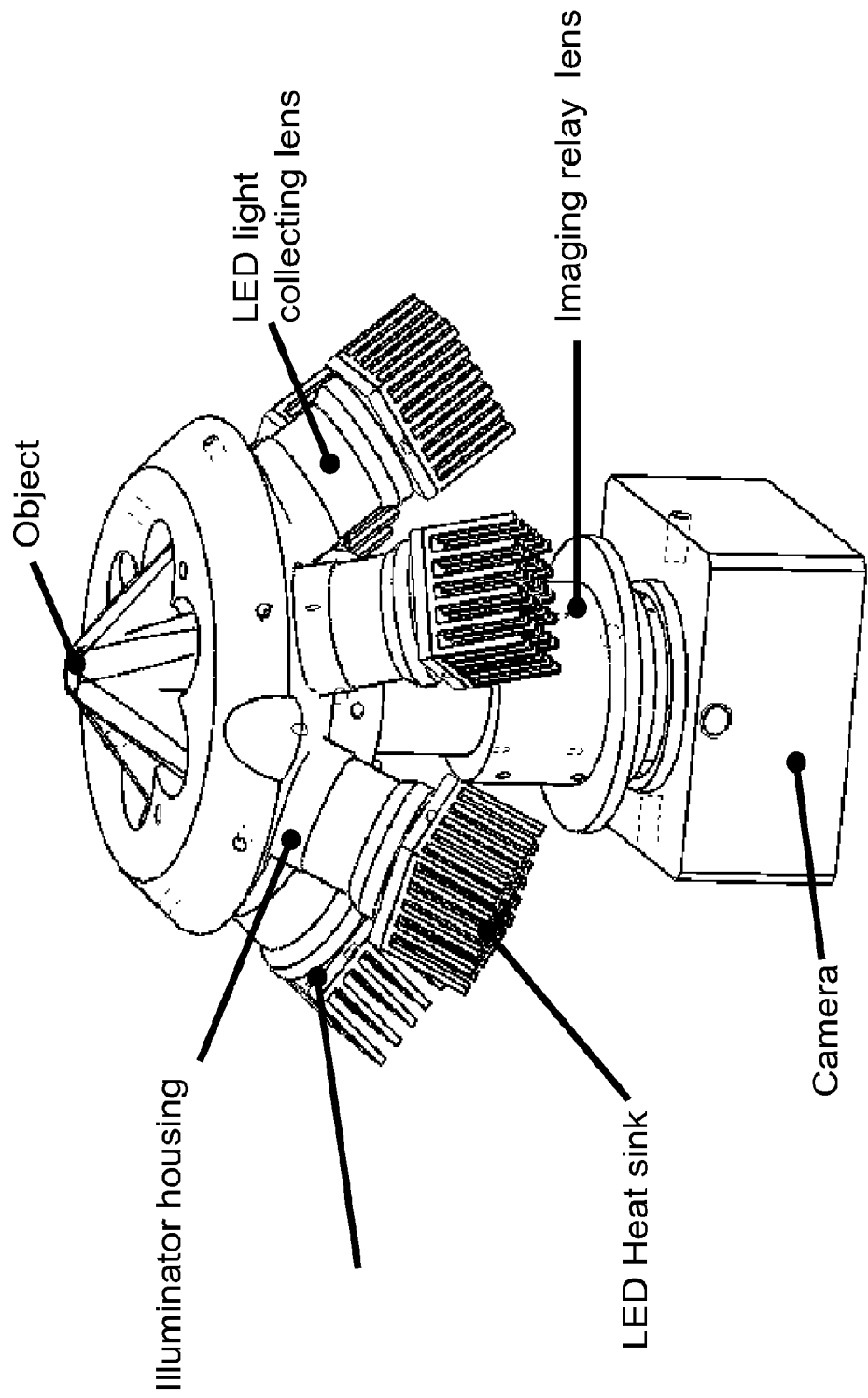
Fig. 45  Imaging optics system diagram of automated analyzer with robotics. (Example 1 and Example 9)

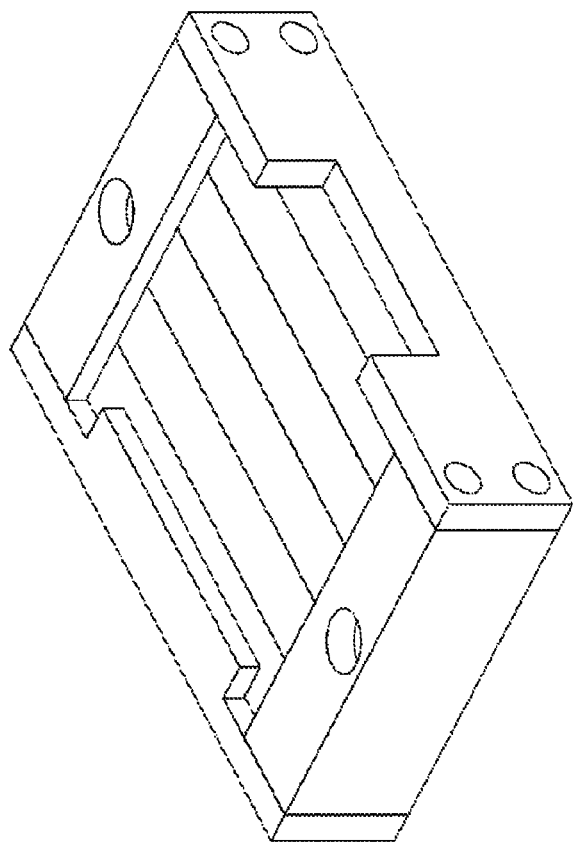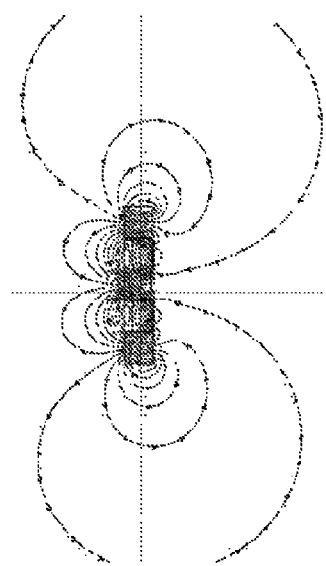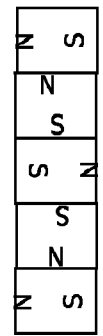
Fig. 46 Bar magnetic assembly. (Example 2)

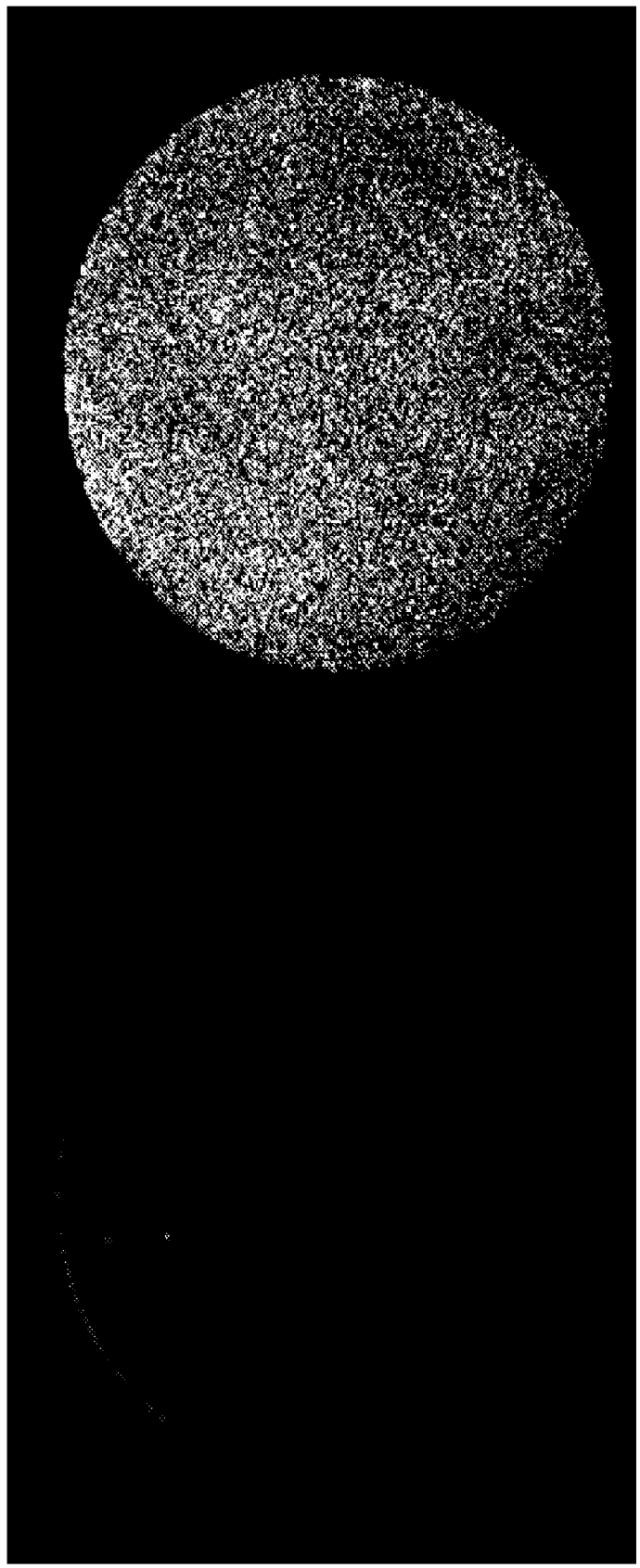
Fig. 47 Detection of individual labeled S. aureus cells complexed with magnetic particles in a cartridge containing a dye cushion on an automated analyzer.

METHOD FOR DETECTING ANALYTES

CROSS-REFERENCE TO RELATED APPLICATIONS

This application claims benefit of U.S. Provisional Application No. 61/099,830, filed Sep. 24, 2008, which is hereby incorporated by reference.

BACKGROUND

Importance of detecting specific targets. Methods for detecting specific molecular, cellular, and viral targets are fundamental tools for medical and veterinary diagnostics, environmental testing, and industrial quality control. Examples of methods for detecting specific targets in clinical medicine include over-the-counter rapid pregnancy tests, microbiological culture tests for determining the resistance of infectious agents to specific antibiotics, and highly automated tests for cancer markers in blood samples. Detecting pathogen contaminants in food, high throughput screening of candidate compounds for drug discovery, and quantifying active ingredients in pharmaceuticals exemplify industrial manufacturing applications that depend on methods for determining the presence of specific targets. Environmental applications requiring testing for specific targets include detecting water supply contamination, airborne biothreat agents, and household fungal contaminants.

Desirable attributes of methods for detecting specific targets. Methods for detecting specific targets should be accurate, that is they should be sensitive and specific. The methods should be sensitive enough to detect the target when it is present in significant amounts. And they should be specific; they should not indicate the presence of the target when it is not present in significant amounts. Other beneficial attributes include breadth of potential target analytes, rapid results, ease-of-use, cost-effectiveness, target quantification, and automation. The importance of the various desirable attributes can depend on the particular application and testing venue.

Breadth of targets. Testing methods should be capable of detecting a wide range of specific targets. Representative target classes include human cells (e.g., CD4+ cells in HIV/AIDS diagnostics), bacterial cells (e.g., Methicillin Resistant *Staphylococcus Aureus* or MRSA or *E. coli*), viruses (e.g., Hepatitis C virus), prions (e.g., Bovine spongiform encephalopathy agent, the cause of "mad cow" disease), macromolecules (e.g., proteins, DNA, RNA, carbohydrates), and small molecules (e.g., chemotherapeutic drugs, lipids, sugars, amino acids, nucleotides), Labeling specific targets. One important approach for detecting specific cells, viruses, or molecules is to tag the targets with optically detectable labels that bind specifically to the target. Target-specific labels can have various types of target binding moieties including macromolecules (e.g., antibodies, protein receptors, nucleic acids, carbohydrates, and lectins) and small molecules (e.g., hormones, drugs of abuse, metabolites). The detectable signaling moieties of the target-specific labels can use a variety of signaling modes including fluorescence, phosphorescence, chromogenicity, chemiluminescence, light-scattering, and Raman scattering.

Methods for determining the presence of specifically labeled targets. A variety of methodologies have been developed for testing samples for the presence of specifically labeled target molecules, cells, and viruses. The technologies differ in the types of samples accommodated, mode of binding of the label to the target, type of signal delivered by the label, plurality of labeled targets detected, method for distinguishing bound from unbound labels, and technology for detecting the specifically labeled targets.

Which method is used depends on the type of analyte to be detected, testing venue, degree of automation required, clinically relevant concentration range, skill of the operator, and price sensitivity. For example immunoassays use target-specific antibodies for detection. To make them optically detectable, antibodies can be attached to signaling moieties including radioactive isotopes, fluorescent molecules, chemiluminescent molecules, enzymes producing colored products, particles dyed with fluorescent compounds, resonance light scattering particles, or quantum dots. Antibody-based technologies include manual lateral flow, ELISA, flow cytometry, direct fluorescence immunoassays, western blots, and highly automated central laboratory methods. Similarly, detection of specific nucleic acid sequences can use complementary nucleic acid probes associated with a variety of types of signal moieties using methods that include nucleic acid amplification, Southern and Northern blots, and in situ hybridization.

Using imaging to count labeled targets. Imaging is a powerful method for detecting specifically selected labeled targets on a detection surface. Imaging methods map the optical signal emanating from each point in the detection area to a corresponding point in the image. In contrast, non-imaging detection methods generally integrate the optical signal emanating from the entire detection area.

Some imaging methods can detect and count individual labeled target molecules. Enumerating specifically labeled target molecules can result in detection at very low target levels compared to detection area integration methods. The sensitivity advantage of imaged-based target counting methods stems chiefly from the fact that the optical signal to background stays essentially constant as target levels decrease. In contrast, for detection area integration methods the signal to background decreases as the target levels decrease. One type of method builds an image by systematically scanning the detection area with a microscopic beam. Scanning methods are more time consuming than methods that use digital array detectors (e.g., CCD or CMOS cameras) to simultaneously enumerate specifically labeled targets in the entire detection area.

Large area imaging at low magnification for sensitive target counting. Some methods use high magnification microscopy to enumerate the individual microscopic targets. Microscopic imaging lacks sensitivity because each image only samples a small area. Larger areas can be successively imaged but acquisition of many images can be laborious, expensive and time consuming. Alternatively, labeled microscopic targets can be individually detected and enumerated using large area imaging at low magnification. Low magnification imaging can enumerate a small number of microscopic targets in a relatively large area in a single image.

Some methods that use large area automated digital imaging have been developed for simultaneously detecting individual labeled targets. These methods generally detect labeled targets in a capillary chamber and use lateral flow to remove unbound label. As for other lateral flow methods, this technical approach complicates automation and limits the volume of sample that can be conveniently analyzed.

Using selection to isolate specifically labeled target from free label and other labeled entities. To detect specifically labeled targets methods generally must remove or distinguish unbound label and other labeled entities from the bound label. One common approach uses physical selection of the labeled target complexes after which the free labeled can be removed by repeated washing. This approach, while effective, generally requires labor for manual methods or sophisticated liquid handling engineering for automated systems.

Selection of labeled target complexes can be mediated by physical capture on a surface coated with a binding moiety specific for the target (e.g., capture antibodies in ELISA or lateral flow assays or DNA probes in microarray assays). Similarly, separating labeled target complexes from free label can be done by using selection particles coated with target-binding moieties. For example, magnetic selection can be used to select labeled target complexes bound to target-specific magnetic particles during wash steps that remove free label.

Lateral flow methods can simplify the washing process to some extent by using capillary flow to wash free label from labeled targets that are selected by capture on a surface. This type of washing may require an addition of a wash solution as an extra user step. Lateral flow methods are not very sensitive and not generally amenable image analysis, automation, or high throughput.

Methods that do not require washing to remove free label from specifically labeled targets. Several methods have been developed that detect targets specifically complexed with labeled target-specific binding moieties. One type of method uses labels that do not emit signal unless they are bound to the target molecules. These labels have the limitation that they do not emit a strong enough signal for efficient large area detection of individual labeled targets. Another method that does not require washes uses selection through a liquid phase barrier to separate labeled target complexes from unbound label. This approach uses detection area integration rather than sensitive image analysis and thus lacks high sensitivity.

SUMMARY OF THE INVENTION

The invention provides an improved method for sensitive and specific detection of target molecules, cells, or viruses. The inventive method uses large area imaging to detect individual labeled targets complexed with a target-specific selection moiety. The invention eliminates wash steps through the use of target-specific selection through one or more liquid layers that can contain optical dye and density agents. By eliminating washes the invention simplifies instrumentation engineering and minimizes user steps and costs. The invention uses sensitive image analysis to enumerate individual targets in a large area, is scalable, and can be deployed in systems ranging in complexity from manual to highly automated.

In one aspect, the invention features a method for detecting one or more targets, e.g., measuring less than 50 microns in at least two orthogonal dimensions, in a sample by providing a vessel having a detection surface with a detection area having a shortest linear dimension of ≥1 mm; contacting, in a liquid overlying layer in the vessel, signaling moieties (e.g., having photonic signaling character), selection moieties, and a composition including the targets to form complexes of the targets and the signaling moieties or selection moieties; applying a selection force to move the selection moieties in the overlying layer through an underlying cushion layer and into contact with the detection surface; and detecting signaling moieties within a detection zone corresponding to the detection area, thereby detecting the targets. The method does not include a washing step. The underlying cushion layer may include a dye that interferes with the production or transmission of light to or from the signaling moieties.

In a related aspect, the invention features a method for detecting one or more targets, e.g., measuring less than 50 microns in at least two orthogonal dimensions, in a sample by providing a vessel having a detection surface with a detection area having a shortest linear dimension of ≥1 mm; contacting, in a liquid in the vessel, one or more signaling moieties (e.g., having photonic signaling character), selection moieties, and a composition including the targets to form complexes of the targets and the signaling moieties or selection moieties; applying a selection force to move the complexes through the liquid and into contact with the detection surface; and detecting signaling moieties within a detection zone corresponding to the detection area, thereby detecting the targets. The method does not include a washing step.

In various embodiments of the invention, the signaling moieties or selection moieties are conjugated to a category-binding molecule, such as an antibody, an antigen, a lectin, a nucleic acid molecule, a ligand, a receptor, or a small molecule. Preferably, the signaling moieties specifically bind to the targets. Individual complexes of the targets with the signaling moieties in the detection zone may be simultaneously detecting, e.g., with a photoelectric array detector. Preferably, detection employs magnification of less than 5×, e.g., no magnification. Exemplary targets are cells, such as bacterial cells (e.g., *Staphylococcus aureus* cells or *Bacillus anthracis*) or molecules secreted by microbial cells. When cells are detected, the method may further include contacting the cells with a second signaling moiety that specifically binds to an internal component of the cell, e.g., a nucleic acid molecule or a lipid. The second signaling moiety may be photobleached, and the method may include detecting the original signaling moiety after the photobleaching. Exemplary signaling moieties are fluorescent particles and a DNA stain. Samples may be combined with microbiological growth medium, e.g., including an antibiotic or microbial growth inhibitor, followed by incubation for more than 1 hour prior to being contacted with selection or signaling moieties. Signaling moieties or selection moieties may be in dried form in the vessel. When present, an underlying cushion layer may be in dried form in the vessel. The composition including the targets may hydrate any reagent in dry form in a vessel. In certain embodiments, the composition hydrates both an underlying cushion and signaling and selection moieties so that two liquid layers are produced. Targets may be present in, or obtained from, a biological fluid, e.g., human whole blood, serum, plasma, mucus, or urine. Exemplary selection forces include gravity, magnetism, electrical potential, centrifugal force, centripetal force, buoyant density, filtration, and pressure. Signaling moieties may include fluorophores, chemiluminescent agents, bioluminescent agents, resonance light scattering particles, light absorption or chromogenic signaling agents, or up-converting phosphors. Selection moieties may include magnetic particles, silica particles, or ferritin. An exemplary vessel is an imaging well having an imaging depth of greater than 2 mm.

The methods may be employed as a competitive assay, where the selection moieties are conjugated to target competitors; the complexes formed are between the selection moieties and signaling moieties and the target and the signaling moieties; the target does not specifically bind with the selection moiety; and the detection of the target occurs indirectly by a reduction in the amount of complexes of selection moieties and signaling moieties formed in the absence of the target.

Some or all of the reagents for the tests may be contained in a testing device. Some or all of the reagents can be combined by a user manually or by an automated instrument. Testing devices may be simple containers. Alternatively, they can be complex cartridges including, for example, one or more of the following: onboard pumps, fluidics channels, valves, reagent reservoirs, electronics, detectors, sample input modules, and waste modules.

In certain embodiments, the methods employ labeling particles as the signaling moiety. Contacting of the labeling particles with a target results in the formation of target: labeling particle complexes. Labeling particles may be employed in the methods in an amount to result in a specified labeling ratio, e.g., less than 100.

By imaging is meant simultaneous acquisition of an image from a detection area.

By washing is meant a process for physically removing, from a container or a surface, liquid containing undesirable components from targets, which, in contrast to the undesired components, are either retained, selected, or captured in the container or on the surface.

By a test not requiring washing is meant a test in which targets are detected without using wash steps.

By an analyzer or imaging analyzer is meant an apparatus having an array photodetector and imaging optics allowing simultaneous imaging of a detection area, as defined herein. Analyzers can have many other functions for enhancing detection including modules for applying selective forces on selection moieties, conveyance, or incubation.

By a well is meant a vessel that can hold liquid. Wells generally have a well depth ≥1 mm.

By an imaging well is meant a well through which labeled targets can be detected by imaging. Imaging wells have a detection surface on which an imaging analyzer can detect labeled target particles. The material lying between the detection surface and the imaging analyzer's photodetector has optical properties for supporting imaging detection of labeled targets. For example, the material is generally transparent and has low optical background in the spectral region corresponding to the signal signature of the device's signaling moieties.

By imaging well depth is meant the height of the imaging well along an axis that is perpendicular to the detection surface.

By cushion, density cushion, liquid cushion, cushion layer, or liquid density cushion is meant a substantially liquid layer which is denser than the overlying layer (e.g., the liquid layer has a density that is at least 1%, 2%, 5%, 8%, 10%, 15%, 20%, 30%, 35%, 40%, or 50% or more greater than the overlying layer). In the invention, the cushion is found in the imaging well lying between the detection surface and the liquid layer including the sample and test reagents. This cushion provides a physical separation between the test's reagents and the detection surface. Using selection, labeled targets complexed with selection moieties are moved through the cushion and deposited on the detection surface for imaging. Signaling moieties which are not complexed with a selection moiety are excluded from the detection zone by the dense liquid layer of the cushion.

By dye is meant a substance or mixture added to the reaction which interferes with the production or transmission of light to or from signaling moieties. The dye reduces or eliminates signal originating outside of the detection zone while allowing detection of the signal derived from signaling moieties within the detection zone. For devices that include fluorescent signaling moieties, dyes can absorb light of the fluorescent excitation frequencies, the fluorescent emission frequencies, or both. Various dye properties can be useful for this purpose including light scattering and absorbance. In various embodiments, the dye reduces signal by at least 50%, 75%, 85%, 90%, 95%, or even 99%.

By dyed cushion is meant a cushion that includes dye. The dyed cushion simultaneously provides a physical exclusion of the bulk reaction from the detection zone (as a function of the density of the dyed cushion) while preventing or reducing the transmission of signal from the overlying reaction to the detector (as a function of the dye included in the dense layer).

By sampling device is meant a device used to collect a sample. Examples of sampling devices include swabs, capillary tubes, wipes, beakers, porous filters, bibulous filters, and pipette tips.

By target is meant a cell, virus, molecule (e.g., a macromolecule, such as, e.g., a protein, DNA, RNA, or carbohydrate, and a small molecule, such as, e.g., a chemotherapeutic drug, a lipid, a sugar, an amino acid, or a nucleotide), or molecular complex that is potentially present in a sample and the presence of which is tested by the invention.

By target competitor is meant a cell, virus, molecule (e.g., a macromolecule, such as, e.g., a protein, DNA, RNA, or carbohydrate, and a small molecule, such as, e.g., a chemotherapeutic drug, a lipid, a sugar, an amino acid, or a nucleotide), or molecular complex that competes with target for binding to a category-binding molecule. A target competitor may be a target that is conjugated or stably attached to a selection moiety.

By category of target is meant one or more features shared by multiple targets so that the multiple targets are considered identical for the purposes of a test constructed using the invention. For example, for a test designed to detect all HIV viruses, the category is HIV. Such a test would detect all HIV viruses, without differentiating the HIV-1 and HIV-2 variants. In this case, the category of the target includes both HIV-1 and HIV-2. The goal of another test might be to distinguish HIV-1 from HIV-2. In this case, each type of HIV would be considered a different category. If the goal of the test is to detect *C. albicans*, three probes considered identical for the purpose of the test because they share the common feature that they bind specifically to *C. albicans* would be considered to be in the same category of target molecules.

By category-binding molecule is meant a molecule or molecular complex that specifically binds to a category-specific binding site. Examples of category-binding molecules are nucleic acid probes that hybridize to genomic DNA; nucleic acid aptamers that have been selected or "evolved" in vitro to bind specifically to sites on proteins; antibodies that bind to cellular antigens or serum proteins; and ligands such as epidermal growth factor or biotin that bind specifically to hormone receptors or to binding molecules, such as avidin. Two category-binding molecules are distinct if they bind to distinct and non-overlapping category-specific binding sites. Category-binding molecules may be referred to according to their molecular composition, e.g., a category binding oligonucleotide, probe, antibody, ligand, etc. The term "antibody" according to the present invention includes, e.g., any polypeptide capable of binding with specificity to a molecule or molecular complex, including e.g., complete, intact antibodies, chimeric antibodies, diabodies, bi-specific antibodies, Fab fragments, F(ab')2 molecules, single chain Fv (scFv) molecules, tandem scFv molecules, and aptamers. Complete, intact antibodies include monoclonal antibodies such as murine monoclonal antibodies (mAb), polyclonal antibodies, chimeric antibodies, humanized antibodies and human antibodies. The antibody can also include synthetically derived sequences.

By specifically binds is meant that a category-binding molecule binds to a molecule or molecular complex with a dissociation constant less than $10^{-6}$M, more preferably less than $10^{-7}$M, $10^{-8}$M, $10^{-9}$M, $10^{-10}$M, $10^{-11}$M, or $10^{-12}$M, and most preferably less than $10^{-13}$M, $10^{-14}$M, or $10^{-15}$M. Specific binding of a category-binding molecule to a category of target may occur under binding conditions to essentially all targets (e.g., at least about 70%, 80%, 90%, 95%, 99%, or more targets bind to the category-binding molecule) that are members of a category scanned for by a test, but to substantially no other molecules (e.g., less than about 1%, 5%, 10%, 15%, 20%, or 25% non-target molecules bind to the category-binding molecules) that are likely to be present in the sample. The number of category-binding molecules that are bound by targets in a category scanned for as compared to the number bound by targets not in such a category, are typically two-fold, five-fold, ten-fold, or greater than fifty-fold greater.

By capture molecule is meant a category-binding molecule that is stably bound to a surface, membrane, or other matrix that is not a particle.

By signal element is meant a molecule or particle that directly generates a detectable signal. The phrase "directly generates" refers to the fact that signal elements are the immediate source or critical modulator of the detectable signal. Thus, if the signal is photons that arise from a fluorophore, the fluorophore is the immediate source of the photons and, therefore, is a signal element. If the signal is photons scattered by an RLS particle, the RLS particle is a signal element. Alternatively, if the signal is the light transmitted or scattered from a chromogenic precipitated product of the enzyme horseradish peroxidase, the chromogenic product is the signal element.

A characteristic of a signal element is that such an element cannot be divided into parts such that each part generates a signal that is comparable (in character, not necessarily in intensity) to the whole. Thus, a 2 nM diameter quantum dot is a signal element, as dividing it changes the character (emission spectrum) of the resulting nanocrystals. A 5 μm particle impregnated with a fluorescent dye such as fluorescein, is not a signaling element, since it could be divided into parts such that each part has signaling characteristics comparable to the intact particle. The molecule fluorescein, in contrast, is a signaling element. The detectable products of signal generating enzymes (e.g., luciferase, alkaline phosphatase, horseradish peroxidase) are also considered signal elements. Such signal elements (or their precursors when there is a chemical conversion of a precursor to a signal element) may be diffusible substances, insoluble products, and/or unstable intermediates. For example, the enzyme alkaline phosphatase converts the chemiluminescent substrate CDP-Star (NEN; catalog number NEL-601) to an activated product, which is a photon-emitting signal element.

By signaling moiety is meant a molecule, particle, or substance including or producing (in the case of enzymes) one or more signal elements and that is or can be stably attached to a category-binding molecule. The signaling moiety can be attached to the category-binding molecule either covalently or non-covalently and either directly or indirectly (e.g., via one or more adaptor or "chemical linker" moieties or by both moieties being conjugated to the same particle). Examples of signaling moieties include carboxylated quantum dots; a fluorophore such as Texas Red that is modified for binding to a nucleic acid probe or an antibody probe; streptavidin-coated fluorescent polystyrene particles (which can be conjugated to biotinylated category-specific binding proteins); a rolling-circle replication product containing repeated nucleic acid sequences each of which can hybridize to several oligonucleotides tailed with fluorescently modified nucleotides and which contains a category-specific binding oligonucleotide at the 5' end. A signaling moiety can include physically distinct elements. For example, in some cases the signaling moiety is an enzyme (e.g., alkaline phosphatase) that is conjugated to a category-binding molecule (an antibody, for example). Signal is generated when a substrate of alkaline phosphatase (e.g., CDP-Star, or BM purple from NEN and Roche, respectively) is converted to products that are signal elements (e.g., an unstable intermediate that emits a photon, or a precipitable chromogenic product). It is not unusual for the category-binding molecules, enzymatic signaling moieties, and substrate to be applied to the reaction at distinct times.

By particle is meant a matrix which is less than 50 microns in size. The size of a population or batch of particles is defined as the mean measurement of the longest pair of orthogonal dimensions for a sample of the particles. The longest pair of orthogonal dimensions is the pair of orthogonal dimensions of a particle, the sum of the lengths of which is the maximum for all such sums for the particle. If a sample of two particles has a longest pair of orthogonal dimensions of 1 micron×2 micron and 2 micron×3 micron, respectively, the mean measurement of the longest pair of orthogonal dimensions is 2 microns [(1+2+2+3)/4=2 microns]. The mean measurement of the longest pair of orthogonal dimensions for a sample of particles is, e.g., less than 50 microns, less than 20 microns, or less than 5 microns.

Many particles have some characteristics of a solid. However, molecular scaffolds or complexes, which may not be rigid, are also defined as particles. For example, dendrimers or other branching molecular structures are considered to be particles. Similarly, liposomes are another type of particle. Particles can be associated with or conjugated to signal elements. Particles are often referred to with terms that reflect their dimensions or geometries. For example, the terms nanosphere, nanoparticle, or nanobead are used to refer to particles that measures less than 1 micron along any given axis. Similarly, the terms microsphere, microparticle, or microbead are used to refer to particles that measure less than one millimeter along any given axis. Examples of particles include latex particles, polyacrylamide particles, magnetite microparticles, ferrofluids (magnetic nanoparticles), quantum dots, etc.

By labeling particle is meant a particle that can specifically bind to targets and generate a signal. Labeling particles are conjugated to both signaling moieties and to category-binding molecules.

By target:labeling particle complex is meant a labeling particle to which one or more targets are specifically bound.

By labeling ratio is meant the ratio of targets to labeling particles during a contacting step. For example, if $1\times10^7$ labeling particles are contacted with a sample containing $1\times10^6$ targets, the labeling ratio is 0.1. For the purposes of calculating labeling ratios, only the targets that can specifically bind to labeling particles are considered. For example, targets that are physically inaccessible (e.g., sequestered in a cellular compartment) are not included in the calculation.

By signal character of a signal element or signal moiety is meant the aspect or aspects of a signal generated by the signal element or signaling moiety that is useful for distinguishing it from other signal elements or signaling moieties. For example, the signal character of a signaling moiety labeled with fluorescein and rhodamine is fluorescence. The character of a radio transponder is radio frequency. Examples of photonic signaling character are fluorescence, light scattering, phosphorescence, reflectance, absorbance, chemiluminescence, and bioluminescence. All but the latter two examples of photonic signaling character depend on external illumination (e.g., a white light source, a laser light source, or daylight). In contrast, chemiluminescence and bioluminescence are signaling characters that are independent of external light sources.

By signal signature is meant the distinctive signaling quality of the combination of signaling moieties that bind to a category of targets in a test. A target that is bound to four types of antibodies, one of which is conjugated to a fluorescein molecule, and three of which are conjugated with rhodamine molecules has a signal signature that is described by the combined weighted absorbance and emission spectra of fluorescein and rhodamine.

By selection force is meant a force that is used to capture, isolate, move, or sequester targets. Examples of selection forces include gravity, magnetism, electrical potential, centrifugal force, centripetal force, buoyant density, and pressure. Targets can be mobilized by a selection force acting on the targets alone. Alternatively, selection forces can act specifically on targets that are associated with selection moieties (see definition below).

Examples of the application of selection forces to mobilize targets include centrifugation of targets; magnetic selection of targets bound to magnetic particles; gravitational sedimentation of targets labeled with metallic particles; and deposition of targets on a porous membrane by vacuum filtration. Further instances of the use of selection forces are included in the examples below.

By selection moiety is meant an atom, molecule, particle, or other entity that can be conjugated to a category-binding molecule and that confers on the category-binding molecule the ability to be selectively captured, isolated, moved, or sequestered by a selection force. When a category-binding molecule:selection moiety complex is specifically bound to a target, the target can also generally be selectively captured, isolated, moved, or sequestered by the selection force. Selective refers to the preferential conferring of susceptibility to mobilization by the selection force on selection moieties and associated entities over entities not associated with selection moieties.

Paramagnetic particles and ferritin are examples of selection moieties. A dense silica particle that sinks in solution is another type of selection moiety. Such particles, when coated with category-binding molecules and bound to a microbial target will cause the target to sink in aqueous solution, thus separating of the bound target from other sample unbound constituents.

By selective character is meant the aspect or aspects of a selection moiety that are useful for capturing, selecting, or moving the selection moiety. For example, the selective character of a paramagnetic particle is magnetism. The selective character of a silica particle that rapidly sinks in aqueous solution is density.

By a roughly planar surface or substrate is meant a surface that can be aligned in parallel to an imaginary plane such that when the distance is measured from points in any 1 mm×1 mm square on the surface to the closest points on the imaginary plane, the absolute value of the mean distance is less than 50 micrometers.

By detection surface is meant the surface of a roughly planar substrate onto which targets are deposited in some embodiments of the invention. In embodiments using photonic signaling character, if the detection surface is optically transparent, detection can be effected via either face of the detection surface. If the detection surface is opaque, detection is effected via the face of the detection surface on which the targets are deposited.

By detection area is meant the area of the detection surface or detection zone that is simultaneously analyzed by the invention. The detection area is typically greater than 1 mm, e.g., greater than 5 mm, 10 mm, or 15 mm, in its longest linear dimension. For example, the section of a glass slide that is simultaneously imaged by an optical device that includes a collection lens and a CCD chip might measure 0.8 cm×0.5 cm. The detection area is then 0.4 cm$^2$.

By detection zone is meant the volume in which targets can be detected. The detection zone has the same dimensions as the detection area but has a depth corresponding to the depth in which a labeling particle can be detected and identified. The depth of the detection zone is therefore dependent on the threshold criteria used to score for positive signal. When optical detection is used, the depth of the detection zone is dependent on the optical depth of field.

By the longest dimension of the detection area is meant the line of maximum length that can be drawn between two points on the perimeter of the detection area. For example, if the detection area is a rectangle measuring 0.3 cm×0.4 cm, the longest dimension of the detection area is the diagonal, 0.5 cm. If the detection area is an ellipse with semi-major axis of length 7 mm and semi-minor axis of length 2.5 mm, the longest dimension of the detection area is 14 mm.

By the shortest dimension of the detection area is meant the line of minimum length that can be drawn between two points on the perimeter of the detection area. For example, if the detection area is a rectangle measuring 0.3 cm×0.4 cm, the shortest dimension of the detection area is 0.3 cm. If the detection area is an ellipse with semi-major axis of length 7 mm and semi-minor axis of length 2.5 mm, the shortest dimension of the detection area is 5 mm.

By large area detection or large area imaging is meant a method for detecting microscopic targets in which the detection area (the area that is simultaneously analyzed by the detection device) is much larger than the target. The detection area for large area detection has linear dimensions ≥1 mm. In contrast, the microscopic targets are substantially smaller, typically measuring less than 50 μm in at least two orthogonal dimensions. Examples of large area detection include imaging a 9 mm diameter detection area with a CCD camera; imaging a 2 cm×1 cm rectangle by scanning with a CCD line scanner that has a long dimension of 1 cm; imaging a 4 cm×4 cm filter containing microbial targets using direct exposure on photographic film; and visual detection of colored spots corresponding to microscopic targets on a 1 cm×3 cm test area in a rapid lateral flow strip test.

By conjugated or stably associated is meant a physical association between two entities in which the mean half-life of association is least one day in PBS at 4° C.

By simultaneously detecting targets in a section of the detection area is meant detection of the signal from a section of a roughly planar detection surface in one step. Large area imaging of targets in a detection area using a CCD chip, visual detection, or photodiode-based signal integration are examples of simultaneous detection.

By sample is meant material that is scanned by the invention for the presence of targets.

By direct visual detection is meant visual detection without the aid of instrumentation other than wearable corrective lenses. For example, direct visual detection can be used to detect the reddish reflective signal of nanogold particles in some rapid lateral flow tests.

By photoelectric detector is meant a man-made device or instrument that transduces photonic signals into electric signals. Examples of photoelectric detectors include CCD detectors, photomultiplier tube detectors, and photodiode detectors, e.g., avalanche photodiodes.

By illuminating is meant irradiating with electromagnetic radiation. Electromagnetic radiation of various wavelengths can be used to illuminate. It includes, for example, radiation with wavelengths in the X-ray, UV, visible, or infrared regions of the spectrum. Note that illuminating radiation is not necessarily in the visible range.

By signal elements or signaling moieties with photonic signaling character is meant signal elements or signaling moieties that are detectable through the emission, reflection, scattering, refraction, absorption, capture, or redirection of photons, or any other modulation or combination of photon behavior. Some examples of signal elements or signaling moieties that have photonic signaling character include: the fluorophore Texas Red (fluorescent signaling character); CDP-Star (chemiluminescent signaling character); luciferase (bioluminescent signaling character); resonance light scattering particles (light scattering signaling character); BM purple (light absorption or chromogenic signaling character); and up-converting phosphors (absorption of two long wavelength photons and emission of one shorter wavelength photon).

PBS is a phosphate-buffered saline solution containing: 120 mM NaCl, 2.7 mM KCl and 10 mM phosphate buffer (sodium salt) pH 7.4.

PBS-TBP is a phosphate-buffered saline solution containing: 120 mM NaCl, 2.7 mM KCl and 10 mM phosphate buffer (sodium salt) pH 7.4 containing 2 mg/ml BSA, 0.05% Tween 20 and 0.05% v/v Proclin® 300

Tris-TBP is 20 mM Tris HCL pH 7.4 containing 2 mg/ml BSA, 0.05% Tween 20 and 0.05% v/v Proclin® 300

EDAC is (1-Ethyl-3-(3-dimethylaminopropyl)carbodiimide.

BSA is bovine Serum Albumin.

CCD is charged coupled device.

CFU is colony forming unit (a measure of bacterial concentration that corresponds to the number of viable bacterial cells).

HBV is Hepatitis B virus.

HCV is Hepatitis C virus.

HIV is Human Immunodeficiency virus.

TSH is thyroid stimulating hormone

Unless otherwise noted, microbiological strains described in the specifications are obtained from the American Type Culture Collection (ATCC), Manassas, Va.

BRIEF DESCRIPTION OF THE DRAWINGS

FIG. 1. Specific vs. Nonspecific Labeling.

FIG. 2. Methods for contacting the sample with other reaction components.

FIG. 3. Different methods for capture of targets.

FIG. 4. Labeling of S. aureus with Fluorogenic DNA stain-Relative log fluorescence intensity of SYTO-13® staining of S. aureus DNA.

FIG. 5. Labeling of Staphylococcus aureus cells with chicken anti-protein A antibodies conjugated to fluorescent nanoparticles. Relative log fluorescence intensity of S. aureus cells stained by antibody coated fluorescent particles.

FIG. 6. Determining binding efficiency of S. aureus specific fluorescent particles by flow cytometry.

FIG. 7. Testing magnetic particles coated with anti-Staphylococcus aureus antibodies. Bioassay shows number of magnetic particles vs. percentage magnetic capture of S. aureus after magnetic selection.

FIG. 8. Chromotrope 2R dye absorbs light at wavelengths corresponding to light passed by the excitation and emission filters used in the imager.

FIG. 9. Dye can be used to attenuate the signal from fluorescent particles.

FIG. 10. Assay of Human Thyroid Stimulating Hormone (hTSH) in human serum using magnetic capture and dye.

FIG. 11. Test of Dye-cushion reagent demonstrating the effect of dye and cushion using human Thyroid Stimulating Hormone assay reagents.

FIG. 12. Test of dye cushion reagent demonstrating the effect of dye and of cushion using TSH assay reagents. Magnetic selection experiment for hTSH.

FIG. 13. Concentration of density agent needed to form a bilayer system when the sample is whole blood.

FIG. 14. Sensitive detection of hTSH in whole blood by enumeration of individual fluorescent microparticles after selection through a dye cushion.

FIG. 15. Detection of human Thyroid Stimulating Hormone (hTSH) in human whole blood using magnetic capture, cushion dye reagent, carrier magnets. (Example 8)

FIG. 16. Assay of Human Thyroid Stimulating Hormone (hTSH) in human plasma using dispersed magnetic capture and cushion dye reagent. (Example 9)

FIG. 17. Assay of Human Thyroid Stimulating Hormone (hTSH) in human plasma using dispersed magnetic capture and cushion dye reagent. (Example 9)

FIG. 18. Detection of bacterial *Bacillus anthracis* Lethal Factor (LF) in human plasma using magnetic capture and cushion dye reagent. (Example 10)

FIG. 19. Detection of bacterial *Bacillus anthracis* Lethal Factor (LF) in human plasma using magnetic capture and cushion dye reagent. (Example 10)

FIG. 20 Detection of bacterial *Bacillus anthracis* Protective Antigen (PA) in human plasma using magnetic capture and cushion dye reagent. (Example 11)

FIG. 21. Detection of bacterial *Bacillus anthracis* Protective Antigen (PA) in human plasma using magnetic capture and cushion dye reagent. (Example 11)

FIG. 22. Detection of bacterial *Bacillus anthracis* poly-D-γ-glutamic acid (PDGA) capsule polypeptide in human urine. (Example 12)

FIG. 23. Detection of bacterial *Bacillus anthracis* poly-D-γ-glutamic acid (PDGA) capsule polypeptide in human urine. (Example 12)

FIG. 24. Detection of bacterial *Bacillus anthracis* Lethal Factor in human whole blood by automated analysis. (Example 13)

FIG. 25. Competitive immunoassay for detection of bacterial protein *Bacillis anthracis* poly-D-γ-glutamic acid capsule polypeptide. (Example 14)

FIG. 26. Positive and negative internal assay controls for human TSH and bacterial *Bacillus anthracis* PA and PDGA. (Example 15)

FIG. 27. Enumeration of individual *Staphylococcus aureus* cells labeled with DNA stain, after magnetic selection through a dye cushion. (Example 16)

FIG. 28. Specificity of S. aureus dye cushion assay using nonspecific labeling with DNA stain and specific magnets. (Example 16)

FIG. 29. Detection of S. aureus by detection with nonspecific Sybr Green DNA staining and magnetic selection with dye cushion reagent. (Example 16)

FIG. 30. Labeling of Staphylococcus aureus cells with chicken anti-protein A antibodies conjugated to fluorescent nanoparticles. (Example 17)

FIG. 31. Specificity of Staphylococcus aureus assay with a specific label, chicken anti-protein A antibodies conjugated to fluorescent nanoparticles. (Example 17)

FIG. 32. Detection of S. aureus cells by detection with chicken anti-Protein A antibodies conjugated to Fluorescent Particles and Magnetic selection with dye cushion reagents. (Example 17)

FIG. 33. Protocol for detection of methicillin resistant S. aureus (MRSA) through selective growth and immunodetection of cells. (Example 18)

FIG. 34. Detection of methicillin resistant S. aureus (MRSA) through selective growth and immunodetection of cells. (Example 18)

FIG. 35. Stabilization of Reagents-Lyophilization of human Thyroid Stimulating Hormone reagents. (Example 19)

FIG. 36. Assay of human Thyroid Stimulating Hormone utilizing lyophilized reagents. (Example 19)

FIG. 37. Stabilization of reagents-Lyophilization of Methicillin resistant S. aureus reagents. (Example 20

FIG. 38. Assay for S. aureus utilizing lyophilized reagents. (Example 20)

FIG. 39. Specific detection of biotin by movement of the selected complexes. (Example 21)

FIG. 40. Specific detection of S. aureus in an assay utilizing photobleaching. (Example 22)

FIG. 41. Use of photobleaching to identify debris in an image where the label is susceptible to photobleaching. (Example 23)

FIG. 42 is a photograph of a cartridge for an automated analyzer.

FIG. 43 is a photograph of an automated analyzer.

FIG. 44 is a schematic depiction of an automated analyzer.

FIG. 45 is a schematic depiction of the imaging optics of an automated analyzer.

FIG. 46 is a schematic depiction of a magnet assembly.

FIG. 47 is series of images of the detection of individual labeled S. aureus cells.

DETAILED DESCRIPTION OF THE INVENTION

Overview of the invention. The invention tests samples for the presence of microscopic targets (cells, viruses, molecules (e.g., a macromolecule, such as, e.g., a protein, DNA, RNA, or carbohydrate, and a small molecule, such as, e.g., a chemotherapeutic drug, a lipid, a sugar, an amino acid, or a nucleotide), or molecular complexes) using sensitive large area to count individual labeled targets and methodology that does not require wash steps. These attributes of the invention allow for accurate, sensitive, specific, rapid, easy-to-use, and cost-effective testing while simplifying instrumentation engineering and minimizing user steps. The methods may be carried out using an imaging analyzer as described herein and in International Application No. PCT/US2009/58274, titled "Imaging analyzer for testing analytes," filed Sep. 24, 2009, which is hereby incorporated by reference, and/or with kits or devices as described herein and in International Application No. PCT/US2009/058237, titled "Kits and devices for detecting analytes," filed Sep. 24, 2009, which is hereby incorporated by reference.

Some of the key functions and attributes of the method are described in the following sections:
1. Samples
2. Targets
3. Sample processing
4. Test device
5. Labeling
6. Selection
7. Assay format.
8. Contacting
9. Depositing
10. Distinguishing labeled targets
11. Detection
12. Analysis
13. Assembly 1. Samples Samples that potentially contain targets and that can be tested by the invention may be liquid, solid, gaseous, or a combination of all three. Sample types include clinical (e.g., blood or urine), manufacturing (e.g., foodstuffs or pharmaceuticals), and environmental (e.g., air, surface, or water). Samples may be substantially homogeneous, e.g. a liquid containing solutes and few particulates, or sample may be heterogeneous, such as suspension of clay or other particles from environmental samples such as soil. Samples may contain one or more types of targets, and the targets may be natural or synthetic targets, or a mix of natural and synthetic targets, e.g. a blood sample may contain both a hormone (a natural substance) and a synthetic drug.

Samples sources that can be tested using the invention can include humans, animals, plants and sample types may include urine, blood, bile, synovial joint fluid, serum, plasma, spinal fluid, amniotic fluid, sweat, nasal and respiratory fluid, vaginal secretions, ejaculate, wound exudates, sputum and bronchoalveolar lavage fluids, hemolymph from an arthropod or mollusc, or fluids obtained from plants such as cell sap. Samples may also include solids from humans or other organisms, and samples which may have liquid or solid character, such as feces, which can vary from a clear liquid to a firm solid, and others such as bone, hair, dried cells, skin samples, fresh, frozen or fixed pathology samples, and swabs taken from nasal, nasopharyngeal, throat, axillar, perineal or rectal sites. Other biological samples include gases from biological sources, such as flatus, or gas which may be collected from the oral or nasal cavity.

Samples include materials from natural, industrial or commercial sources, including raw materials, in process, manufactured or finished products, such as foods, beverages, animal feeds, cosmetics, pharmaceutical or veterinary products, fertilizers, polymers, plastics, rubbers, wood or paper products, fabrics, and products for topical or internal use on humans, or animals or intermediates of any of the above. Other types of samples include material from research or testing laboratories, such as cell culture supernatants, cells grown in vitro, samples from animals such as mice or guinea pigs used for research or testing, or plant samples grown or taken for testing purposes. Samples may include liquids, solids or gases from natural sources, such as lake or river water samples monitored for bacteria or chemicals, soils to be tested for chemicals, toxins or micro organisms.

Manufacturing environmental monitoring samples, such as are obtained from industrial or medical equipment for environmental or chemical monitoring may also be tested using the invention. For example, a sample may be obtained by wiping or swabbing the surface of equipment used for manufacture or storage of foods or beverages.

Samples may contain living microorganisms, for example as in fermentor broth, blood samples from a person with a blood infection, or some food products.

The volume of the sample can vary from liters to nanoliters. For instance, in testing drinking water for the presence of contaminants, the sample may be liters of water; the sample may be processed to concentrate any targets which may be present. Conversely, if a researcher desires to do a long term study on the effect of a toxin or pharmaceutical on a living mouse and the sample is whole blood obtained from the mouse, it is desirable to limit the sample volume.

2. Targets

A target is a cell, virus, molecule (e.g., a macromolecule, such as, e.g., a protein, DNA, RNA, or carbohydrate, and a small molecule, such as, e.g., a chemotherapeutic drug, a lipid, a sugar, an amino acid, or a nucleotide), or molecular complex that is potentially present in a sample, and whose presence is tested for by the invention. Many different types of targets can be detected and or quantified using of the invention. The ability to sensitively detect many different types of targets is an advantage of the invention.

Targets may vary in size. Targets such as human egg cells or megakaryocytes may be 100 microns or more in diameter; circulating tumor cells may be several microns; bacteria may be one micron in diameter; while protein or nucleic acid targets may range in size from a few to hundreds of nanometers. Smaller targets, such as antibiotics, toxins and pesticides, may be 10 nanometers or less in size.

Targets may vary in abundance. For example, the concentration of bacteria or viruses present in blood samples can vary from less then 1 cell or CFU or virus per 10 mL to greater then $1 \times 10^6$ CFU or virus particles per mL; similarly, the concentration of proteins such as thyroid stimulating hormone, human chorionic gonadotropin or prostate specific antigen can vary greatly. For example, the concentration of human chorionic gonadotropin in serum can vary over more then 4 orders of magnitude, from less than 5 to greater than 150,000 mIU/mL.

A target may be a cell or cell fragment from a multicellular organism. Examples of cellular targets might include cells such as sperm, pollen, fungal or plant spores, and cells obtained from blood or other biological fluids. For example, CD4+ cells and circulating tumor cells may be found in blood; the former are used in HIV testing, and the latter may be useful in cancer diagnostics. Examples of cell fragments include platelets, a normal component of human blood, and subcellular fractions such as nuclei, mitochondria, lysosomes, or peroxisomes which result from sample processing.

A target may be a microorganism, or a part of a microorganism, such as a fragment of a cell wall, or an agglomeration of two or more microorganisms. Microorganisms may include viruses, bacteria, bacterial spores, archeabacteria, fungi, protists, or multicellular microorganisms such as nematodes, copepods or rotifers. In many samples, such as environmental soil samples, or samples from the human digestive system, microorganisms may be bound to particulates, or may be present as part of a mixed flora.

A target may be a biological or artificial polymer, including nucleic acids, proteins and peptides, polysaccharides, and complexes, either covalent or noncovalent, between different types of polymers or between different types of polymers and nonpolymeric compounds, such as enzymes covalently modified by a prosthetic group. Targets may also include biological polymers which have been damaged, such as DNA molecules which have been damaged by UV radiation. Polymeric targets may also include synthetic polymers and synthetic analogues of biological polymers which have been modified to include synthetic compounds, such as a synthetic oligonucleotide, which may include moieties not normally found in nature. Peptides and peptide analogues, such as retro-reverso peptides, are another class of compounds which may be targets.

A target may be a natural molecule or a synthetic molecule. Examples of natural compounds include vitamins, hormones, neurotransmitters, lipids, amino acids, sugars, secondary metabolites, toxins, and pheromones. Examples of synthetic molecules include pesticides, chemical intermediates, monomers, plasticizers, surfactants, and other industrial products. The target may also be a pharmaceutical compound, e.g., a drug.

Proteins may be detected or quantified using the invention. Proteins include, for instance, cytokines, hormones, enzymes, structural proteins, receptors and so forth. Protein targets may also undergo modification, and the presence of such a modification may be of interest, such as the amount of glycosylated hemoglobin in blood, which is a marker used in diagnosis and treatment of diabetes. Proteins may occur in various complexes, either with other proteins, or other molecules, such as nucleic acids or low molecular weight molecules such as FAD.

In the case of enzymes, it may be useful to detect either the enzyme (a primary target) or a product of the enzyme (a secondary target). For instance, detection of lactamase may be done by providing a lactam antibiotic such as benzyl penicillin, and detecting benzyl penicilloic acid.

3. Sample Processing

Sample can be presented to the assay in various ways, depending on the sample to be tested and the assay. These include, but are not limited to, swabs in transport medium or swabs obtained from a sampling site; tubes of whole blood, serum or plasma; a drop of whole blood presented at the end of a finger after a use of a lance, or a drop of whole blood presented on the earlobe or other surface such as the forearm; formed or unformed stool present in a container; samples such as whole blood spotted onto a transport medium such as a filter paper or membrane; tear or sweat drops present on the skin or other bodily surface.

Sample processing may have several functions depending on the nature of the sample and the test requirements, but generally serves to improve the availability of targets for testing. Ideally, sample processing requires minimal effort on the part of the user. Sample processing can occur at various times and in various places. Sample processing can occur before the sample reaches the testing site, either at the collection point or some point in transit, or sample processing can occur as part of the testing process, or sample processing can occur at the testing site, but not as part of the testing process. Sample processing may occur in two or more discrete stages or steps, e.g. there may be processing to preserve targets at the collection site and further processing at the testing site to make targets amenable to the assay.

Sample processing may occur as part of sample collection. For instance, if a blood collection tube contains EDTA, coagulation of the blood will be prevented during collection; the user does not need to do anything other then select the right collection tube.

Some sample processing operations involve extraction of the target from a solid, semisolid, or liquid matrix or from a collection device. For example, a test to detect targets in a bone sample might involve steps of mechanical disruption and liquid extraction to solubilize the targets into the liquid phase so that they are amenable to the assay, and to concentrate the targets, so as to improve the sensitivity of the assay. Other processes, including filtration or centrifugation of a sample can be used to remove particulates from a soluble sample to allow testing of a uniform liquid. This might include processing of blood to produce plasma or serum, or removal of solids from a fecal sample before testing for C. difficile toxin. Sample processing methods may include steps such as purification, elution from a sampling device such as a swab or a filter, centrifugation in batch or continuous mode, electrophoresis or diaphoresis, chromatography, extraction or mixing with an aqueous or organic diluent or solvent, two-phase partitioning using polymers or salt, ultrasonic treatment for homogenization or disruption, pressure, for example using a French press to disrupt microorganisms. Mechanical sample treatments include sorting with a sieve; mechanical disruption, such as cutting, chopping, pressing or crushing, and grinding.

Other processing operations involve dilution or concentration of a sample or otherwise conditioning the sample for testing. For instance, a test to detect low concentrations of microorganisms present in a large sample of water might involve filtration and concentration steps. Pooling or combination of samples may be performed to reduce the total number or tests required. Sample processing may also be used to improve the quality of test results. In some cases, the sample may be suitable for testing without sample processing, but processing will improve the quality of results. For instance, the detection of a protein target in blood or plasma may be possible without sample processing, but the sensitivity of the assay may be improved by steps such as centrifugation. Thus, the amount and type of sample processing is determined both by the nature of the sample, the nature of the target, and the needs of the user for speed, ease of use, cost-effectiveness, reproducibility, freedom from interference, resolution and sensitivity.

Sample processing may involve adding various chemicals. For example, it may be necessary to adjust the pH of a sample by addition of acid or base, or adjust the salt concentration by adding NaCl, or to add reagents to cause either targets or other substances to precipitate. Addition of chemicals can cause several steps to occur simultaneously, for instance, addition of a polymer may cause the sample to form a two phase system, where the target is enriched in one phase and interfering substances are enriched in the other phase. Chemicals may be added to color the sample, for example, addition of colors may help users identify samples. Detergents may be added to effect lysis of cells (for instance saponin may be added to lyse mammalian cells without lysis of bacterial cells), to solubilize components, or to improve the wetting or flow of the sample during other steps such as filtration. Chemicals may be added prior to other steps as a pretreatment, for instance, detergents may be added to solubilize the sample prior to filtration.

Enzymes may be added for various reasons as part of the sample processing step. Disaggregation of tissues may be necessary to render cells suitable for testing. Also, it is well known that certain enzymes, such as lysozyme or lysostaphin, will degrade the cell walls of bacteria; addition of these enzymes may be used to liberate targets from the inside of the bacterial cell. Nucleases may be added during sample processing, for instance to reduce the viscosity of biological samples after processing. Enzymes may also be used to convert substrates into targets.

Sample processing may be used to preserve targets from degradation or modification For instance, protease inhibitors may be added to the sample at collection, to ensure that protein targets are not degraded by proteases and rendered undetectable. Preservatives, such as Proclin® or sodium azide may also be added at any point to prevent the growth of organisms; for instance, it is well known that many microorganisms secrete proteases and nucleases, and these enzymes may degrade the target of interest. Sample processing may involve a step where the sample is heated or cooled. For instance, refrigeration of a sample may be used to inhibit the growth of microorganisms between sample collection and testing; freezing may be used to prevent the degradation of labile targets.

When a sample contains microorganisms, it may be useful to process the sample under conditions that allow growth or selective growth of the organisms. For instance, in a test to determine if bacteria are present in blood, it may be useful to know if a single bacterium is present in a sample of several milliliters in volume. In this case, incubation of the sample, with or without dilution into bacterial growth medium, will allow the bacterium to divide and grow. In some cases, such as detection of one particular microorganism present in a sample that may contain other microorganisms, it may be useful to treat the sample so that only the organism(s) of interest survive, or to subject the sample to growth conditions which reveal a particular growth property of the organisms. For example, to detect the presence of methicillin resistant *Staphylococcus aureus* in a blood sample, it may be useful to mix the sample with a growth medium that contains an antibiotic, so that methicillin resistant organisms grow while methicillin sensitive organisms do not grow.

Sample processing methods may be combined. For instance, it might be necessary to centrifuge or filter a sample to remove particulates, and then remove interfering substances, and concentrate and purify the targets with chromatography. Processing steps may be performed manually or by automated equipment.

4. Test Device

The invention can be carried out in test devices of many configurations. To carry out the inventive steps the device generally comprises a reaction well which allows the sample and other components to contact each other and an imaging well comprising a detection surface which allows imaging of individual labeled target complexes by the detector. The detection surface allows transmission of the signal from the detection zone to the detector. The imaging well can also serve as the reaction well. Alternatively, a test device might comprise separate reaction and imaging wells. Or, separate devices containing the two types of wells can be used. The test reaction can be moved from the reaction well to the imaging well manually or automatically.

The reaction and imaging wells may also serve other functions. For instance, there may be fiducial marks in or near the detection surface of the imaging well to assist in focusing or to allow for alignment of images during analysis, or the container can be designed for the containment of biohazardous samples. The wells of the test device can be manufactured to contain test components, reducing later reagent addition steps. The test device can be disposable (that is, used once and discarded) or can be cleaned and reused.

Material and manufacturing methods for the test device are chosen based on the functional requirements of the test device, costs, and manufacturing complexity. For example, transparent low fluorescence plastics are generally used to construct imaging wells. Costs can be minimized by using commodity plastics and high volume manufacturing methods. One useful type of container is made of low cost materials, such as polystyrene, formed by high volume methods, such as injection molding, that result in very reproducible parts with low cost per part.

5. Labeling

To detect the presence of targets in the reaction, targets are contacted with and complexed to signaling moieties. Labeled targets within the detection zone produce a detectable signal when they are imaged.

The signaling moieties useful in the target labeling process can have a variety of signaling characters, including fluorescence, light-scattering, Raman scattering, phosphorescence, luminescence, chemiluminescence, bioluminescence, and color.

A variety of types of signaling moieties can be used in conjunction with the assay, as demonstrated in the examples below. These include but are not limited to single fluorophores, including fluorescent dyes like fluorescein, rhodamine, the Cy® dye series (GE healthcare) and the Alexa® series (Invitrogen), which can be modified for chemical coupling to proteins or nucleic acids; fluorescent nucleic acid stains like propidium iodide or the SYBR® and SYTO® stains (Invitrogen) which are fluorescent when complexed to nucleic acids; fluorescent proteins similar to green fluorescent protein or phycobiliproteins; and quantum dots. Higher intensity signals can be generated by incorporating multiple fluorophores into the signaling moiety. For example, fluorescently labeled polymers, and fluorescent microparticles can carry multiple fluorophores and generate high-intensity signal. Enzymes which generate a chemiluminescent, bioluminescent, or chromogenic signal when incubated with an appropriate substrate can, in the presence of their substrates, also comprise signaling moieties. In general, signaling moieties are selected taking the nature of the sample to be tested (e.g. intrinsic fluorescence) and the detection method (e.g. CCD-based imaging through a specific filter set) into account.

In some embodiments of the invention, a specific label is used to selectively label targets. A specific label includes one or more category binding molecules conjugated or stably associated with one or more signaling moieties described above. Examples of category binding molecules include: antibodies (if the target is an antigen); antigens (if the target is an antibody); lectins (if the target contains appropriate sugar moieties); nucleic acid probes complementary to a target sequence of interest; receptors (if the target is a receptor ligand); and ligands (if the target is a receptor).

Methods for covalent linkage of category binding molecules to signaling moieties are selected based on the chemical groups available on the two moieties to be linked. References such as Hemanson (Bioconjugate Techniques by Greg T. Hermanson and Chemistry of Protein Conjugation and Cross-Linking by Shan S. Wong) allow those skilled in the art to make use of a variety of conjugation methods. In one commonly used method, a chemically activated signaling moiety (e.g., fluorescent particle or dye molecule modified with N-hydroxysuccinimide) is conjugated to free amino groups on the specific binding moiety (e.g., an antibody) under reaction conditions appropriate to the molecules to be conjugated. In another common method, fluorescently labeled nucleotides are incorporated into an oligonucleotide probe when the probe is synthesized.

Some signaling moiety complexes can be formed by non-covalent association between signaling moieties and category binding molecules. For example, in the case of fluorescent polystyrene microparticles, a stably associated labeled specific binding moiety can be produced by adsorbing the specific binding moiety onto the surface of the microparticle.

A combination of covalent linkage and non-covalent stable association can also be used to generate signaling moiety complexes. For example, a category binding molecule can be chemically conjugated to biotin, and a signaling moiety can be chemically conjugated to streptavidin or avidin. When these components are contacted, a specific label is formed. This type of specific label can be formed before the test is carried out, or the components can be added separately to the reaction so that the specific label is produced during the reaction.

Some embodiments of the invention make use of labels that are not complexed with category binding molecules. These nonspecific labels generally produce a detectable signal by binding to or reacting with chemical classes or functional classes of molecules in the sample. FIG. 1 illustrates the distinction between specific and nonspecific labeling. One type of non-specific label can chemically modify ubiquitous chemical groups present in the sample, including the target. For example, N-hydroxysuccinimide-activated fluorescent dyes can couple to free amines throughout the sample, and if the target is present in the sample and contains free amines, it will be fluorescently labeled. Alternatively, N-hydroxysuccinimide-activated biotin can be used to couple biotin to free amines throughout the sample. In this case, the target and other amine-containing components of the sample can be labeled by addition of a signaling moiety complexed with biotin or streptavidin. Nucleic acid labeling agents (examples include propidium iodide and the SYTO and SYBR dye series, from Invitrogen) can be used to label all accessible nucleic acids in the sample, including the target if it contains nucleic acid. Another example of non-specific labeling is the labeling of all metabolically active cells in the sample when the target is a live cell. This might be achieved through use of live cell stains or metabolic dyes like fluorescein diacetate which are metabolized by living cells to produce a signaling moiety.

6. Selection

The invention generally uses selection to deposit labeled targets in the detection zone for imaging and to separate or distinguish bound from free signaling moieties.

A variety of selective characters can be employed in the invention, each associated with particular sets of selection moieties. Selective characters include but are not limited to magnetic selection, buoyant density-based selection, either by gravity or centrifugation, electrophoresis, dielectrophoresis, filtration, and simple capture onto a solid phase.

Selection moieties are chosen to be compatible with the selective force corresponding to the selective character. For magnetic selection, the compatible selection moieties include superparamagnetic particles, ferrofluids, and ferritin. For density-based selections, compatible selection moieties are denser than the reaction as a whole, including moieties like silica particles, melamine particles, polystyrene particles, or other dense particles. Filtration can be used as a selection mode when the labeled target can be selected by its size or by its ability to bind to a particular type of filter. Capture selection modes include the specific or nonspecific capture of labeled target complexes by capture molecules immobilized on a surface. Capture selection is most useful in the invention when the binding agents are immobilized at or near the detection zone, so that capture of labeled target complexes immobilizes the complexes within the detection zone for imaging.

In many embodiments of the invention, for example in the case of magnetic selection, the selection process is effected through the binding of a selection moiety to a labeled target to produce a selectable complex. In other cases, the selective character of the labeled target allows selection to be performed without preliminary formation of a selectable complex. For instance, filtration of specifically labeled bacteria makes use of the size of the target in the selection process to select all bacteria, including the labeled targets, onto the filter, where imaging will identify the labeled targets.

Selection moieties can specifically or non-specifically bind to a target. A target-specific selection moiety complex has a selection moiety linked to one or more category-specific binding moieties. An anti-TSH antibody-conjugated magnetic particle is an example of a target-specific selection moiety complex. Category-specific selection moiety complexes bind to the target but not to other components present in the sample. Non-specific selection moiety complexes can also be produced, which will bind to broad classes of components in the sample including the target. One example of a non-specific selection moiety complex is a magnetic particle conjugated to a poly-cation which binds to all poly-anionic components in the sample, including a poly-anionic target.

Producing target-specific and non-specific selection moiety complexes. Methods for production of target-specific and nonspecific selection moieties can be identical to those described for production of specific labels in the labeling section above. The specific or non-specific binding moieties are linked covalently or non-covalently to selection moieties to form a stable association between the components. In some cases, the binding characteristics of a selection moiety are intrinsic to the selection moiety. For instance, if a polycationic selection agent is desired, a particle which is itself polycationic could be used without further modification.

A combination of covalent linkage and non-covalent stable association can also be used to generate target-specific selection moieties. For example, a category binding molecule can be chemically conjugated to biotin, and a selection moiety can be chemically conjugated to streptavidin or avidin. This type of target-specific signaling moiety can be formed before the test is carried out, or the components can be added separately to the reaction so that the target-specific signaling moiety is produced during the reaction.

7. Assay Format.

The invention can detect a wide range of targets. Many embodiments are carried out in a "sandwich" format, where targets are labeled to allow detection by an imaging method, and are additionally complexed to a selection moiety to allow deposition of labeled targets within the detection zone so that they can be imaged. The precise selection of labeling and selection methods depends on properties of the sample, on the detection method to be used, and on properties of the target itself.

With respect to their reaction with specific binding moieties, targets fall into three classes: Small molecule targets, macromolecular targets without repeating determinants, and multivalent targets.

Small molecules (haptens) generally can be bound only by a single specific binding moiety. This does not permit their simultaneous binding by category binding moieties linked to signaling and selection moieties. In the current invention, detection of small molecules can be achieved via a competitive format where the addition of target inhibits the capture of signaling moieties within the detection zone. There are three basic competitive format embodiments of the invention for the detection of small molecules. In one competitive assay embodiment the category binding molecules used for signaling and for selection are complementary to each other, where one category binding molecule is a target competitor and the other is a category binding molecule that binds the target or the target competitor. In the absence of target in the sample, the signaling moiety and selection moiety bind directly to each other, so that when the deposition step of the invention is carried out, measurable signal can be deposited in the detection zone and imaged. If target molecules are present in the sample, the formation of complexes between the signaling and selection moieties is inhibited, so that the quantity of signal deposited in the detection zone is an inverse function of the quantity of target added to the reaction. In a second competitive assay embodiment, both the signaling moiety and the selection moiety are conjugated to target competitor. The crosslinking of signaling moiety and capture moiety is effected by an at least bivalent category-specific molecule (e.g. an antibody) supplied in the reaction. The crosslinking reaction is inhibited by the binding of added target to the bivalent category-specific binding molecule resulting in a reduction in the quantity of signal when target is present in the reaction. In a third competitive embodiment (c), the signaling and selection moieties are each conjugated to category-binding molecules which can bind to the target. The addition of an at least bivalent target competitor conjugate induces the formation of selectable signal-selection moiety complexes. Again, the formation of crosslinked complexes between signaling moiety and selection moiety is reduced by the addition of target.

Macromolecular targets are generally large enough to accommodate at least two non-overlapping binding sites for independent category specific binding moieties (including most proteins without multiple identical subunits and nucleic acid sequences without repeating sequences). Macromolecular targets without repeating sequences or determinants may be detected by the use of binding molecules, including category-specific binding molecules, which bind to non-overlapping regions on the target, allowing both the signaling moiety and the selection moiety to be complexed to the target without interfering with each other. Macromolecules with repeating sequences of amino acids or nucleotides, multimeric proteins with at least two identical sub-units, and viruses or cells with multiple copies of specific binding determinants can accommodate the binding of more than one category-specific binding agent on a single target, allowing but not requiring use of a single category-specific binding moiety conjugated to both the signaling moiety and the selection moiety.

8. Contacting

The contacting step allows the formation of a labeled target complexed with a selection moiety. Formation of the labeled target and of the target complexed with selection moiety can occur sequentially in any order, or may occur concurrently.

Those skilled in the art will appreciate that additional components may be added to improve the rate, reproducibility, stability or quality of the reaction. These additional components may include buffers to control the pH of the reaction, as well as diluents, detergents, and other additives to reduce nonspecific binding between components, enhance the availability of the target in the reaction, increase the efficiency of complex formation, or for other purposes. The rationale for and selection of additional components are discussed in references like Christopher Price & David Newman, Principles and Practice of Immunoassay.

The components of the reaction, including target, label, selection moiety, and additional components can be added to the reaction in a variety of physical configurations and degrees of pre-assembly and in a variety of sequences. If sequential reactions are desired, incubation of a first set of components can be carried out (e.g. a mixture of target, additives and label) before subsequent additions are made (for instance, of selection moiety and optionally additional additives). All components can be added in the liquid form with each component added separately to the reaction well. Alternatively, liquid components can be pre-mixed to allow fewer liquid addition steps. Additionally, some or all of the supplied components of the reaction (e.g. all components but the sample) can be lyophilized or dried before their addition to the reaction, and the drying can be carried out separately for each component or on a mixture of components. Drying can be carried out in many formats, including drying reagents in the form of a cake in the reaction well, drying reagents in bulk and dispensing dried powder, or lyophilizing unit-dose reagent spheres and dispensing spheres into the reaction well. Reconstitution of the dried reagent can be due to addition of sample alone, or the addition of sample and diluent. FIG. 2 illustrates some embodiments of component addition to the reaction.

Addition of the sample and reagent component(s) can be performed manually by the operator, automated through use of an instrument or cartridge to manipulate liquid flow, or a by a combination of automated and manual methods. Reagents can be supplied to the operator or to an automated instrument in bulk and dispensed at the time of reaction, or can be pre-dispensed onboard within a single-use reaction well or cartridge.

A mixing method can optionally be applied to the reaction to make the reaction uniform and/or increase the rate of reaction. Mixing might be effected by methods including agitation, inclusion of a mechanical mixer (for instance, a propeller) in the sample, or by externally applied ultrasound or piezoelectric mixing devices.

An incubation period is provided to allow the contacting reaction to occur preferably to completion, or optionally to a sufficient degree of reaction that, for the smallest quantity of target to be detected, detectable quantities of labeled target-selection moiety complexes can be deposited in the detection zone and imaged by the detector.

After the contacting step of the invention is carried out, the reaction mixture contains a series of reaction products, including labeled target-selection moiety complexes, labeled target which failed to bind selection moiety, target-selection moiety complexes which failed to bind label, along with unreacted target, label, and selection agent. These reactants and reaction products are generally dispersed in a uniform manner throughout the mixture.

9. Depositing

An embodiment of the invention involves depositing labeled target within the detection zone for imaging. As an alternative, the method of the invention may involve detection of a target competitor within the detection zone (the target competitor may or may not be deposited on the detection surface) as a proxy for the presence of the target in a sample. The mode of deposition used is a function of the type of selection moiety employed. Examples of selection modes are demonstrated in FIG. 3.

In the case of direct capture, the selection moiety consists of category-specific or non-specific binding moieties coated or conjugated within the detection zone, for instance, conjugated directly onto the inner surface of the imaging window or conjugated onto linkers or spacing polymers which are conjugated to the imaging window. In this case, contacting the target with the selection moiety and performing the deposition of complexes occurs in a single step.

In the case where filtration is the mode for depositing labeled filterable complexes into the detection zone, the size or other properties of the labeled target or labeled target-selection moiety complex lead to deposition of the labeled target or labeled target-selection moiety complex onto the filter which is placed within the detection zone.

Other modes of deposition require applying force to the selection moieties, including the set of selection moieties which are complexed to labeled target, causing them to be deposited within the detection zone. In the case of magnetic selection, a magnetically responsive selection moiety is deposited into the detection zone by the application of magnetic force. If the force applied is substantially uniform and has a vector of force orthogonal to the detection surface, for instance by placing the imaging well over an array of permanent magnets in an appropriate configuration deposition of labeled complexes can be essentially uniform across the detection window. Uniform deposition of labeled target across the detection area can be useful for enumerating targets in the reaction, as they are spread apart allowing enumeration of labeled objects. When magnetic force is non-uniform across the plane of the imaging window, the labeled complexes can be deposited in patterns within the detection zone (FIG. 3). For instance, use of a strong magnet of dimensions smaller than the dimensions of the imaging window can result in deposition of magnetically-responsive selection moieties, including those complexed with labeled targets, in a dot or pile inside the boundaries of the imaging window. This deposition of labeled targets in a non-uniform pattern can be useful for data analysis, as a plurality of labels detected within the deposition zone are components of labeled target-selection moiety complexes.

Density separation. Gravity can be used as the deposition force if the selection moieties used in the assay are more dense than the reaction liquid, and if the detection zone is at the bottom of the reaction well. In this case, deposition can be achieved by allowing the selection moieties, with any labeled target bound to them, to settle to the detection zone, where they can be imaged. Alternatively, a centrifugal force can be applied to dense selection moieties to accelerate their deposition to the detection zone. The shape of the reaction well can be used to control the pattern of deposition in density-mediated selection processes. A planar imaging area at the bottom of the well will lead to uniform deposition of dense selection moieties and the bound labeled target associated with them, making it easier to enumerate the objects in the resulting image. Non-planar surfaces can be designed to result in deposition of complexes at the lowest point in the reaction well, allowing geometrical discrimination between labeled targets bound to selection moieties and labels which are unbound in the reaction mixture (FIG. 3).

Deposition is not always required within the scope of the invention, in particular if the dimensions of the container in which the reaction is run allow all of the labels in the reaction to fall within the detection zone. In this case, other methods are used to distinguish labeled target-selection moiety complexes from unbound label.

10. Distinguishing Labeled Targets

The invention provides improved methods for distinguishing between signaling moieties deposited in the detection zone as a result of binding to target and label which is not bound to a selected target. Discrimination of bound from free label is a particular issue when label is present in great excess over target, as is required when assays of the invention are designed to have high sensitivity with a short incubation time. Improving the discrimination between bound and free label improves the sensitivity and the specificity of assays of the invention by reducing background signal (signal detected in an image which is not due to labeled target-selection moiety complexes). Complexes are physically concentrated in the detection zone by the deposition step above; however both unbound label within the detection zone and unbound label outside of the detection zone can contribute a detectable optical signal to the image.

Dye as an optical screen for imaging. The invention discriminates bound from free label without the use of washing steps, and thereby increases the ease of use of the invention. The incorporation of an appropriate dye into the assay of the invention can be used as an optical separation device to increase the discrimination of label in the detection zone from label that is not in the detection zone. When optical detection is used for imaging, and the reaction medium is substantially transparent to excitation light or other illuminating light, as well as to reflected or emitted light producing the imaging signal, it can be appreciated that unbound label which is outside of the detection zone can contribute a large nonspecific optical signal to the image. This is illustrated on the left images of FIGS. 9 and 11. Inclusion of a dye into the reaction before imaging can be used to reduce the signal produced by unbound label residing outside of the detection zone. Dye at an appropriate concentration allows detection of fluorescence in the detection zone at or near the detection surface, while masking the signaling contribution from unbound label in the remainder of the solution. In the case where the signaling moiety is fluorescent, the dye used can have an absorbance of light overlapping the excitation or emission wavelengths of the fluorescent signaling moiety, or can absorb both exciting and emitted light. FIG. 8 demonstrates the absorbance spectrum of one such dye, Chromotrope 2R, overlaid with the transmission profiles of the excitation and emission filters used for imaging detection of the Invitrogen yellow-green Fluospheres® used as signaling moieties in the example. FIG. 9 illustrates that the addition of Chromotrope 2R dye to the well shields the detection zone from signal arising from label outside of the detection zone. Surprisingly, it can be seen in the figure that addition of dye still allows the discrimination of fluorescent particles within the detection zone.

The concentration of dye added to the reaction can be manipulated to control the depth of the detection zone. At concentrations of dye which are preferred, signaling moieties within approximately 50-100 microns of the detection surface can be discriminated, while the contribution of signaling moieties further than approximately 100 microns from the detection surface is minimized. The efficiency of optical shielding provided by a dye relates to the capacity of the dye to absorb light, and to the number of dye molecules encountered by light passing through the sample (the path length). If the dye concentration is too low, signals from more of the overlying unbound signaling moieties will be detected, while if the dye concentration is too high, signals from labeled targets which are close to the imaging surface will be diminished. In effect, regardless of the depth of field of the imaging system, the concentration of dye used in the reaction can be used to optically define the detection zone.

Dye can be added to the reaction at any time during the reaction sequence. Some embodiments may incorporate dye as an additive in the reaction. In other embodiments, dye is added after the contacting step is complete. Dye can also be a component in the cushion embodiments described below.

The dye of the invention can be a single dye or a blend of dyes designed to absorb light at appropriate wavelengths; selection of an appropriate dye is a function of the signaling moiety used and the optical imaging system to be applied. For example, for yellow green fluorescent Fluospheres®, with an emission maximum of 515 nm, and an excitation maximum of 505 nm, using an imaging system with excitation bandpass filters 475+/−29.5 nm and emission filters of 535+/−25 nm, Chromotrope 2R or Acid Red 1 dyes are two examples of appropriate dyes to produce an optical shielding effect. Those skilled in the art will be able to find other dyes which are suitable for this purpose. References like Floyd Green's The Sigma-Aldrich Handbook of Stains, Dyes and Indicators (Aldrich Chemical Company, Inc. 1990) list many possible dyes with utility in the invention.

Other types of dyes useful for optical shielding of signaling can be envisioned. When the signaling moiety is distinguished by its color, dyes absorbing light in a wavelength complementary to the color to be detected would be expected to act as optical shields for embodiments of the invention. Light scattering particles may also be used as a "dye" for optical shielding of color reactions. Black particles, including black India ink, absorb light at a variety of wavelengths, and can also provide an optical shield.

In the case where iron-containing magnetic particles are used as selection moieties, the use of large numbers of magnetic particles in the reaction can deposit a layer of opaque particles in the detection zone. The passage of light through this layer is occluded, and only signaling moieties which reside between the magnetic particle layer and the imaging surface are imaged.

Use of a cushion to exclude unbound signaling moieties from the detection zone. In addition to signal contributed by unbound signaling moieties outside of the detection zone, which can be addressed by addition of dye, unbound label can also be found within the detection zone as a function of its random distribution throughout the reaction volume. This label is not optically distinguishable from specifically deposited signaling moieties in the image, and reduces the sensitivity of detection.

Within the method of the invention, unbound signal can be minimized within the detection zone by excluding unselected components of the reaction from the detection zone. This can be accomplished by placing a liquid layer which is of higher density than the bulk reaction, and which is at least as deep as the detection zone, between the bulk reaction and the imaging surface before beginning the process of depositing selection moieties into the detection zone. Use of a dense layer or "cushion" between the reaction mixture and the imaging window can be incorporated into the assay of the invention in several ways. It is preferred but not required that the bulk reaction have no direct contact with the imaging surface. The dense layer or "cushion" can be placed into an imaging well and the reaction mixture then layered above it. This is one preferred approach because it avoids contact between the reaction mixture and the detection surface, so that signaling moieties enter the detection zone only by deposition. In another preferred embodiment, the components required to produce a dense cushion are pre-dispensed into the imaging well and dried, so that the dried material is reconstituted during the incubation of the reaction in the contacting step above, and forms a dense underlayer filling at least the volume of the detection zone. In a less-preferred alternative, the dense cushion can be layered under the bulk reaction in the imaging well to occupy the detection zone before deposition of selection moieties is initiated.

In each case, the deposition of selection moieties, together with any labeled targets bound to them, causes the transport of the selection moieties out of the bulk reaction mixture and into the dense cushion layer residing within the detection zone. This process minimizes the quantity of unbound label found within the detection zone and therefore detectable by imaging.

A variety of dense materials can be used to constitute the dense layer within the detection zone. Liquids which are denser than water and immiscible with water are one alternative. Solutions containing high solute concentrations, like sucrose in concentrations of 7.5% w/v to 35% w/v, iodixanol, tradenamed Optiprep®, at concentrations of 10% or higher, more preferably at 15% or higher, most preferably at 15-30%, diatrizoate or Percoll® can be used to produce the dense underlayer. Other solutes which can be dissolved to produce solutions of high density might include NaCl, MgCl, Ficoll, CsCl, metrizamide, or albumin. It is preferred that the underlying solution be sufficiently different in density from the bulk reaction that mixing between the two layers is minimized, and that particulate components in the reaction do not sediment through the cushion spontaneously. For example, the underlying solution (the dense layer or cushion) may have a density that is at least 0.1, 0.2, 0.3, 0.4, 0.5, 1.0, 1.5, 2.0, 2.5, 3.0, 4.0, 5.0, 10.0, 12.0, 15.0, or 20.0 kg/L or more greater than the overlying layer. It is also preferred that the dense solution be low in viscosity to avoid impeding the deposition of labeled selection moiety complexes within the detection zone. The ability of a dense layer to maintain separation between an overlying bulk reaction and the imaging surface is illustrated in FIG. 8, where whole blood layered over a dense cushioning layer does not sediment to the bottom of an imaging well.

When the detector is configured so that only the detection zone is illuminated by the excitation source, a dense underlayer can be sufficient to permit selective imaging of signaling moieties in the detection zone. This might be accomplished by providing excitation light in a beam parallel to the plane of the detection window, and detecting a fluorescent signal through the detection window. This approach minimizes the optical contribution of the overlying signal moieties in the bulk reaction.

Dye cushion layers. The combination of the dense cushioning layer with the addition of dye provides an efficient reduction of background signal due to unbound signaling moieties in the reaction. The cushion prevents unbound signaling moieties from appearing in the detection zone, while the dye prevents the detection of signal due to unbound signal in the overlying bulk reaction, thereby isolating the signaling contribution of labeled targets complexed to selection moieties deposited within the detection zone. The cushion embodiments described above can be combined with the dyes of the invention for use in the dyed cushion embodiments of the invention. A direct example of the addition of dye to a cushion reagent is illustrated in FIG. 11. Examples of the use of dyed cushion are illustrated in examples 8 through 13 and 15 through 20 below. They demonstrate use of this format in a variety of sample types, including human whole blood, serum, plasma and urine with a variety of targets including human thyroid stimulating hormone, protein and polypeptide antigens of *B. anthracis*, and in the detection of *S. aureus* and methicillin-resistant *S. aureus* (MRSA) cells. Three different signaling moieties are used in the examples, including 0.5 μM fluorescent particles, 0.2 μM fluorescent particles, and SYBR nucleic acid staining.

The dyed dense layer occupying a volume at least equal to the volume of the detection zone can be placed in the imaging well, and the reaction mixture layered above it, before the deposition step of the invention is carried out. Alternatively, the materials required for formation of the dyed dense layer within the imaging zone can be dried into the imaging well in such a way that the reaction mixture reconstitutes the dyed dense layer during the incubation of the mixture to allow labeled target-signaling moiety complexes to form. While it is possible to underlay the dyed dense cushion layer between the reaction mixture and the imaging surface, it is preferred that the unbound label of the reaction mixture does not come into direct contact with the imaging surface during the reaction.

Photobleached detection zone. Another embodiment of the invention that does not require washing makes use of dye addition in a reaction where the fluorescent signaling moiety can be photobleached by exposure to light of the excitation wavelength of the fluorescent moiety. The reaction can be carried out in the imaging well. Dye is incorporated into the reaction either during the contacting step or after the contacting step of the reaction. Light is applied to the detection zone in such way as to photobleach the signaling moieties present within the detection zone without photobleaching the overlying signaling moieties. The deposition step is carried out, depositing labeled target-selection moieties into the detection zone where other fluors have previously been photobleached. When the detection zone is imaged, the detected signal is due to labeled target-selection moiety complexes, allowing sensitive detection of signal from the bound label fraction while excluding the signal from unbound label in a single reaction mixture without physical manipulation of the reaction liquids.

Another embodiment of the invention is useful in enumerating microbial cells in a sample. This embodiment uses photobleaching to differentiate the fraction of labeled target-selection moiety complexes due to target cells from the fraction due to reaction with soluble target in the reaction. An example would be a reaction detecting *S. aureus* cells by labeling the protein A on the bacterial cell wall with fluorescent particles which are not susceptible to photobleaching. Selection is accomplished by antibodies reactive with protein A on superparamagnetic microparticles. Samples containing *S. aureus* can also contain free protein A, which can cause formation of a labeled target-selection moiety complex in this format. If it is desired to know which signal detected in the image is due to cells in the reaction, and which is due to soluble material, the cells can be additionally labeled with a nucleic acid stain detectable by the same filter set as the signaling particles but susceptible to photobleaching. After deposition of labeled target-signaling moiety complexes through a dyed cushion into the detection zone, the detection zone is imaged, providing detection of both labeled cells and complexed signaling particles. The detection zone is then subjected to sufficient light to cause photobleaching of the labeled cells, and another image is acquired. The difference between the first image and the second defines complexes formed due to cells.

Distinguishing labeled target:selection moiety complexes by tracking movement. In an additional embodiment, separation of bound from free label can be performed making use of the fact that bound label takes on the selection properties of selection moiety to which it binds. For instance, fluorescent labeling particles complexed by target to magnetic particles gain the property of motion directed by a magnetic field. If the reaction is configured so that individual bound and unbound labels can be imaged, then when a magnetic field is applied with the vector of force in a direction substantially parallel to the imaging surface, the labels complexed with magnetic particles move in the direction of the magnetic force, while unbound labels move at random. If a long exposure is used for imaging, each of the moving labels can be seen as a streak or "comet" on the image. This embodiment is illustrated in Example 21. Alternatively, a series of images can be obtained during the time period when motion is directed by the magnetic field, and the motion of labels can be tracked through the video record of the motion.

One advantage of this assay embodiment is that it is non-destructive and can therefore be used to determine the kinetics of the binding reaction. During the initial stages of the reaction between target, label and selection moieties, a small amount of labeled target will be observed moving in response to the application of selective forces. As the reaction progresses, increasing quantities of label will become responsive to selective forces. Additionally, the direction of the force vector can be varied while keeping the force substantially parallel to the plane of the detection surface, allowing confirmation of the magnetic responsiveness of the signaling moieties under observation.

This assay embodiment could also be constructed using dense particles as the selection moiety. The reaction well could be configured with a detection window at the center of a reaction chamber. The chamber, designed so that individual bound and unbound labels can be imaged, when oriented with the detection window in the vertical position, allows the dense particles to settle due to the force of gravity, thereby flowing past the vertically oriented detection window. Images are acquired to determine the fraction of dense particles carrying a bound label, or the frequency of bound label moving in the direction of gravitational force, parallel to the plane of the detection window. These images can be in the form of single images with long exposure allowing analysis to track the motion of signaling moieties through production of a streak or "comet" oriented in the direction of the force vector on the image, or video sequences. The cartridge could be inverted like an hourglass, providing both the potential for a series of observations on the number of signaling moieties which become responsive to gravity, and a continued mixing of the reaction due to the settling of the dense particles.

11. Detection

In the method of the invention, labeled target-selection moiety complexes deposited in the detection zone are detected by use of digital imaging. A digital imager appropriate for detection of the signaling moieties must be provided. If the signaling moiety is fluorescent or phosphorescent, appropriate excitation light sources and excitation and emission filters are also provided. If the signaling moiety is chemi- or bio-luminescent, or chromogenic, the dense cushion will also contain appropriate substrates and co-factors for the production of signal.

Detectors for use in the invention include any detector which can produce a digital image of the label present in the detection zone when supplied with appropriate lenses, optical filters and illumination sources. Detectors might include CCD cameras, CMOS cameras, line scan cameras, CMOS avalanche photodiodes (APD's), photodiode arrays, photomultiplier tube arrays, or other types of digital imaging detectors.

The detector is used to generate one or more digital images of the detection zone. These can include one or a series of single images or a set of sequential images (e.g. video).

Imaging can be carried out under a single set of imaging conditions or the imaging conditions can be altered between images. For instance, multi-color fluorescent imaging can be used to detect a multiplexed assay where separate and optically distinguishable signaling moieties are each used to detect a distinct target. To image multiple fluors, the wavelengths of excitation light and the filter sets for emitted light can be varied to image a series of different signaling moieties in the same reaction well.

In some cases, sequential images can be used to distinguish debris. In the case of a signaling moiety which is susceptible to photobleaching, an initial image can be acquired which detects the signal due to the signaling moiety but which also contains debris which can be detected by intrinsic fluorescence or light scattering. After providing sufficient excitation light to photobleach the signaling moiety, a second image can be obtained. Fluorescent signal in the second image is due to debris and can be eliminated from the analysis of specific target capture. Example 23 provides an illustration of this approach to debris detection.

12. Analysis

The use of digital imaging can expand the dynamic range of an assay of the invention. In a preferred embodiment of the invention, each captured target deposited in the detection zone can, when imaged, result in the production of a detectable object in the digital image. When few enough objects are present in the image for separate bright objects to be detected, the individual objects can be identified as blobs in the image and enumerated. This approach allows accurate counting of low numbers of signal moieties even when the total signal detected occupies only a small proportion of the total pixels in the image. If the total signal in every pixel in the image were integrated across the image, the specific signal would be lost by averaging it with the noise of a much larger number of pixels with intensity in the background range. As the number of detected objects increases, the signal from these objects begins to merge, and simple object enumeration becomes inaccurate. In this case, the total intensity of the signal can be integrated, allowing accurate quantification and use of the complete dynamic range of the imaging device.

Standard curves can be used to relate the signal derived from analysis of digital images of the samples containing unknown quantities of target to the signal produced with known levels of targets. In the case of non-competitive assay embodiments, the specific signal increases with the number of targets present in the sample. In the case of competitive assays, the signal decreases as the quantity of target present in the sample increases.

Detecting sample interference by inclusion of parallel internal controls. It is well known that some samples can interfere with the detection of target, even under the most optimal analysis conditions. This interference can be positive, causing a high signal in the absence of target, or negative, causing an assay to fail to detect a positive sample. The addition of internal controls run in parallel with the test sample in the actual sample matrix can be used to distinguish true and false test results. A representation of this control scheme is diagrammed in FIG. 26. A positive control (for instance, adding a predetermined quantity of target to the test sample) would be expected to add a definable incremental signal when the control is added to the test sample. If the positive control is not detected, the sample can be considered to have a negative interference and interpreted appropriately. Similarly, a negative control, designed to inhibit the production of signal due to target in the sample (for instance, by adding a large quantity of the category-specific binding moiety used to bind label to the target), should result in a reduction of the signal produced by a positive sample. A positive sample which does not demonstrate a decreased signal in the negative control well is either a false positive or an extremely high true positive. These alternatives can be distinguished by dilution of the sample. The negative control could alternatively contain an irrelevant (signaling moiety-specific capture moiety complex) which does not react with the target. Example 16 illustrates assays carried out using parallel internal positive and negative controls.

13. Assembly

The reactions of the invention can be presented to the user in a variety of fashions. In general, each of the components required for the detection of target according to the invention will be provided to the user, who will supply the sample to be tested for the presence of target. These components include:

Components of the contacting reaction:
  A reaction well either separate from or combined with an imaging well
    signaling moiety conjugated to a binding moiety as required for the detection of target
    selection moiety conjugated to a binding moiety as required for the detection of target
    Additives required for optimal performance of the reaction
  Dye, cushion and/or dyed cushion to optically and/or physically separate the bulk reaction from the detection zone In one set of embodiments, the components of the reaction are combined with sample in a reaction well. After all reactants have been mixed with the sample the reaction is transferred to an imaging well before deposition of selection moieties into the detection zone and imaging. Each of the liquid components can be added to the reaction well as individual additions. This method of assembly is embodied in the high-throughput surge testing instrument of Example 13. Alternatively, liquids can be combined and added to the reaction as one or two additions, reducing the number of dispensing steps required to carry out the invention. The dye, cushion, or dyed cushion can be dispensed as a liquid into the imaging well, with the reaction mixture overlaid above the cushion, as demonstrated in Example 13, or can be dried in the imaging well, and rehydrated by the addition of the reaction mixture. The components of the reaction can alternatively be pre-dispensed into the reaction well in dried or lyophilized form, rehydrated by the addition of sample or diluent plus sample and then transferred to dye, cushion, or dyed cushion in the imaging well. Drying can be carried out in many formats, including drying reagents in the form of a cake in the reaction well, drying reagents in bulk and dispensing dried powder, or lyophilizing unit-dose reagent spheres and dispensing spheres into the reaction well.

The practice of the invention is greatly simplified when all of the components including the dyed cushion are pre-dispensed and dried in a single reaction/imaging well. The dyed cushion can be dried adjacent to the detection surface, so that it rehydrates during the reaction and protects the imaging surface from the reactants. Dried reaction components can be provided in a form that rehydrates instantly upon the addition of sample, a diluent, or sample plus diluent, and forms a separate layer above the rehydrating dye cushion. The reaction components can be in the form of a cake layered directly above the dried cushion, as demonstrated in Example 20, or can be dried separately as unit dose reagent spheres (Example 19) or as bulk reagents dispensed into the reaction well above the dried dyed cushion. In this embodiment, a single liquid addition is sufficient to carry out all of the steps of the invention, and no transfer of reagents from one vessel to another is required. This format is amenable to being carried out manually, by an automated instrument, or by fluidic transfer within a self-contained cartridge.

Addition of the sample and reagent component(s) can be performed manually by the operator, automated through use of an instrument or cartridge to manipulate liquid flow, or a by a combination of automated and manual methods. Reagents can be supplied to the operator or to an automated instrument in bulk and dispensed at the time of reaction, or can be pre-dispensed onboard within a single-use reaction well or cartridge.

EXAMPLES

The invention is further described with respect to the following nonlimiting embodiments. Unless otherwise noted, any element of a method specifically described in the examples may be employed generally with a method of the invention. Additional detail on imaging analyzers, software, and devices for carrying out the methods are also described in International Application No. PCT/US2009/58274, titled "Imaging analyzer for testing analytes," filed Sep. 24, 2009, and International Application No. PCT/US2009/058237, titled "Kits and devices for detecting analytes," filed Sep. 24, 2009, both of which are hereby incorporated by reference.

Example 1

Labeling of *Staphylococcus aureus* with Fluorogenic DNA Stain

This example describes the labeling of *S. aureus* bacterial cells with a fluorogenic DNA stain which demonstrates a method to label bacterial targets for detection by imaging. Labeling bacterial targets is important in a number of analytical situations as applied in clinical, industrial, and environmental analysis. Use of bacterial labeling with fluorogenic dyes has a general use in the context of the invention because of the prodigious signal that can be generated allowing the bacteria to be easily enumerated using non-magnified imaging.

Method. Labeling of *S. aureus* with SYTO-13® was carried out as follows. A culture of *S. aureus* (ATCC strain 29213) was grown in Tryptic Soy Broth (Acumedia, Catalog No. 7164A) at 35° C. for 2 hours to achieve log-phase growth. The cell numbers were counted in a counting chamber on Zeiss microscope and diluted to $1.67 \times 10^8$ cells/mL in a PBS-TBP solution (10 mM Phosphate, 140 mM sodium chloride, 3 mM Potassium Chloride (Calbiochem, Catalog No. 524650), 0.05% w/v Tween 20 (Acros, Catalog No. 2333600010), 2 mg/mL Bovine serum albumin (Sigma-Aldrich, Catalog No. A3059) and 0.05% v/v Pro-Clin™ 300 (Supelco Catalog No. 48912-U) adjusted to pH 7.4. SYTO-13® (Invitrogen/Molecular Probes, Catalog No. S7575) was diluted 1:20 with saline solution (0.9% w/v Sodium Chloride, J T Baker, Catalog No. 3629-07). The labeling reaction mixture contained 6 µL diluted *S. aureus* cell solution, 10 µL of the diluted SYTO-13® solution and 984 µL PBS-TBP. The reaction mixture was incubated for 2 min. The sample was then analyzed on a Partec Cyflow flow cytometer set to trigger on green fluorescence at an emission wavelength of 520 nm with the gain set at 300.

Results. FIG. 4 shows the log fluorescence intensity of *S. aureus* cells not labeled with SYTO-13® (left) versus cells labeled with SYTO-13® (right). It can be seen that labeled cells are readily detected by fluorescence at 520 nm.

Conclusions. The result in example 1 demonstrates that bacterial cell targets can be fluorescently labeled with a high intensity.

Alternative embodiments. Later examples will demonstrate that bacteria labeled with nucleic acid stains like SYTO-13® are detectable by non-magnified imaging techniques. Other nucleic acid stains may be used in a similar fashion to fluorescently label bacterial cells with fluorescent excitation and emission at a variety of wavelengths; these stains include other members of the SYTO® family of stains (Invitrogen) and members of the SYBR® family of nucleic acid stains, propidium iodide, or hexidium iodide. This type of staining method labels all nucleic acid containing cells in a sample. The specificity of the assay for a particular category of targets can be enhanced by combining the nucleic acid-based labeling of cells with a category specific selection method, as seen in examples below. This allows, for example, detection of one particular category of cells from a mixture of labeled cells, resulting in a target specific assay, for example detection of *S. aureus* in a mixed bacterial culture from a wound. A variety of selection methods are described below as alternative embodiments in example 4 (e.g. *S. aureus* can be labeled with SYTO-13® and selected with magnetic particles conjugated with anti *S. aureus* antibodies, through a dye-cushion reagent see example 18 below). Other types of chemical classes could be labeled by this approach and detected by specific selection followed by imaging; an example is labeling of lipids within human serum lipoproteins with Nile Red followed by selection of low-density lipoproteins specifically with magnetic particles conjugated with anti-human apolipoprotein B antibodies. This allows the determination of the lipid content of low-density lipoprotein complexes in a sample. Many similar embodiments can be readily contemplated.

Labels with different signal characters can be used (e.g. fluorescence, chemiluminescence, light absorbing, light scattering, phosphorescence, enzymatic reactivity and Raman scattering). Different signaling moieties can be also used (with different signaling character) e.g., fluorescein diacetate (fluorescent esterase substrate), SYBR® Green® (fluorescent DNA stain), Sudan black (lipid staining), enzyme substrates that resulting insoluble products, polystyrene particles, polystyrene particles containing fluorescent dyes, colloidal gold and others.

The method described can be used in the labeling of targets which can include, but are not limited to: cells, viruses, organelles, lipoproteins, and molecules including proteins, oligonucleotides, lipids, oligosaccharides, and small organic and inorganic molecules.

Samples can also be processed prior to labeling—e.g. Cells can be fixed with methanol. DNA can be extracted and purified.

Example 2

Manufacture of Fluorescent Particles Conjugated with Chicken Anti-*Staphylococcus aureus* Protein A Antibody This example describes the manufacture of fluorescent particles conjugated with chicken anti-*S. aureus* protein A antibodies. These particles serve as specific labels for *S. aureus*, as they comprise signaling moieties that are complexed with category binding moieties and therefore specifically bind target. Target-specific fluorescent particles have general use in the context of the invention because these particles emit a prodigious signal and can be easily enumerated using non-magnified imaging.

The particles can be used in methods to detect and enumerate individual cellular and molecular targets at low concentrations in many samples including clinical, industrial, and environmental samples. The method can also be used to improve the signal stability in complex matrices (e.g. the use of fluorescent particles can reduce quenching by non-target components in a sample).

Method. Carboxylated yellow-green fluorescent particles (FluoSpheres) having 200 nm diameter (Invitrogen, Catalog No. 8811) were washed and resuspended to 1% w/v in 50 mM 2-morpholinoethanesulfonic acid (Aldrich, Catalog No. 69889) adjusted to pH 5.5. The microparticles were then activated by sequential addition of Sulfo-N-hydroxysuccinimide (Thermo Pierce, Catalog No. 24510) and 1-ethyl-3-(dimethylaminopropyl)carbodiimide (Thermo Pierce, Catalog No. 22980) each at a final concentration of 2 mg/mL and incubated for 30 minutes. The particles were washed and chicken anti-*S. aureus* Protein A antibody (Meridian OEM, Catalog No. C5B01-296) was slowly added to a final concentration of 2.0 mg/mL; this mixture was incubated with mixing for 16 hours at room temperature. The mixture was then mixed 1:1 with a 50 mg/mL solution of bovine serum albumin (Sigma-Aldrich, Catalog No. A3059) and incubated for 2 hours. After incubation a solution of 1 M ethanolamine (Sigma-Aldrich, Catalog No. E9508) adjusted to pH 8.0 was added so that the final concentration of ethanolamine was 100 mM and the mixture incubated for 1 hour. The antibody derivatized fluorescent microparticles were then washed and resuspended in a solution of 20 mM Tris (JT Baker Catalog No. 4109-02), 0.05% w/v Tween 20 (Acros Catalog No. 2333600010), 2 mg/mL Bovine serum albumin (Sigma-Aldrich, Catalog No. A3059), 0.05% w/v ProClin 300 (Supelco, Catalog No. 48912-U) with the pH adjusted to 7.8 and sonicated briefly to ensure the particles were monomeric as confirmed by Partec Cyflow flow cytometer.

Alternate Embodiments. There are a multitude of methods for the manufacture of a signaling moiety complex. Category binding moieties can be passive adsorbed or linked through non-covalent or covalent chemical links (e.g. antibodies can be passively adsorbed onto polystyrene particles, linked through a non-covalent biotin-streptavidin link or through covalent links between protein amino groups and particle carboxylate groups on carboxylated particles via carbodiimide chemistry). Many useful conjugation methods are known (Bioconjugate Techniques Hermanson 1996 Academic Press).

Different category labeling moieties can be used including but are not limited to: Antibodies (including various immunoglobulin types) and other proteins (e.g. lectins, hormone receptors and others), Oligonucleotides and their synthetic analogs (e.g. peptide nucleic acids, aptamers and others), Oligosaccharides (e.g. heparin and others), Organic polymers (e.g. dextran sulfate and others) and Small molecules (e.g. drugs, non-peptide hormones, biotin, dyes and others)

Specific labels having a variety of specificities can be manufactured. The specificity of an assay using fluorescent particles as the signaling moiety is controlled through the selection of the category binding molecules conjugated to the particle surface. For instance, use of anti-TSH antibodies produces a fluorescent particle which labels TSH and allows its detection by imaging.

The method described can be used in the labeling of targets which can include, but are not limited to: cells, viruses, organelles, lipoproteins, and molecules including proteins, oligonucleotides, lipids, oligosaccharides, and small organic and inorganic molecules.

Specificity of the assay for a target can be enhanced by combining labeling of a target with a target specific selection method (as discussed in example 1 and described in examples 6, 9-19, 21-24).

Different signal characters can be used e.g. fluorescence, chemiluminescence, light absorbing, light scattering, phosphorescence, enzymatic reactivity and Raman scattering.

Particles of different signal signatures can be conjugated to distinct category specific binding molecules to allow simultaneous detection of multiple targets in a single reaction. Different signaling moieties can be also used (with different signaling character) e.g., fluorescein diacetate (fluorescent esterase substrate), SYBR® Green (fluorescent DNA stain), Sudan black (lipid staining), enzyme substrates that yield insoluble products, polystyrene particles, polystyrene particles containing fluorescent dyes, colloidal gold and others.

Example 3

Labeling of Staphylococcus aureus Cells with Fluorescent Nanoparticles that Bind Specifically to Protein A on the Cell Surface This example describes a method for labeling of S. aureus bacterial cells with target-specific fluorescent particles. Use of target-specific fluorescent particles has general use in the context of the invention because these particles emit a prodigious signal and can be easily enumerated using non-magnified imaging. The method can thus be used to detect and enumerate individual cellular and molecular targets at low concentrations in clinical, industrial, and environmental samples.

The example demonstrates using flow cytometry that S. aureus can be labeled with target-specific fluorescent particles.

Method. S. aureus cells were labeled with anti-protein A antibody coated fluorescent particles manufactured as described in Example 2. A culture of S. aureus (ATCC strain 29213) was grown in Tryptic Soy Broth (Acumedia, Catalog No. 7164A) at 35° C. for 2 hours to achieve log-phase growth ($OD_{600}$=0.3). The S. aureus cells were counted in a hemocytometer on a Zeiss microscope and cells were diluted to $1 \times 10^7$ cells/mL in PBS-TBP solution. These cells were stained with hexidium iodide (Molecular Probes, L-7005) by incubating 1 mL of diluted cells with 1.5 µL of 4.67 mM hexidium iodide at room temperature for 10 minutes.

A series of S. aureus labeling reaction mixtures were constructed with the number of input antibody coated fluorescent particles varying within the series. Each 50 µL mixture contained 30 µL of PBS-TBP, 10 µL of hexidium iodide stained S. aureus cells ($1 \times 10^7$ cells/mL) and 10 µL of antibody-coated fluorescent particles from example 2 at concentrations from $0.5 \times 10^{10}$ to $5 \times 10^{10}$ particles/mL. The reaction was incubated for 30 min at room temperature. After the incubation, the reaction mixture was diluted to 1 mL of PBS-TBP and incubated for an additional 2 min. The sample was then analyzed on a Partec Cyflow flow cytometer set to trigger on Red Fluorescence an emission wavelength of 590 nm with the gain set at 395. The number of fluorescent particles captured for each hexidium labeled cell was calculated from measurements of the fluorescence of single particles.

Results. FIG. 5 shows the results of labeling of S. aureus cells using $1 \times 10^{10}$ antibody coated fluorescent particles/ml. Panel A shows the histogram of the reaction which have only S. aureus cells, Panel B shows the histogram of the reaction which have only fluorescent particles and Panel C shows the histogram of the reaction which contained S. aureus cells and fluorescent particles. It is clear from the data that fluorescent signal at 520 nm was only observed when reaction mixture contained cells and fluorescent articles (Panel C). The cells only or fluorescent particles only did not give any signal above the background (Panels A and B). FIG. 6 shows the dependence of fluorescent cell labeling, indicated by the average number of bound particles per cell, on the concentration of fluorescent particles used to label. The labeling is nearly saturated with the addition of $2 \times 10^{10}$ cells per ml of fluorescent particles. At all particle concentrations used, multiple particles were bound to each S. aureus cell.

Conclusions. This data demonstrate the use of antibody-coated fluorescent particles to specifically label cells (e.g. S. aureus). As shown in subsequent examples, the labeling method used here can be combined in the context of the invention with methods for discriminating labeled target from free signaling moieties and other labeled entities. The results show the prodigious labeling that can be obtained with the method with as many as 18 fluorescent particles per S. aureus cell.

Alternative embodiments. Other types of detectable specific labels can be used in this example, including fluorescent particles of different diameters or of different signaling signatures. Other signaling moieties could be used in the production of specific labels; for instance, Alexa® 490 fluorescently labeled antibodies could be used for S. aureus detection.

Labels with different signal characters can be used (e.g. fluorescence, chemiluminescence, light absorbing, light scattering, phosphorescence, enzymatic reactivity and Raman scattering).

The method described can be used in the detection of targets which can include, but are not limited to: cells, viruses, organelles, lipoproteins, and molecules including proteins, oligonucleotides, lipoproteins, lipids, oligosaccharides, and small organic and inorganic molecules.

This labeling method combined with the use of specific selection moieties can be used for imaging-based detection of S. aureus cells.

Samples can also be processed prior to labeling—e.g. Cells can be fixed with methanol. DNA can be extracted and purified.

Example 4

Manufacture of Magnetic Particles Conjugated with Anti-Protein A Antibodies

Example 4 describes the manufacture of magnetic particles conjugated with antibodies against the Protein A of S. aureus for use as a specific selection agent in the detection of S. aureus cells. This example describes the manufacture and functionality testing of a specific selection moiety that binds to targets.

Specific selection moieties can be used in combinations with labels to produce a labeled target-selection moiety complex. When deposited in a detection zone, these complexes can be detected by imaging-based detection methods.

The method can be used to select, and concentrate targets out of complex samples (e.g. biological fluids like blood, and urine, or milk, wastewater, industrial products, and others).

Methods. The method for manufacturing magnetic particle particles conjugated with chicken anti-*S. aureus* Protein A antibody and their functionality testing is described below. Carboxylated magnetic particles, 292 nm diameter (Ademtech, Catalog No. 0213) were washed and resuspended to obtain 1% w/v suspension in 50 mM 2-Morpholinoethanesulfonic acid (Aldrich, Catalog No. 69889) adjusted to pH 5.5. The microparticles were then activated by sequential addition of Sulfo-N-hydroxysuccinimide (Thermo Pierce, Catalog No. 24510) and 1-ethyl-3-(dimethylaminopropyl)carbodiimide (Thermo Pierce, Catalog No. 22980) each at a final concentration of 2 mg/mL, and were incubated for 30 minutes. The particles were then washed and chicken anti-*S. aureus* Protein A antibody (Meridian OEM, Catalog No. C5B01-296) was slowly added to achieve final concentration of 0.5 mg/mL. This mixture was incubated with mixing for 16 hours at room temperature. Following incubation, the reaction mixture was mixed with an equal volume of 50 mg/mL solution of bovine serum albumin (Sigma-Aldrich, Catalog No. A3059) and further incubated for 2 hours. After incubation, a solution of 1 M Ethanolamine (Sigma-Aldrich, Catalog No. E9508) adjusted to pH 8.0 was added so that the final concentration of ethanolamine was 100 mM and incubated for 1 hour. The antibody conjugated magnet microparticles were then washed and resuspended in a solution of PBS-TBP and sonicated briefly to ensure the particles were monomeric. After manufacturing, the antibody-coated magnetic particles were tested for their capture efficiency using *S. aureus* in a bioassay as follows. A culture of *S. aureus* (ATCC strain 29213) was grown in Tryptic Soy Broth (Acumedia, Catalog No. 7164A) at 35° C. for 2 hours to achieve log-phase growth. The cell numbers were counted in a hemocytometer on a Zeiss microscope and diluted to $1.57 \times 10^5$ cells/mL in a solution of PBS (10 mM Phosphate, 140 mM sodium chloride, 3 mM Potassium Chloride (Calbiochem Catalog No. 524650) adjusted to pH 7.4). The chicken anti-*S. aureus* Protein A antibody magnetic particles were diluted in PBS to a series of concentrations from $0.625 \times 10^9$ to $5 \times 10^9$ particles/mL. For each 50 µL reaction, 10 µL diluted *S. aureus* cells (10,000 cells), 10 µL of magnetic particles and 30 µL PBS were mixed and incubated for 15 min. After incubation, 20 µL of each reaction mixture was overlaid on 70 µL of cushion solution (consisting of 30% OptiPrep® Sigma Cat. No. D1556) in the wells of a 96-well half-area diameter clear plate (Greiner, Cat. No. 675001). The magnetic particles, and the cells bound to them were magnetically selected using a bar magnet apparatus for 4 min. After magnetic selection, the top layer, containing unselected cells, was carefully removed, and then the portion of the solution containing magnetically selected cells (bottom) was reconstituted with PBS. Aliquots of both the solutions were then plated on tryptic soy agar plates and incubated overnight at 32.5° C. The next day the number of colonies on each plate were counted by eye and the magnetically captured *S. aureus* cells (CFU) were calculated with the following formula Percent magnetically captured CFU=[number of colonies magnetically captured/(number of colonies magnetically captured+number of colonies not magnetically captured)]× 100.

Results. FIG. 7 shows the magnetic capture of *S. aureus* CFU as a function of the number of magnetic particles added to the assay. These results demonstrate that *S. aureus* cells could be specifically captured using anti-protein A antibody coated magnetic beads.

Conclusions. The results demonstrate the use of Chicken anti-*S. aureus* Protein A antibody conjugated magnetic particles for the selection of *S. aureus* cells, using a method of detection of the selection process which is independent of the labeling of cells. This example teaches a method for the manufacture of the selection moiety of the invention. Other selection moieties and their manufacture are readily contemplated.

Alternative embodiments. When combined with an appropriate method of labeling of *S. aureus* target cells, this selection method can be used to detect the presence of *S. aureus* in a sample by an imaging-based detection method. Other modes of selection can used including: density (selection by gravity or centrifugation), filtration, capture on the imaging well surface, and charge (electrophoresis). If other selection modes are used, different selection moieties would be conjugated to the anti-protein A antibody. In some embodiments, selection can be performed without instrumentation (e.g. selection by gravity).

Other types of selection moieties can be used for magnetic selection, including paramagnetic particles of different diameters and composition (e.g. metals, including iron, nickel, cobalt and others, ferrofluids).

Various manufacturing methods can be used to link category binding moieties to selection moieties (as described in, e.g., the alternative embodiments in example 2 for signaling moieties).

Different category labeling moieties can be used include but are not limited to: Antibodies (including various immunoglobulin types) and other proteins (e.g. lectins, hormone receptors and others), Oligonucleotides and their synthetic analogs (e.g. peptide nucleic acids, aptamers and others), Oligosaccharides (e.g. heparin and others), Organic polymers (e.g. dextran sulfate and others) and Small molecules (e.g. drugs, non-peptide hormones, biotin, dyes and others).

The selection may be specific through selection of a specific target within a category (e.g. selection of human Thyroid stimulating hormone from blood or *S. aureus* cells from nasal samples). The assay may be also specific through selection of a labeled category of targets (e.g. Selection of Lipoproteins from Human plasma).

The method described can be used in the selection of a variety of targets which can include, but are not limited to: Cells, viruses, organelles, lipoproteins, and molecules including proteins, oligonucleotides, lipids, oligosaccharides, and small organic and inorganic molecules.

Example 5

Assay of Human Thyroid Stimulating Hormone in Human Serum

This example demonstrates the use of dye for reduction of signal background in an assay that does not include a washing step. It combines use of specific labeling of the target by antibody coupled fluorescent particles with specific selection of targets through use of antibody coupled magnetic particles. The addition of dye to the reaction allows the detection of signaling moieties in the detection zone while eliminating the signal due to unbound particles in the reaction residing outside of the detection zone. In this example, the assay of Human Thyroid Stimulating Hormone (hTSH) in human serum uses labeling with mouse monoclonal anti-hTSH antibody coated fluorescent particles combined with magnetic selection with mouse monoclonal anti-hTSH antibody coated magnetic particles imaged in the presence of a dye is described.

The specificity of the assay is enhanced by inclusion of a dye which absorbs at the excitation and/or emission wavelength of the fluorescent moiety in use as the signaling moiety. This dye restricts the ability to image signaling target complexes to the detection zone. The spectrum for Chromotrope 2R is shown in FIG. 8. The solid line shows the measured absorbance spectrum of the dye Chromotrope 2R. The transmission profile of the excitation and emission filters used in the imager are indicated by brackets, which span the FWHM specification of the filters.

Method. In this experiment, it is shown that dye reduces the signal from fluorescent microparticles. Wells were formed on microscope slides with an adhesive silicone gasket (Grace) that were 2 mm in diameter. An aliquot of 40 µL of fluorescent particles Invitrogen catalog No. 8813), with or without 5.5 mg/mL Chromotrope 2R in the solution (Sigma-Aldrich C3143). The wells were then imaged in a high throughput automated image analyzer. This method describes the protocol for immunoassay of hTSH in human serum using magnetic capture and fluorescent particle labeling in the presence of dye without washing. Anti-hTSH coated fluorescent particles were prepared as described in Example 2 with the following modifications: 500 nm fluorescent particles (Invitrogen Catalog No. 8813) were used and the antibody was a mouse monoclonal anti-hTSH (Meridian OEM cat. # MAT04-005). Anti-hTSH coated magnetic particles were prepared as described in example 4 with the following modifications: the antibody was a mouse monoclonal anti-hTSH (Thermo Seradyn cat. # MIT-0409). Experimental samples were made by spiking known amounts of recombinant hTSH (Cell Sciences, Catalog No. CRT505B) into pooled human serum previously depleted of endogenous TSH. The reaction was carried out in a 96 well microtiter plate. The reaction (50 µL) contained 2 µL of fluorescent particles (0.02% w/v) coated with anti-hTSH antibody, 2 µL of magnetic particles (0.25% w/v) coated with anti-hTSH, 21 µL of 200 mM EPPS buffer containing 400 mM 1,3 Diaminopropane pH 7.8 and 25 µL of serum samples containing different concentrations of hTSH. After mixing the reaction components, the reaction was incubated at ambient temperature for 10 min to allow the formation of 'sandwich' immunocomplexes of hTSH with fluorescent particles and magnetic particles. After incubation, 50 µL of 25 mg/mL dye solution (Chromotrope 2R (Sigma-Aldrich C3143), 0.5% w/v fish gelatin (Sigma-Aldrich Catalog No. G7765) in PBS-TBP was added to the well. The plate was then placed on a magnet array in which a magnet is located at the center bottom of each well. After 10 minutes to allow the magnetic selection of the magnetic particle-hTSH-fluorescent particle complexes, the plate was imaged on an automated imaging analyzer and at an exposure time of 0.1 sec. Individual fluorescent particles were then enumerated using imaging software. Another experiment took the reaction mixture above and pipetted aliquots on top of cushion layers with and without Chromotrope 2 R present.

Results. FIG. 9 are images of wells with and without dye as described in the second experiment above and demonstrate one embodiment of the invention in which a dye is used to restrict detection of selected target-signaling moiety complexes to the detection zone. The data in FIG. 10 shows the dose response curve of the hTSH immunoassay indicating that the immunoassay could be carried out without incorporating washing steps by performing non-magnified imaging in presence of dye.

Conclusion. This result indicated that use of dye, as an embodiment of the invention, allows users to perform the immunoassay without washing step to remove un-reacted signaling moieties. The method described allows detection of targets in complex matrices at a low concentration (FIG. 10) through the combination of a signaling complex, selection moiety, and dye that reduces background from free signaling moiety and non-selected signaling moiety non-target complexes outside the detection zone.

Alternative embodiments. The methods of this example could be used to detect a wide variety of targets by substituting other appropriate category-specific binding moieties for the anti-TSH antibodies used in the example. In other embodiments different signal characters can be used e.g. fluorescence, chemiluminescence, light absorbing, light scattering, phosphorescence, enzymatic reactivity and Raman scattering, with the selection of appropriate dyes. For example the dye Toluidine Blue O could be used with the fluorescent label Texas Red (sulforhodamine).

Example 6

Reduction of Assay Background Using Dye-Cushion Reagent which Allows Performing the Complete Assay without any Washing Step to Remove Unreacted Assay Reactants with Non-Magnified Imaging In this example, dye-cushion reagents (e.g., a reagent containing a mixture of a dye and a density agent) useful in the practice of the invention are described. The example provides instruction for the preparation and demonstrates attributes of dye-cushion reagents that can be used to reduce assay backgrounds and perform an assay in one vessel without washing to separate the assay reactants.

Unbound signaling moiety residing outside of the detection zone can create a background in non-magnified imaging of targets. This background can be reduced by addition of a dye that restricts imaging to the detection zone (example 5). In the current example, we use a combination of a dye with a density agent to further reduce signaling background by excluding unbound signaling moieties from the detection zone, allowing detection only of signal which is deposited in the detection zone due to the selection process.

Methods. Sucrose dye-cushion reagent was made using a solution of 2 mg/mL of Chromotrope 2R (Sigma-Aldrich Catalog No. C3143) and 60% wt/wt sucrose (JT Baker, Catalog No. 4097-04) in Tris-TBP. Optiprep® dye-cushion reagent was made using a solution of 2 mg/mL of Chromotrope R2 (Sigma-Aldrich cat#C3143) and 25% v/v Optiprep® (Sigma-Aldrich, Catalog No. D1556) in Tris-TBP.

In one experiment, the reaction mixture (50 µL) containing 2 µL of fluorescent particles (0.02% w/v) coated with anti-hTSH antibody, 2 µL of magnetic particles (0.25% w/v) coated with anti-hTSH, 21 µL of 200 mM EPPS buffer containing 400 mM 1,3 Diaminopropane pH 7.8 and 25 µL of serum samples containing different concentrations of hTSH. After mixing the reaction component, the reaction was incubated at ambient temperature for 10 min to allow the formation of 'sandwich' immunocomplexes of hTSH with fluorescent particles and magnetic particles. After incubation, 25 µL of reaction mixture was layered onto 30 µL of cushion reagent with and without the Chromotrope R2 dye component in a black microplate with a clear bottom (Corning 3881). The wells were imaged on a high throughput automated imaging analyzer.

In separate experiment, the above reaction mixture (25 µL) was layered onto dye cushion reagent (with Chromotrope R2 dye). The wells were then imaged on a high throughput automated imaging analyzer. After imaging the wells, these wells were subjected to magnetic selection using a bar magnet apparatus. After a 5 min magnetic selection step, the same wells were reimaged.

Results. FIG. 11 shows that the presence of dye in the dye-cushion reagent completely shields any signal originating from outside of the detection zone. The results shown in FIG. 12 demonstrate that signaling moieties deposited in the detection zone by the magnetic selection of fluorescent particle-TSH-magnetic particle complexes can be detected in the presence of dye.

Conclusions. It can be seen that the combination of dye-cushion dramatically reduces the background from the un-reacted reagents and non-target complexes separated by density layer from the detection zone. This example demonstrates the contribution of dye-cushion reagent to the invention and allows the detection of targets by non-magnified imaging without washing. Individual fluorescent signaling particles can be discerned in the +target image and directly counted by the software.

Alternative embodiments. Alternative embodiments can also incorporate other density agents, including other commonly used density agents such as iodixanol, sodium diatrizoate, sodium, metrizaote, metrizamide, sucrose, and other sugars, oligosaccharides, synthetic polymers (e.g. Ficoll), and various salts such as cesium chloride, potassium bromide, and others.

Alternative embodiments can use other signaling moieties and other dyes selected to match the signaling character of the signaling moieties in use. For example the dye Toluidine Blue O could be used with the fluorescent label Texas Red (sulforhodamine).

Example 7

Visual Demonstration of the Suspension of Red Blood Cells by Dye Cushion Reagent This example visually demonstrates the ability of the cushion reagent to maintain a separation between the overlying reaction mixture, which may include solids like particles and cells, and the detection zone adjacent to the detection surface. The use of cushion for separation of the overlying reaction from the detection zone is demonstrated by its ability to prevent the red blood cells in a whole blood sample from settling to the bottom of a well containing cushion of an appropriate density.

Method. Aliquots of 20 µL of 10, 15, 20, 25, 30, 35, and 40% v/v solutions of Optiprep® (Sigma-Aldrich D1556) were pipetted into wells of a Nunc 384 well clear microtiter plate. Bovine whole blood (10 µL) was layered on top of the Optiprep® solutions and incubated for 15 minutes. After the incubation the wells were examined visually for any mixing and photographed using a digital camera.

Results. The image, shown in FIG. 13 demonstrates that Optiprep® concentrations greater than or equal to 25% v/v are able to keep the whole blood sample fully separated from the detection zone (bottom of the well) for at least 15 min.

Conclusions. It can be seen that the use of cushion maintains a separation between the overlying reagent mixture and the detection zone. In addition to avoiding the sedimentation of components from the sample into the detection zone, cushions in this density range exclude unbound label from the detection zone, as labeling particles are less dense than the red blood cells of this example. Exclusion of unbound label increases the sensitivity of detection of specifically selected label. The example is an embodiment of the invention demonstrating the function of the dye cushion reagent.

Alternative embodiments. Other agents can be used to produce the dense cushion of the example. When they are used to make a cushion of similar density, the separation of overlying reactants from the detection zone will be similar.

Example 8

Detection of Human Thyroid Stimulating Hormone in Human Whole Blood

This example describes the assay of Human Thyroid Stimulating Hormone (hTSH) in human whole blood by non-magnified imaging without any washing steps. The assay uses mouse monoclonal anti-hTSH coated fluorescent and magnetic particles to bind signaling moieties and selection moieties to TSH molecules contained in the human whole blood sample. The fluorescent particle-TSH-magnetic particle complexes are deposited into the detection zone using magnetic selection through a dye cushion. The reaction is carried out in a reaction well, and the reaction mixture is transferred to the top of the dyed cushion in an imaging well before magnetic selection is applied.

Method. In one experiment, the 20 µL reaction mixture included 10 µL 200 mM EPPS (Sigma-Aldrich Catalog No. E9502) buffer containing 400 mM 1,3 Diaminopropane (Sigma-Aldrich Catalog No. D230807) pH 7.8, 2 µL of fluorescent particles (0.02% w/v) coated with anti-hTSH antibody, 2 µL of magnetic particles (0.25% w/v) coated with anti-hTSH, 1 µL of uncoated Dynal Dynabeads® 'carrier' magnets (Dynabeads (7.2 mg/mL) were pre-incubated in a solution of 20 mM Tris-TBP for 15 min before use) and 5 µL whole blood sample with into which hTSH had previously been spiked. The reaction mixture was incubated for 10 min. (Note: 'carrier' magnets are intended to accelerate the magnetic selection step, but are not required to practice the invention). In a separate 384 well black well polystyrene plate, 10 µL of a dyed cushion reagent (30% w/v Optiprep® containing 2 mg/ml Chromotrope 2R) was added to specific wells. At the end of the incubation, a 5 µL aliquot of each reaction mixture was layered on top of the dye cushion layer and the plate was placed on a plate holder with parallel bar magnets. The plate and magnet apparatus was then placed in a high throughput automated imaging analyzer. The wells were then imaged on the analyzer described above at a 0.1 sec exposure time. Individual fluorescent particles were then enumerated using imaging software.

Results. The data in FIG. 14 shows examples of the non-magnified images of assay wells in the presence and absence of target. FIG. 15 shows the dose response curve data for the assay of TSH in whole blood generated by analyzing the images using automated software. These two results show the specific and sensitive detection of hTSH from a complex matrix like a whole blood sample using non-magnified imaging without any washing steps.

Conclusions. Example 8 demonstrates that the assay format using anti-TSH-conjugated fluorescent particles for signaling and anti-TSH-conjugated magnetic particles for selection, combined with the use of dyed-cushion and non-magnified imaging, allows one to detect TSH in a complex matrix like human whole blood without the need for washing steps.

Individual fluorescent signaling particles can be discerned in the +target image and directly counted by the software.

The specificity of the assay is enhanced by inclusion of a dye-cushion reagent. The dye absorbs at the excitation and/or emission wavelengths of the fluorescent moiety in use as label. This dye restricts the ability to image signaling target complexes to the detection zone. The addition of the dense cushion allows the separation of selectable complexes from non-selectable complexes further reducing background.

Alternate Embodiments. Other embodiments could make use of different signaling moieties, selection moieties, and dye and cushion constituents.

Other embodiments could use the same assay format to detect a variety of different targets including cells, viruses, organelles, lipoproteins, and molecules including proteins, oligonucleotides, lipids, oligosaccharides, and small organic and inorganic molecules.

The method is applicable to samples with complex matrices including whole blood, plasma, feces, wastewater, milk, and others.

Samples can also be processed prior to selection e.g. whole blood can be centrifuged to remove the cellular components, cells can be fixed with methanol, DNA can be extracted and purified, hormones, proteins and vitamins normally found bound to serum factors can be released, and through other processes.

While this assay involves the simultaneous contacting of anti-TSH fluorescent particles, anti-TSH magnetic particles, and TSH from the sample, the assay of the invention can be performed sequentially. For instance, targets can be pre-labeled with anti-TSH fluorescent particles before the addition of the anti-TSH magnetic particles.

Example 9

Detection of Human Thyroid Stimulating Hormone in Human Plasma

This example describes the assay of Human Thyroid Stimulating Hormone (hTSH) in human plasma by non-magnified imaging without any washing steps. The assay uses mouse monoclonal anti-hTSH coated fluorescent and magnetic particles to bind signaling moieties and selection moieties to TSH molecules contained in the human whole blood sample. The fluorescent particle-TSH-magnetic particle complexes are deposited into the detection zone using magnetic selection through a dye cushion. The reaction is carried out in a reaction well, and the reaction mixture is transferred to the top of the dyed cushion in an imaging well before magnetic selection is applied.

Method. In one experiment, the reaction mixture (20 μL) containing 10 μL 200 mM EPPS (Sigma-Aldrich Catalog No. E9502) buffer containing 400 mM 1,3 Diaminopropane (Sigma-Aldrich Catalog No. D230807) pH 7.8, 2 μL of fluorescent particles (0.02% w/v) coated with anti-hTSH antibody, 2 μL of magnetic particles (0.25% w/v) coated with anti-hTSH and 5 μL hTSH (spiked into human plasma previously depleted of hTSH using magnetic particles coated with anti-hTSH antibody manufactured in Example 5). The reaction was incubated for 10 min. In a separate 384 well black well polystyrene plate, 10 μL of a dyed cushion reagent (30% w/v Optiprep® containing 5 mg/ml Chromotrope 2R) was added to specific wells. At the end of the incubation, a 5 μL aliquot of each reaction mixture was layered on top of the dye cushion layer in a single well and the plate was placed on a plate holder with parallel bar magnets. The plate and magnet apparatus was then placed in a high throughput automated imaging analyzer. The wells were imaged on the analyzer described above at a 0.1 sec exposure time. Individual fluorescent particles were then enumerated using imaging software.

Results. The data in FIG. 16 shows an example of the non-magnified images of assay well in the presence and absence of target. FIG. 17 shows the dose response data generated by analyzing the images using automated software. These two results show the specific and sensitive detection of hTSH from a complex matrix like plasma using non-magnified imaging without any washing steps.

Conclusions. Example 9 demonstrates that the assay format using anti-TSH-conjugated fluorescent particles for signaling and anti-TSH-conjugated magnetic particles for selection, combined with the use of dyed-cushion and non-magnified imaging, allows one to detect TSH in a complex matrix like human plasma without the need for washing steps.

Individual fluorescent signaling particles can be discerned in the +target image and directly counted by the software.

The specificity of the assay is enhanced by inclusion of a dye-cushion reagent. The dye absorbs at the excitation and/or emission wavelengths of the fluorescent moiety in use as label. This dye restricts the ability to image signaling target complexes to the detection zone.

The addition of the dense cushion allows the separation of selectable complexes from non-selectable complexes further reducing background.

Alternate Embodiments. Other embodiments could make use of different signaling moieties, selection moieties, and dye and cushion constituents.

Other embodiments could use the same assay format to detect a variety of different targets including cells, viruses, organelles, lipoproteins, and molecules including proteins, oligonucleotides, lipids, oligosaccharides, and small organic and inorganic molecules.

The method is applicable to samples with complex matrices including whole blood, plasma, feces, wastewater, milk, and others.

Samples can also be processed prior to selection e.g. whole blood can be centrifuged to remove the cellular components, cells can be fixed with methanol, DNA can be extracted and purified. hormones, proteins and vitamins normally found bound to serum factors can be released, and through other processes.

While this assay involves the simultaneous contacting of anti-TSH fluorescent particles, anti-TSH magnetic particles, and TSH from the sample, the assay of the invention can be performed sequentially. For instance, targets can be pre-labeled with anti-TSH fluorescent particles before the addition of the anti-TSH magnetic particles.

Example 10

Detection of *Bacillus anthracis* (Anthrax) Lethal Factor in Human Plasma

This example describes the assay of a bacterial toxin, the lethal factor of *B. anthracis*, in human plasma. The assay uses mouse monoclonal anti-Anthrax lethal factor coated fluorescent and magnetic particles to bind signaling moieties and selection moieties to lethal factor molecules contained in the human plasma sample. The fluorescent particle-lethal factor-magnetic particle complexes are deposited into the detection zone using magnetic selection through a dye cushion. The reaction is carried out in a reaction well, and the reaction mixture is overlaid on the dyed cushion in an imaging well before magnetic selection is applied.

Method. The reaction mixture (50 μL) contained 10 μL 200 mM EPPS (Sigma-Aldrich Catalog No. E9502) buffer containing 400 mM 1,3 Diaminopropane (Sigma-Aldrich Catalog No. D230807) pH 7.8, 10 μL fluorescent particles (0.007% w/v) coated with anti-Anthrax lethal factor antibody as coating antibody), 10 μL of magnetic particles (0.05% w/v) coated with anti-Anthrax lethal f(IQ Corp., Catalog No. LF-IQ) (prepared as described in example 2 using anti-Anthrax lethal factor antibody actor antibody (prepared as described in example 4 with the following modifications: anti-Anthrax lethal factor monoclonal antibody as coating antibody), 10 μL of a buffer containing 1 mg/mL Alginic acid (Sigma-Aldrich Catalog No. A2158), 2.5% w/v Polyvinylpyrrolidone (Sigma-Aldrich Catalog No. PVP40), 0.5 mg/mL bovine gamma globulin (Lampire Laboratories Catalog No. 7400805), and 1 mg/mL mouse gamma globulin (Jackson Immunoresearch Catalog No. 015-000-002 in PBS, pH 7.4, and 10 μL of a human plasma sample spiked with recombinant Anthrax lethal factor (List Laboratories cat#172b). The reaction was incubated for 10 min. In a separate 96 well black polystyrene plate with a clear bottom, dye cushion reagent (15% Optiprep® containing 2 mg/ml Chromotrope 2R) was added to specific wells. At the end of the incubation, a 40 μL aliquot of each reaction mixture was layered on top of the dye cushion layer and the plate was placed on a bar magnets. The plate was then placed in a high throughput automated imaging analyzer. The wells were imaged on the analyzer described above using a 0.1 sec exposure time. Individual fluorescent particles were then enumerated using software.

Results. FIG. 18 shows examples of non-magnified images of assay wells in the presence and absence of target. FIG. 19 shows the dose response data generated by analyzing the images using automated software. These two results show the specific and sensitive detection of anthrax lethal factor from a complex matrix like plasma using non-magnified imaging without any washing steps.

Conclusions. Example 10 demonstrates that the assay format using anti-lethal factor-conjugated fluorescent particles for signaling and anti-lethal factor-conjugated magnetic particles for selection, combined with the use of dyed-cushion and non-magnified imaging, allows one to detect anthrax lethal factor in a complex matrix like human plasma without the need for washing steps.

At low concentrations of target, individual fluorescent signaling particles can be discerned in the +target image and directly counted by the software.

The specificity of the assay is enhanced by inclusion of a dye-cushion reagent. The dye absorbs at the excitation and/or emission wavelengths of the fluorescent moiety in use as label. This dye restricts the ability to image signaling target complexes to the detection zone. The addition of the dense cushion allows the separation of selectable complexes from non-selectable complexes further reducing background.

Alternate Embodiments. Other embodiments could make use of different signaling moieties, selection moieties, and dye and cushion constituents.

Other embodiments could use the same assay format to detect a variety of different targets including cells, viruses, organelles, lipoproteins, and molecules including proteins, oligonucleotides, lipids, oligosaccharides, and small organic and inorganic molecules.

The method is applicable to samples with complex matrices including whole blood, plasma, feces, wastewater, milk, and others.

Samples can also be processed prior to selection e.g. whole blood can be centrifuged to remove the cellular components, cells can be fixed with methanol, DNA can be extracted and purified. hormones, proteins and vitamins normally found bound to serum factors can be released, and through other processes.

While this assay involves the simultaneous contacting of anti-target fluorescent particles, anti-target magnetic particles, and target from the sample, the assay of the invention can be performed sequentially. For instance, targets can be pre-labeled with anti-target fluorescent particles before the addition of the anti-target magnetic particles.

Example 11

Detection of *Bacillus anthracis* (Anthrax) Protective Antigen in Human Plasma

This example describes the assay of a bacterial toxin component, the Anthrax protective antigen of *B. anthracis*, in human plasma. The assay uses mouse monoclonal anti-Anthrax protective antigen coated fluorescent and magnetic particles to bind signaling moieties and selection moieties to protective antigen molecules contained in the human plasma sample. The fluorescent particle-protective antigen-magnetic particle complexes are deposited into the detection zone using magnetic selection through a dye cushion. The reaction is carried out in a reaction well, and the reaction mixture is overlaid on the dyed cushion in an imaging well before magnetic selection is applied.

Method. Reaction Mixture (50 μL) contained 20 μL PBS-TBP+400 mM 1,3 Diaminopropane (Sigma-Aldrich Catalog No. D230807) pH 7.8, 10 μL fluorescent particles (0.007% w/v) coated with anti-Anthrax protective antigen antibody [C3, Meridian Biodesign, catalog No. C86613M) (prepared as described in example 2 using anti-Anthrax protective antigen antibody as coating antibody), 10 μL of magnetic particles (0.05% w/v) coated with anti-Anthrax protective antibody [BAP-0105 Meridian Biodesign, Catalog No. C86501M) (prepared as described in example 4 with the following modifications: anti-Anthrax protective antigen as coating antibody) and 10 μL of human plasma sample spiked with recombinant Anthrax protective antigen (List Laboratories, Catalog No. 171A). The reaction was incubated for 10 min. In a separate 96 well black well clear bottom polystyrene plate, 90 μL of dyed cushion reagent (15% Optiprep® containing 2 mg/ml Chromotrope 2R) was added to specific wells. At the end of the incubation, a 40 μL aliquot of reaction mixture was layered on top of the dye cushion layer and the plate was placed on a bar magnets built. The plate was then placed in a high throughput automated imaging analyzer. The wells were imaged on the analyzer described above using a 0.1 sec exposure time. Individual fluorescent particles were then enumerated using software.

Results. FIG. 20 shows examples of non-magnified images of assay wells in the presence and absence of target. FIG. 21 shows the dose response data generated by analyzing the images using automated software. These two results show the specific and sensitive detection of anthrax protective antigen from a complex matrix like plasma using non-magnified imaging without any washing steps.

Conclusions. Example 11 demonstrates that the assay format using anti-Anthrax protective antigen-conjugated fluorescent particles for signaling and anti-Anthrax protective antigen-conjugated magnetic particles for selection, combined with the use of dyed-cushion and non-magnified imaging, allows one to detect anthrax protective antigen in a complex matrix like human plasma without the need for washing steps.

The specificity of the assay is enhanced by inclusion of a dye-cushion reagent. The dye absorbs at the excitation and/or emission wavelengths of the fluorescent moiety in use as label. This dye restricts the ability to image signaling target complexes to the detection zone. The addition of the dense cushion allows the separation of selectable complexes from non-selectable complexes further reducing background.

Alternate Embodiments. Other embodiments could make use of different signaling moieties, selection moieties, and dye and cushion constituents.

Other embodiments could use the same assay format to detect a variety of different targets including cells, viruses, organelles, lipoproteins, and molecules including proteins, oligonucleotides, lipids, oligosaccharides, and small organic and inorganic molecules.

The method is applicable to samples with complex matrices including whole blood, plasma, feces, wastewater, milk, and others.

Samples can also be processed prior to selection e.g. whole blood can be centrifuged to remove the cellular components, cells can be fixed with methanol, DNA can be extracted and purified. hormones, proteins and vitamins normally found bound to serum factors can be released, and through other processes.

While this assay involves the simultaneous contacting of anti-target fluorescent particles, anti-target magnetic particles, and target from the sample, the assay of the invention can be performed sequentially. For instance, targets can be pre-labeled with anti-target fluorescent particles before the addition of the anti-target magnetic particles.

Example 12

Detection of Bacterial *Bacillus anthracis* poly-D-γ-glutamic Acid Capsule Polypeptide (PDGA) in Human Urine This example describes the assay of a bacterial capsular polypeptide, the poly-D-γ-glutamic acid of *B. anthracis*, in human urine. The assay uses mouse monoclonal anti-PDGA-coated fluorescent and magnetic particles to bind signaling moieties and selection moieties to PDGA contained in the human plasma sample. The fluorescent particle-PDGA-magnetic particle complexes are deposited into the detection zone using magnetic selection through a dye cushion. The reaction is carried out in a reaction well, and the reaction mixture is overlaid on the dyed cushion in an imaging well before magnetic selection is applied.

Method. The 50 μL reaction mixture was composed of 20 μL PBS-TBP, 10 μL fluorescent particles (0.007% w/v) coated with anti-Anthrax PDGA antibody (prepared as described in example 2 using anti-Anthrax PDGA antibody as coating antibody), 10 μL of magnetic particles (0.025% w/v) coated with anti-Anthrax PDGA antibody (prepared as described in example 4 with the following modifications: anti-Anthrax PDGA as coating antibody) and 10 μL of human urine sample spiked with poly-D-γ-glutamic acid (synthetic 50-mer, AnaSpec). The reaction was incubated for 5 min. In a separate 96 well black well clear bottom polystyrene plate, dye cushion reagent (15% Optiprep® containing 2 mg/ml Chromotrope 2R) was added to specific wells. At the end of the incubation, 40 μL aliquot of reaction mixture was layered on top of the dye cushion layer and the plate was placed on a pin magnet array for 7 minutes. The plate was imaged in a high throughput automated imaging analyzer using a 0.1 sec exposure time. Individual fluorescent particles were then enumerated using software.

Results. FIG. 22 shows examples of non-magnified images of assay wells in the presence and absence of target. FIG. 23 shows the dose response data generated by analyzing the images using automated software. These two results show the specific and sensitive detection of PDGA in human urine, demonstrating the diversity of matrices which can be used as samples in the invention.

Conclusions. Example 12 demonstrates that the assay format using anti-PDGA-conjugated fluorescent particles for signaling and anti-PDGA-conjugated magnetic particles for selection, combined with the use of dyed-cushion and non-magnified imaging, allows one to detect anthrax protective antigen in urine without the need for washing steps.

Alternate Embodiments. Because PDGA is a repeating polymer with multiple binding sites for any single monoclonal antibody, alternative embodiments can make use of a single antibody conjugated to both the fluorescent and the magnetic particles.

Other embodiments could make use of different signaling moieties, selection moieties, and dye and cushion constituents.

Other embodiments could use the same assay format to detect a variety of different targets including cells, viruses, organelles, lipoproteins, and molecules including proteins, oligonucleotides, lipids, oligosaccharides, and small organic and inorganic molecules.

The method is applicable to samples with complex matrices including whole blood, plasma, feces, wastewater, milk, and others.

Samples can also be processed prior to selection e.g. whole blood can be centrifuged to remove the cellular components, cells can be fixed with methanol, DNA can be extracted and purified, hormones, proteins and vitamins normally found bound to serum factors can be released, and through other processes.

While this assay involves the simultaneous contacting of anti-target fluorescent particles, anti-target magnetic particles, and target from the sample, the assay of the invention can be performed sequentially. For instance, targets can be pre-labeled with anti-target fluorescent particles before the addition of the anti-target magnetic particles.

Example 13

Detection of *Bacillus anthracis* (Anthrax) Lethal Factor in Human Whole Blood by Automated Analysis This example describes the use of a fully automated high-throughput surge testing instrument for assaying a bacterial toxin, the lethal factor of *B. anthracis*, in human whole blood. The assay uses mouse monoclonal anti-Anthrax lethal factor-coated fluorescent and magnetic particles to bind signaling moieties and selection moieties to lethal factor molecules contained in the human plasma sample. The fluorescent particle-lethal factor-magnetic particle complexes are deposited into the detection zone using magnetic selection through a dye cushion. A sample carrier containing whole blood samples spiked with different concentrations of lethal factor was presented to the instrument. The instrument assembled and incubated the reactions in reaction wells, and then overlaid each reaction on dyed cushion in an imaging well, transported the wells to a magnetic selection station, and imaged the wells automatically.

Method. The assay composition was identical to that described in example 10. All reagents were loaded into the reagent cups of a high throughput surge testing instrument. All pipetting steps described below were carried out by fully automated robotic pipettors under computer control. First, 10 µL of 200 mM EPPS (Sigma-Aldrich Catalog No. E9502) buffer containing 400 mM 1,3 Diaminopropane (Sigma-Aldrich Catalog No. D230807) pH 7.8 was added to the reaction cup followed by pipetting of 10 µL of a reagent containing 1 mg/mL Alginic acid (Sigma-Aldrich Catalog No. A2158), 2.5% w/v Polyvinylpyrrolidone (Sigma-Aldrich Catalog No. PVP40), 0.5 mg/mL bovine gamma globulin (Lampire Laboratories Catalog No. 7400805) and 1 mg/mL mouse gamma globulin (Jackson Immunoresearch Catalog No. 015-000-002) in PBS). Ten µL of human whole blood spiked with Anthrax lethal factor ((List Laboratories, Catalog No. 172b) was added. Subsequently, 10 μL of a 0.007% w/v dilution of anti-Anthrax lethal factor fluorescent particles (prepared as described in example 10) and 10 μL of a 0.05% w/v dilution of anti-Anthrax lethal factor magnetic particles (prepared as described in example 10) were added, mixed by an onboard mixer, and incubated for 6 min. During the incubation 90 μL of dyed cushion reagent (30% Optiprep® containing 10 mg/ml Chromotrope 2R) was added to separate imaging cups automatically. After incubation, 40 μL of reaction mixture was layered on top of the dye-cushion layer in imaging wells of the analyzer. The imaging cups were then automatically moved over magnets within the analyzer and magnetic separation was carried out for 1 min. After the deposition of magnetic particles into the detection zone, the imaging cups were automatically moved to imaging stage and were then imaged on the analyzer using a 0.1 sec exposure time. Individual fluorescent particles were then enumerated and the sample results analyzed in an automated manner using software on the analyzer.

Results. The data generated using a fully automated surge-testing instrument is presented in FIG. 24. The graph shows the dose response curve generated by automated analysis of the acquired images using software. These results demonstrate fully automated, specific and sensitive, detection of *B. anthracis* lethal factor from a complex matrix like human blood using non-magnified imaging without any washing steps.

Conclusions. Example 13 demonstrates that assays of the invention can be fully automated in a high-throughput system.

Example 14

Assay of *Bacillus anthracis* (Anthrax) Capsule Peptide-poly-γ-D-glutamic Acid (PDGA)-Competitive Format Example 15 describes the assay of Anthrax poly-γ-D-glutamic acid (PDGA) using a competitive assay format using magnified imaging without requiring a washing step. Small molecules (haptens) generally can be bound only by a single specific binding moiety. This does not permit their simultaneous binding by category binding moieties linked to signaling and selection moieties. Such targets can still be analyzed by the method of the invention through use of a 'competitive' format. Many different versions of 'competitive' binding assays are well-know in the art.

The 'competitive' format used in this example uses a plurality of targets that are conjugated to selection moieties to form target competitors. In the absence of target in the sample, fluorescent particles conjugated to target-specific category binding moieties bind to the target competitors and are selected and detected in the assay. When target is present, it competes with the target-competitor for binding to the fluorescent particles thereby reducing the quantity of signal detected in the assay. This reduction is proportional to amount of target present.

Methods. The preparation of anti-PDGA antibody coated fluorescent particles is described in Example 13. Streptavidin coated magnetic particles were manufactured as described in example 4 with the following modification where streptavidin (Prozyme SA10) was conjugated to magnetic particles instead of antibody. Biotinylated synthetic PDGA 9-mer peptide (manufactured by Anaspec) was added in excess to streptavidin-coated magnetic particles and incubated for 1 hr. The PDGA magnetic particles were then washed extensively in PBS-TBP, pH 7.4. 2 μL of anti-PDGA antibody coated fluorescent particles were mixed with 25 μL of a sample containing various concentrations of a $PDGA_9$-thyroglobulin conjugate, followed by 2 μL of PDGA-magnetic particles. The reaction was incubated for 5 minutes with shaking. The reaction was diluted and placed on a magnet to separate bound from unbound fluorescent particles. The supernatant was removed and the captured fluorescence was detected by reading in a Victor 2 fluorometer. A large number of antibody-coated fluorescent particles were captured by antigen-coated magnetic particles. The degree of signal inhibition (competition) corresponded to the amount of bacterial capsule peptide in the sample.

Results. The result shown in FIG. 25 indicates that the competitive immunoassay format with magnetic capture could be used to detect presence or absence of targets (PDGA from *B. anthracis*). The data demonstrate an inhibition assay curve characteristic of binding assays using a 'competitive' format.

Conclusions. Example 14 shows the alternative assay format (competitive) could be utilized with some embodiments of the invention for detecting targets from various samples, and could easily be incorporated into an assay of the invention.

Alternative embodiments. The anti-PDGA fluorescent particles and PDGA-competitor-coupled magnetic particles are mixed as described above with samples containing varying quantities of $PDGA_9$ peptide. After the contacting step, the reaction mixture is layered over a dyed cushion, subjected to magnetic selection and imaged in the high throughput automated imaging analyzer using a 0.1 sec exposure time. In the absence of $PDGA_9$ in the sample, a high number of particles are captured in the detection zone. As the quantity of PDGA in the sample increases, the number of captured particles decreases.

There are numerous 'Competitive' binding assay formats well-known in the art that can be applied to the invention. In another competitive assay embodiment both the signaling moiety and the selection moiety are conjugated to target competitors. The crosslinking of signaling moiety and capture moiety is effected by an at least bivalent category-specific molecule (e.g. an antibody) supplied in the reaction. The crosslinking reaction is inhibited by the binding of added target to the bivalent category-specific binding moiety resulting in a reduction in the quantity of signal when target is present in the reaction. In a third competitive embodiment the signaling and selection moieties are each conjugated to category-specific binding moieties which can bind to the target. The addition of an at least bivalent target competitor conjugate induces the formation of selectable signal-selection moiety complexes. Again, the formation of crosslinked complexes between signaling moiety and selection moiety is reduced by the addition of target.

Other embodiments could make use of different signaling moieties, selection moieties, and dye and cushion constituents in any of these competitive assay formats.

Example 15

Use of Positive and Negative Internal Controls to Ensure the Assay Accuracy

This example describes the incorporation of parallel internal positive and negative internal controls run in the test sample into certain embodiments of the invention to test for matrix effects on the test results. The incorporation of internal controls run in the test matrix ensures the accuracy of the test result, reducing false results and the need for retesting.

A positive control (for instance, adding a predetermined quantity of target to the test sample) would be expected to add a definable incremental signal when the control is added to the test sample. If the positive control is not detected, the sample can be considered to have a negative interference and interpreted appropriately. Similarly, a negative control, designed to inhibit the production of signal due to target in the sample (for instance, by adding a large quantity of the category-specific binding moiety used to bind label to the target), should result in a reduction of the signal produced by a positive sample. A positive sample which does not demonstrate a decreased signal in the negative control well is either a false positive or an extremely high true positive. These alternatives can be distinguished by dilution of the sample.

Method. This experiment utilized anti-target antibody coated fluorescent and magnetic particles for detecting various corresponding targets hTSH, Anthrax protective antigen (PA) and Anthrax capsule poly-D-γ-glutamic acid (PDGA) as described in examples 5, 11 and 12. Separate reaction mixes of samples with and without target (100 pg/mL each) were added to each of three wells with the reaction mix for each assay with the following additions: for sample quantification, PBS-TBP, pH 7.4, for the positive internal control 100 pg/mL target in PBS-TBP and for the negative internal control a large excess (1 µg/mL) of free target specific antibody (same antibody on the antibody coated fluorescent particles) in PBS-TBP (see examples 5, 11 and 12 for details). Samples were incubated for 10 minutes. In a separate 96 well black well clear bottom polystyrene plate, dye cushion reagent (90 µL) was added to specific wells. At the end of the incubation, 40 µL aliquot of reaction mixture was layered on top of the dye cushion layer and the plate was placed on a bar magnet array to perform the selection step. The plate was placed in a high throughput automated imaging analyzer where the wells were imaged using a 0.1 sec exposure time. Individual fluorescent particles were then enumerated using software.

Results. The FIG. 26 shows the images for each assay (hTSH, Anthrax PA, and Anthrax PDGA) for the experimental, positive, and negative internal controls run in test samples with and without targets. It could be seen from the Figure that this methodology allows correction of the assay results for false-negative and false positive reactions.

Conclusion. This experiment demonstrates the one of the embodiment presented in this invention regarding controls i.e. the internal controls work with the invention and could be used to ensure the accuracy of results. The results show the expected signal and no signal (+ and −) in the wells with and without target. The positive internal control wells show positive signals in all wells as predicted, and the negative internal controls show no signal as predicted.

Alternative embodiments. In some embodiments of the invention the use of either the negative or the positive internal control could be used alone. Alternative negative controls include the use of a signaling moiety conjugated to an irrelevant category-binding molecule.

In other embodiments of the invention negative and positive internal controls could be used to verify the performance of unitized reagents including those within cartridges or dried in wells.

Positive and negative internal controls could be used in specific embodiments such as the detection of drug resistant bacterial or cancer cells in a sample. In these embodiments the controls could be used to confirm that a growth step occurred properly and to distinguish drug resistant from drug sensitive cell populations.

Example 16

Specific Detection of *Staphylococcus aureus* Cells by Non-Specific SYBR® Green I Staining and Using Magnetic Nanoparticles that Bind Specifically to the Cell Surface Antigen Protein A This example describes a method for staining *S. aureus* bacterial cells with non-specific stain followed by using target-specific magnetic particles to detect specific targets. Use of target-specific magnetic particles combined with non-specific staining has general use in the context of the invention because the staining and capture of target allow easy target enumeration using non-magnified imaging.

This example demonstrates using non-magnified imaging that *S. aureus* are readily labeled with SYBR® Green 1 dye and specifically captured using the target-specific magnetic particles.

The method can thus be used to detect and enumerate individual cellular and molecular targets at low concentrations in clinical, industrial, and environmental samples.

Method. The schematics of the *S. aureus* assay using SYBR® Green 1 and anti-protein A antibody coated magnetic particles is shown in FIG. 27. *S. aureus* cells were labeled with SYBR® Green 1 and anti-protein A antibody coated magnetic particles manufactured as described in Example 4. A culture of *S. aureus* (ATCC strain 29213) was grown in growth media TSB (Tryptic Soy Broth, Acumedia Catalog No. 7164A) at 35° C. for 2 hours to achieve log-phase growth ($OD_{600}$=0.3). The *S. aureus* cells were counted using Petroff-Hausser counting chamber on Zeiss microscope and cells were diluted to $2 \times 10^5$ cells/mL in fresh TSB. The reaction was carried out in 96 well polycarbonate PCR plate (Fisher Scientific, Cat. No. 14230237). The reaction mixture (50 µL) contained 25 µL *S. aureus* cells (5,000 cells), 20 µL of SYBR® Green 1 dye (diluted 1:2000× in saline) and 5 µL of anti-protein A coated magnetic particles ($2 \times 10^{10}$ particles/mL) suspended into PBS-TBP solution (10 mM Phosphate, 140 mM NaCl, 3 mM KCl (Calbiochem Catalog No. 524650), 0.05% w/v Tween 20 (Acros Catalog No. 2333600010), 2 mg/mL BSA (Sigma-Aldrich), 0.05% w/v ProClin 300 (Supelco) adjusted to pH 7.4). Assay reaction was mixed well by pipetting and incubated for 15 min at ambient temperature in dark. After incubation, 40 µL of reaction mixture was overlaid on 70 µL of dyed cushion solution (15% OptiPrep® (Sigma Cat. No. D1556) containing 5 mg/mL Chromotrope 2R (Sigma-Aldrich C3143)) pre-aliquoted in 96-well half-area diameter clear bottom black plate (Grainer, Cat. No. 675096). In order to select cell-particles complexes at the bottom of the well, the plate was then subjected to magnetics by placing it on magnet for 4 min. The plate was then removed from the magnet and was placed in a high throughput automated imaging analyzer. The wells were then imaged on the analyzer described above at a 0.1 sec exposure time. Individual Fluorescent cells were then enumerated using software.

Results. FIG. 28 shows the images of assay results of labeling of S. aureus cells by SYBR® Green 1 and specific capture using antibody coated magnetic particles. Panel A shows the image of a well containing reaction without S. aureus cells (negative control). Panel B shows the image of the well of the reaction containing 5000 S. aureus cells and panel C shows the image of the well of the reaction containing 50,000 S. epidermidis cells (as a specificity control). It is clear from the data that high numbers of fluorescent objects were only observed when the reaction mixture contained S. aureus cells (panel B). The wells containing the no cell control and S. epidermidis did not give any signal above the background (panels A and C). FIG. 29 demonstrates the method described here is capable of detecting and enumerating individual cellular targets at low concentrations.

Conclusions. In the context of this invention, this data demonstrate the antibody-coated magnetic particles could be used to specifically capture the labeled the cells (e.g. S. aureus). Moreover, assay is highly specific as non S. aureus bacteria (e.g. S. epidermidis) does not produce signal over the background indicating the assay specificity. As shown in subsequent examples, the capture and labeling method used here can be combined in the context of the invention with methods for discriminating capture target from free signaling moieties and other labeled entities.

At low concentrations of target cells, individual fluorescent cells can be discerned in the +target images and directly counted by the software.

Alternative embodiments. Other nucleic acid stains could be used to label the cells for detection, or other types of fluorescent cell staining could be employed. A target-specific label could be employed to allow cell detection; for instance, fluorescent particles conjugated to anti-protein A antibodies or Alexa®490-labeled anti-Protein A antibodies could be used as a label. Additionally, other selection modes could be employed for this assay, including selection using dense particles.

Example 17

Specific Detection of S. Aureus Cells by Using Antibody-Coated Fluorescent Particles and Magnetic Nanoparticles that Bind Specifically to the Cell Surface Antigen Protein A This example describes a method for specific labeling of S. aureus bacterial cells using anti-protein A antibody coated fluorescent particles (example 2) and specific capture using magnetic particles (example 4) to detect specific targets. Use of target-specific fluorescent and magnetic particles combined with use of dye-cushion has general use in the context of the invention because the staining and capture of target allow easy target enumeration using non-magnified imaging without any washing steps.

The method can thus be used to detect and enumerate individual cellular and molecular targets at low concentrations in clinical, industrial, and environmental samples.

Method. The schematics of the S. aureus assay using anti-protein A antibody coated fluorescent particles and anti-protein A antibody coated magnetic particles is shown in FIG. 30. A culture of S. aureus (ATCC strain 29213) was grown in growth media TSB (Tryptic Soy Broth, Acumedia Catalog No. 7164A) at 35° C. for 2 hours to achieve log-phase growth ($OD_{600}$=0.3). The S. aureus cells were counted using Petroff-Hausser counting chamber on Zeiss microscope and cells were diluted to $1 \times 10^6$ cells/mL in fresh TSB. The reaction was carried out in 96 well polycarbonate PCR plate (Fisher Scientific, Cat. No. 14230237). The reaction mixture (50 µL) contained 20 µL of PBS-TBP, 10 µL of S. aureus cells (10,000 cells), 10 µL of anti-protein A antibody coated fluorescent particles ($1.25 \times 10^{10}$ particles/mL) and 10 µL of anti-protein A antibody coated magnetic particles ($6.25 \times 10^9$ particles/mL). Assay reaction was mixed well by pipetting and incubated for 30 min at ambient temperature. After incubation, 20 µL of reaction mixture was overlaid on 70 µL of dyed-cushion solution (15% OptiPrep® (Sigma Cat. No. D1556) containing 5 mg/mL Chromotrope 2R (Sigma-Aldrich C3143)) pre-aliquoted in 96-well half-area diameter clear bottom black plate (Grainer, Cat. No. 675096). In order to select cell-particles complexes at the bottom of the well, the plate was then subjected to magnetics by placing it on magnet. The plate was then removed from the magnet and was placed in a high throughput automated imaging analyzer. The wells were then imaged on the analyzer described above at a 0.1 sec exposure time. Individual fluorescent cells were then enumerated using software. As a specificity control, we have used S. epidermidis (ATTC strain 12228), which was also assayed in a similar fashion as described above.

Results. FIG. 31 non-magnified images of assay results which employs specific labeling and capture of S. aureus cells by antibody coated fluorescent particles as signaling moiety and antibody coated magnetic particles as selection moiety, respectively. Panel A shows the image of well containing reaction without S. aureus cells (negative control). Panel B shows the image of the well of the reaction containing 4000 S. aureus cells and panel C shows the image of the well of the reaction containing 40,000 S. epidermidis cells (as specificity control). It is clear from the data that high numbers of individual fluorescent objects were seen in the image only observed when the reaction mixture contained S. aureus cells (panel B). The no cell well as well as well containing S. epidermidis did not give any signal above the background (Panels A and C). FIG. 32 demonstrates the method described here is capable of detecting and enumerating individual cellular targets at low concentrations.

Conclusions. In context of the invention, this data demonstrate the use of signaling moiety (antibody-coated fluorescent particles) and selection moiety (magnetic particles) in a homogenous assay (no wash steps) for specific labeling and selection of S. aureus cells and enumerating cells at low target concentration. Moreover, assay is highly specific as non S. aureus bacteria (e.g. S. epidermidis) does not produce signal over the background indicating the assay specificity. As shown in subsequent examples, the capture and labeling method used here can be combined in the context of the invention with methods for discriminating capture target from free signaling moieties and other labeled entities.

At low concentrations of target cells, individual fluorescent cells can be discerned in the +target images and directly counted by the software.

Alternative embodiments. In other embodiments, nucleic acid stains could be used to label the cells for detection, or other types of nonspecific fluorescent cell staining could be employed. A target-specific label could be employed to allow cell detection; for instance, Alexa®490-labeled anti-Protein A antibodies could be used as a label. Additionally, other selection modes could be employed for this assay, including selection using dense particles.

Example 18

Specific Detection Methicillin Resistant S. aureus (MRSA) Through Selective Growth Followed by Non-Specific SYBR® Green I Staining and Using Magnetic Nanoparticles that Bind Specifically to the Cell Surface Antigen Protein A In this example, we describe an assay for drug resistant bacteria based on phenotypic selection during growth for the rapid detection of methicillin resistant S. aureus (MRSA). This example describes a method for staining S. aureus bacterial cells with non-specific stain followed by using target-specific magnetic particles to detect specific targets. Combining selective growth followed by the use of target-specific magnetic particles and non-specific staining has general use in the context of the invention because the differential growth followed by staining and capture of target allow easy target enumeration using non-magnified imaging and would detect differential characteristic of bacteria (such as drug resistance).

This example demonstrates using differential growth and non-magnified imaging that drug resistant bacteria are readily detected using SYBR® Green 1 dye staining and specific capture using the target-specific magnetic particles.

The method can thus be used to detect and enumerate individual cellular and molecular targets at low concentrations in clinical, industrial, and environmental samples.

This example demonstrates using non-magnified imaging that S. aureus are readily labeled with SYBR® Green 1 dye and specifically captured using the target-specific magnetic particles.

Method. The schematics of rapid detection of methicillin resistant S. aureus (MRSA) using selective growth followed by non-magnified imaging is shown in FIG. 33. MRSA can be detected by counting the number of cells that result from incubating aliquots of a sample under 3 different growth conditions (no growth, growth without antibiotics and growth in presence of antibiotics). Three possible types of cells can be present, non-S. aureus, methicillin-sensitive S. aureus (MSSA), and methicillin-resistant S. aureus (MRSA). The cells in the given sample are inoculated into the above 3 media and incubated for several doubling times for the reliable detection of MRSA cells followed by specific detection of S. aureus.

Selective growth. For this experiment, we have used methicillin sensitive S. aureus (MSSA: ATCC strain 29213), methicillin-resistant S. aureus (MRSA: ATCC strain 43300) and S. epidermidis (S. epidermidis ATTC strain 12228). These cells were grown in growth media TSB (Tryptic Soy Broth, Acumedia Catalog No. 7164A) without any antibiotics at 35° C. for 2-3 hours to achieve log-phase growth ($OD_{600}$=0.3). The S. aureus/S. epidermidis cells were counted using Petroff-Hausser counting chamber on Zeiss microscope and cells were diluted to $1 \times 10^4$ cells/mL in fresh TSB. Each cells (100 µL) were inoculated into 100 µL of fresh TSB media containing 0.1% w/v ProClin 300 (Supelco), just TSB and TSB containing 6 µg/mL cefoxitin (Sigma, Catalog No. C4786), respectively. The growth was carried out in 24-well microtiter plate (Corning Catalog No. 25820) at 35° C. for 4 hours. After the growth, these samples were assayed as follows.

Assay. The assay reaction was carried out in 96 well polycarbonate PCR plate (Fisher Scientific, Cat. No. 14230237). The reaction mixture (50 µL) contained 25 µL culture media from each growth sample, 20 µL of SYBR® Green 1 dye (diluted 1:2000× in 0.9% sodium chloride solution) and 5 µL of anti-protein A coated magnetic particles ($2 \times 10^{10}$ particles/mL) suspended into PBS-TBP, pH 7.4. Assay reaction was mixed well by pipetting and incubated for 15 min at ambient temperature in dark. After incubation, 40 µL of reaction mixture was overlaid on 70 µL of dyed cushion solution (15% OptiPrep® (Sigma Cat. No. D1556) containing 5 mg/mL Chromotrope 2R (Sigma-Aldrich C3143)) pre-aliquoted in 96-well half-area diameter clear bottom black plate (Grainer, Cat. No. 675096). In order to select cell-particles complexes at the bottom of the well, the plate was then subjected to magnetics by placing it on magnet for 4 min. The plate was then removed from the magnet and was placed in a high throughput automated imaging analyzer. The wells were then imaged on the analyzer described above at a 0.1 sec exposure time. Individual Fluorescent cells were then enumerated using software.

Results. FIG. 34 shows the assay results of MRSA assay using SYBR® Green 1 and specific capture using antibody coated magnetic particles. Top Panel (MSSA) shows the images of wells containing methicillin sensitive S. aureus (MSSA), middle panel (MSSA) shows the images of wells containing methicillin resistant S. aureus (MRSA) and the bottom panel shows the images of wells containing S. epidermidis (negative control). It is clear from the data that MSSA shows growth in only one well (growth without antibiotics) while MRSA shows the growth in absence and presence of antibiotics (6 µg/mL cefoxitin). On the contrary, no bacteria is detected when S. epidermidis was used indicating the specificity of the MSRA assay.

Conclusions. This data demonstrate that selective growth combined with labeling and specific capture of the bacterial cells using antibody-coated magnetic particles could be used to distinguish antibiotics sensitive cells from antibiotics resistant cells. As shown in previous examples, the capture and labeling method used here can be combined in the context of the invention with methods for discriminating capture target from free signaling moieties and other labeled entities.

At low concentrations of target cells, individual fluorescent cells can be discerned in the +target images and directly counted by the software.

Example 19

Stabilization of Individual Reagents by Lyophilization of Thyroid Stimulating Hormone (hTSH) Reagents This example describes the stabilization of individual reagents for the detection of human Thyroid stimulating hormone (hTSH) by lyophilization. The methods described in this example are generally applicable to the reagents used in other embodiments of the invention.

Stabilization of assay reagents extends the shelf-life and performance of the assay reagents described in this invention.

Long-term storage of dried reagents is of economic value to the users of the reagents and is especially importance when applied to situations in which reagents are not regularly needed but for which a sudden need arises such as a bioterrorist incident or epidemic disease outbreaks.

Lyophilized reagents are also of use in the manufacture of unitized reagents such as single-use cartridges.

The method described can be used with reagents manufactured to detect and enumerate individual cellular and molecular targets at low concentrations in clinical, industrial, and environmental samples.

Method. In one experiment, individual lyophilization of hTSH assay components (fluorescent/magnetic particles and dyed-cushion) was carried out follows. A Dura-Stop lyophilizer was pre-cooled to −45° C. Dye-cushion reagent 10 µL (made as described in example 7 with the following modifications: 5% w/v trehalose (Sigma-Aldrich cat# T9449) was included to the reagent) was lyophilized on the bottoms of specific wells of a black-walled 384-well microtiter plate (Costar, Catalog No. 3544). After the addition, the plate was frozen in a Dura-Stop lyophilizer at atmospheric pressure at −45° C. for 1 hr and the vacuum was applied. The plate was lyophilized for 16 hours; the lyophilizer was brought to −5° C. for 4 hrs and then 25° C. for 1 hour. The pressure was released and the plate was removed, sealed with PCR plate film, and stored at room temperature in a desiccator until further use. The lyophilization of hTSH particle reagents was carried out as follows. Lyophilized spheres of 5 µL of a mixture of 160 mM EPPS (Sigma-Aldrich cat# E9502) buffer pH 7.6 containing 320 mM 1,3 Diaminopropane (Sigma-Aldrich cat# D230807), 5% w/v trehalose (Sigma-Aldrich cat# T9449), 0.003% w/v dilution of anti-hTSH antibody coated fluorescent particles and 0.08% w/v dilution of anti-hTSH antibody coated magnetic particles (particle reagents were prepared as described in example 6) were manufactured by accurately pumping 5 µL drops of the mixture into a insulated beaker containing liquid nitrogen. The frozen spheres were then immediately placed in Dura-Stop lyophilizer pre-cooled to −45° C. The vacuum was applied immediately and the spheres were lyophilized for 16 hrs, the lyophilizer was brought to −5° C. for 4 hrs and then 25° C. for 1 hour and stored at room temperature in a desiccator until further use.

The performance of lyophilized reagents was determined by comparing the hTSH assay performed using fresh liquid reagent and lyophilized reagent. Two different target (hTSH) solutions (62.5 and 250 pg/mL) were made by adding recombinant hTSH (Cell Sciences, Catalog No. CRT505B) to PBS-TBP. Lyophilized spheres of fluorescent and magnetic anti-hTSH antibody coated particles (as manufactured above) were placed on top of specific wells containing lyophilized dye-cushion reagent (FIG. 35 shows the assay schematics). In a separate 384 well black wall clear bottom microtiter plate (Costar), 10 µL of dye cushion reagent (as described in example 7 with the following modifications: 5% w/v trehalose (Sigma-Aldrich catalog no. T9449) was included) was pipetted into specific wells. After incubation, 5 µL aliquot of the 250 pg/mL solution of TSH was added to 5 µL of a mixture of 160 mM EPPS (Sigma-Aldrich, Catalog No. E9502) buffer containing 320 mM 1,3 Diaminopropane (Sigma-Aldrich Catalog No. D230807), 5% w/v trehalose (Sigma-Aldrich, Catalog No. T9449), 0.003% w/v dilution of anti-hTSH fluorescent particles and 0.08% w/v dilution of anti-hTSH magnetic particles and incubated for 10 min in specific wells of a 96 well polycarbonate PCR plate (Fisher Scientific, Cat. No. 14230237). After incubation, 7.5 µL of this mixture was layered onto of the liquid dye-cushion wells. During the incubation of the liquid reagents, 20 µL of the 62.5 pg/mL solution of hTSH was carefully pipetted on top of specific wells of lyophilized reagents. The plates were then subjected to magnetics by placing the plate on a bar magnet for 5 minutes. The plates were then placed in a high throughput analysis automated analyzer. The wells were then imaged on the analyzer at a 0.1 sec exposure time Results. FIG. 36 (top) shows a bar graph indicating the percent recovery of hTSH in the lyophilized reagent wells compared to the liquid reagent wells (Liquid reagents were assigned as 100% recovery). FIG. 36 (bottom) shows the non-magnified images of the representative well when the assay was performed using liquid reagent and lyophilized reagent. The recovery of hTSH using lyophilized reagents is similar to liquid reagents with the experimental error of the assay indicating the similar performance.

Conclusions: The data demonstrate that lyophilized reagents can be used in the assay for hTSH and perform as well as liquid reagents. The invention can be practiced with lyophilized reagents which extends the usefulness of the invention.

Example 20

Stabilization of Individual Reagents—Lyophilization of Reagents for Detection of S. aureus Together in Layers This example describes the stabilization of reagents for the detection of S. aureus together in layers by lyophilization. The methods described in this example are generally applicable to the reagents used in other embodiments of the invention.

Stabilization of assay reagents extends the shelf-life and performance of the assay reagents described in this invention.

Long-term storage of dried reagents is of economic value to the users of the reagents and is especially importance when applied to situations in which reagents are not regularly needed but for which a sudden need arises such as a bioterrorist incident or epidemic disease outbreaks.

Lyophilized reagents are also of use in the manufacture of unitized reagents such as single-use cartridges.

The method described can be used with reagents manufactured to detect and enumerate individual cellular and molecular targets at low concentrations in clinical, industrial, and environmental samples.

Method. This example shows another method for stabilizing reagents by lyophilizing reagents in layers together (FIG. 37). In this example, reagents for the detection of S. aureus bacterial cells are lyophilized in layers. A Dura-Stop lyophilizer was pre-cooled to −45° C. An aliquot (65 µL) of dyed-cushion reagent (10% v/v Optiprep® (Sigma-Aldrich D1556) containing 2 mg/mL Chromotrope R2 (Sigma-Aldrich Catalog No. C3143) and 5% w/v trehalose (Sigma-Aldrich, Catalog No. T9449)) was pipetted into assay wells. The plate was placed in the lyophilizer and the reagent layer allowed to freeze for 1 hour. The assay wells were then removed from the lyophilizer and 25 µL of a complete reagent mix (containing SYBR® Green 1 (Invitrogen Catalog No. S-7563) diluted 1 part in 2000 parts with 0.9% sodium chloride, 0.005% w/v chicken anti-S. aureus Protein A magnetic particles (manufactured as described in example 4) in TBS-TBP, pH 7.4) was carefully overlaid on the top of the frozen dye cushion layer. The assay wells were then immediately returned to the lyophilizer and frozen for 1 hour. The vacuum was applied and the wells were lyophilized at −45° C. for 16 hours. Then the temperature was set to −5° C. for 6 hrs, followed by 25° C. for 2 hrs. Upon completion, the lyophilizer was turned off and the vacuum was released. The wells were removed and covered with PCR film and stored in desiccator until further use.

The performance of lyophilized reagents was determined by comparing the S. aureus assay performed using fresh liquid reagent and lyophilized reagent. A culture of S. aureus (ATCC strain 29213) was grown in growth media TSB (Tryptic Soy Broth, Acumedia cat#7164A) at 35° C. for 2 hours to achieve log-phase growth ($OD_{600}$=0.3). The S. aureus cells were counted in a Petroff-Hausser counting chamber on Zeiss microscope and cells were diluted to $2\times10^5$ cells/mL in fresh TSB. The reaction was carried out in 96 well polycarbonate PCR plate (Fisher Scientific, Cat. No. 14230237). The reaction mixture (50 µL) contained 25 µL S. aureus cells (5,000 cells) in PBS-TBP (or no cell as negative control), 20 µL of SYBR® Green 1 dye (diluted 1:2000× in 0.9% sodium chloride) and 5 µL of chicken anti-protein A antibody coated magnetic particles ($2\times10^{10}$ particles/mL) suspended into PBS-TBP, pH 7.4. Assay reaction was mixed well by pipetting and incubated for 15 min at ambient temperature in dark. After incubation, 40 µL of reaction mixture was overlaid on 70 µL of cushion solution (consisted of 15% OptiPrep® (Sigma Catalog No. D1556) containing 5 mg/mL Chromotrope 2R (Sigma-Aldrich C3143)) pre-aliquoted in 96-well half-area diameter clear bottom black plate (Grainer, Cat. No. 675096). For dry reagent assay, S. aureus cells (5,000 cells) in 120 µL of PBS-TBP (or no cells as negative control) was added on top of specific wells with lyophilized reagents and the wells were incubated for 15 min in dark at ambient temperature. In order to select cell-particles complexes at the bottom of the well, the plate was then subjected to magnetics by placing it on magnet for 4 min. The plate was then removed from the magnet and was placed in a high throughput automated imaging analyzer. The wells were then imaged on the analyzer described above at a 0.1 sec exposure time. Individual fluorescent cells were then enumerated using software.

Results. FIG. 38 (top) shows a bar graph indicating the S. aureus counts in the lyophilized reagent wells compared to the liquid reagent wells. FIG. 38 (bottom) shows the non-magnified images of the representative wells (with and without S. aureus cells) when the assay was performed using lyophilized reagent. The S. aureus counts using lyophilized reagents are similar to liquid reagents with the experimental error of the assay indicating the similar performance.

Conclusions. The results demonstrate that reagents lyophilized together in layers can perform as well as liquid reagents. The invention can be practiced with lyophilized reagents which extends the usefulness of the invention.

Alternative embodiments. Lyophilization conditions, such as temperatures and times can be adjusted, and various reagents in addition to those listed above can undergo similar treatments. Reagents can alternatively be dried by evaporation (Examples 19 and 20) or by vapor deposition. For example, reagents mixed as above, can be placed in an oven at elevated temperature or left at or below room temperature where moisture can be allowed to escape in vapor form due to differences in relative humidity. Alternatively, the reagents can be placed in a desiccating chamber to remove moisture from reagents. A combination of liquids and solids can be used.

Example 21

Specific Detection of Biotin by the Combination of Imaging and Movement of the Selected Target Signaling Moiety Complexes Examples 8-17 above describe methods to image and assay targets specifically and at low concentrations or low numbers of targets through the use of signaling moieties, selection moieties, and dye-cushion reagent to reduce "background" signal from free signaling complexes and unselected signaling complexes bound to non-targets.

These methods can be performed in one vessel without a washing step. This example describes a method to further reduce background after a selection step. In this example, the magnetic selection moiety is moved in a direction parallel to the direction of the imaging surface and sequentially imaged. Only true signaling moiety-target-selection moiety complexes will move with changes in position of the selection force. Through use of an image taken with a longer exposure or through a sequence of images the movement of true signaling moiety-target-selection moiety complexes can be seen as a streak or 'comet'. Free signaling moieties and non-selected non-target signaling moiety target complexes that are in the imaging region will move randomly or not at all. Only those objects that display the correct response to the movement are counted as true signal objects by the image analysis software.

The method described can be used with reagents manufactured to detect and enumerate individual cellular and molecular targets at low concentrations in clinical, industrial, and environmental samples.

Method: Streptavidin magnetic particles were manufactured using the method described in example 4 with the following modifications: Streptavidin (Thermo Pierce catalog No. 21122) was conjugated instead of antibody, and carboxylated 400 nm magnetic particles were used (Merck EMD, Catalog No. M1030/40/7283). Fluorescent biotin coated (1 µM) particles were mixed at an several multiples of ratios to the Streptavidin magnetic particles in a solution of PBS-TBP, pH 7.4 and incubated for 15 min. The complexes were washed with PBS-TBP and diluted to final concentration of 400,000 Fluor complexes per mL. This solution was then mixed with a solution of 40 mg/mL Chromotrope 2R (Sigma-Aldrich, Catalog No. C3143) and loaded on a Kova plastic slide. The slide was imaged on a Zeiss inverted microscope with the green fluorescent filter. A Neodynium magnet was moved under the slide and an image recorded at a long exposure.

Result. The image of the selected complexes moving (i.e., 'comets') is shown in FIG. 39. It demonstrates the movement of the selected signaling-target-selection moiety complexes versus the non-movement of non-selected background fluorescence.

Conclusions. The image demonstrates the ability of the method described to distinguish selected signaling-target-selection moiety complexes from non-selected background fluorescent objects that increasing the assay specificity. This embodiment of the invention can improve the specificity of enumerating targets with non-magnified imaging without washing.

Alternative embodiments. Other embodiments the movement of the selection force could be in more than one direction in a two dimensional plane parallel to the imaging surface.

In other embodiments different signal characters can be used e.g. fluorescence, chemiluminescence, light absorbing, light scattering, phosphorescence, enzymatic reactivity and Raman scattering.

Other embodiments could use different signaling moieties (with different signaling character) e.g., fluorescein diacetate (fluorescent esterase substrate), SYBR® Green (fluorescent DNA stain), Sudan black (lipid staining), enzyme substrates that yield insoluble products, polystyrene particles, polystyrene particles containing fluorescent dyes, colloidal gold and others.

In these other embodiments other dyes can be used to match the different signaling character and moieties in use.

Different category labeling moieties can be used include but are not limited to: Antibodies (including various immunoglobulin types) and other proteins (e.g. lectins, hormone receptors and others), oligonucleotides and their synthetic analogs (e.g. peptide nucleic acids, aptamers and others), oligosaccharides (e.g. heparin and others), organic polymers (e.g. dextran sulfate and others) and small molecules (e.g. drugs, non-peptide hormones, biotin, dyes and others)

The selection may be specific through selection of a specific target within a category (e.g. selection of hTSH from blood or S. aureus cells from nasal samples). The assay may be also specific through selection of a labeled category of targets (e.g. Selection of Lipoproteins from Human plasma).

The method described can be used in the selection of targets which can include, but are not limited to: Cells, viruses, organelles, lipoproteins, and molecules including proteins, oligonucleotides, lipids, oligosaccharides, and small organic and inorganic molecules.

The method is applicable to samples with complex matrices including whole blood, plasma, feces, wastewater, milk, and others.

Samples can also be processed prior to selection e.g. Cells can be fixed with methanol. DNA can be extracted and purified. Hormones, proteins and vitamins normally found bound to serum factors can be released, and through other processes. Samples can also be selected after labeling, e.g. targets can be pre-labeled with signaling moiety complexes before selection.

Example 22

Use of Photobleaching with SYBR® Green Labeling and Chicken Anti-S. aureus Protein A for Specific Detection of S. aureus Bacterial Cells Detection of targets at low concentrations or numbers requires specific detection of signaling moiety-target-selection moiety complexes. This example describes a method to use photobleaching of SYBR® Green and chicken anti-S. aureus protein A labeled S. aureus bacterial cells to enhance the specific detection of S. aureus cells The method utilizes the relative stability of fluorescence signal from fluorescent particles to that of fluorogenic DNA staining to photobleaching.

An outline of the method is shown in the diagram in FIG. 40. Targets are labeled with two different signaling moieties (these differ in their sensitivity to photobleaching) and a magnetic selection moiety. The complexes are magnetically selected and imaged. The samples are exposed to light for sufficient time for one of the signaling moieties to be photobleached. A second image is taken. The instrument software then performs an image analysis, in which only signaling moieties that were in pixels adjacent to pixels where signals were photobleached are counted as signaling events.

The method described can be used with the other embodiments of the invention described in the examples above to detect and enumerate individual cellular and molecular targets at low concentrations in clinical, industrial, and environmental samples.

Method. A culture of S. aureus (ATCC strain 29213) is grown in TSB growth media (Tryptic Soy Broth, Acumedia cat#7164A) at 35° C. for 2 hours to achieve log-phase growth ($OD_{600}$=0.3). The reaction is carried out in 96 well polycarbonate PCR plate (Fisher Scientific, Cat. No. 14230237). A reaction mixture (50 µL) containing 25 µL S. aureus cells (5,000 cells) in PBS-TBP or just PBS-TBP (no cells), 20 µL of SYBR® Green 1 dye (diluted 12000× in saline) mixed 0.005% w/v chicken anti-S. aureus protein A fluorescent particles (described in example 3) and 5 µL of 0.005% w/v chicken anti-S. aureus Protein A magnetic particles (manufactured as described in example 4) suspended into PBS-TBP solution. The assay reaction is mixed well by pipetting and incubated for 15 min at ambient temperature in dark. After incubation, 40 µL of reaction mixture is overlaid on 70 µL of cushion solution (consisted of 15% OptiPrep® Sigma Cat. No. D1556) and 5 mg/mL Chromotrope 2R (Sigma-Aldrich C3143) pre-aliquoted in 96-well half-area diameter clear bottom black plate (Grainer, Cat. No. 675096). In order to select cell-particles complexes at the bottom of the well, the plate is subjected to magnetics by placing it on magnet for 4 min. The plate is removed from the magnet and is placed in a high throughput automated imaging analyzer. The wells are imaged, photobleached, and imaged again on the analyzer. The first image is taken with 0.1 sec exposure time; the plate is illuminated twice for 1 sec each to photobleach the SYBR® Green, then imaged again with a 0.1 sec exposure time. Image analysis software enumerates signal moieties that were adjacent to signal moieties that were photobleached. In this example this would include only those chicken anti-S. aureus Protein A fluorescent particles that were adjacent to SYBR® Green labeled S. aureus cells.

Conclusions: This example demonstrates the detection of specific signal in the assay through the combination of photobleaching with image analysis. The use of photobleaching in the invention with non-magnified imaging of targets without washing reduces interference from interfering materials in the assay and to produce a specific result.

Alternative embodiments. The method of this example can be applied with any pair of fluorescent labels which differ in their susceptibility to photobleaching. The specific label can represent either the photobleaching resistant or susceptible moiety in the pair of signaling moieties.

Different category labeling moieties can be used include but are not limited to: Antibodies (including various immunoglobulin types) and other proteins (e.g. lectins, hormone receptors and others), Oligonucleotides and their synthetic analogs (e.g. peptide nucleic acids, aptamers and others), Oligosaccharides (e.g. heparin and others), Organic polymers (e.g. dextran sulfate and others) and Small molecules (e.g. drugs, non-peptide hormones, biotin, dyes and others)

Example 23

Use of Photobleaching with SYBR® Green Labeling for Specific Detection of S. aureus Bacterial Cells Detection of targets at low concentrations or numbers requires specific detection of signaling moiety-target-selection moiety complexes. This example describes a method to use photobleaching of SYBR® Green labeled *S. aureus* bacterial cells to enhance the specific detection of true signaling moiety-target-selection moiety complexes against non-specific background.

The method utilized the susceptibility of some labeling methods to photobleaching. Fluorescence detection by counting fluorescent signaling moieties imaged with non-magnified imaging can have background due to fluorescent debris. This method allows detection of fluorescent debris by using photobleaching of the specific signal to identify non-specific fluorescent signal.

An outline of the method is shown in the diagram in FIG. 41. Targets were labeled with signaling moieties and a magnetic selection moiety. The complexes were magnetically selected and imaged. Then the sample was exposed to light for sufficient time to for the signaling moieties to be photobleached. A second image was taken. The instrument software then performs an image analysis in the second image is subtracted from the first image. The remaining signaling moieties (which were photobleached) are then enumerated as specific signal.

The method described can be used with the other embodiments of the invention described in the examples above to detect and enumerate individual cellular and molecular targets at low concentrations in clinical, industrial, and environmental samples.

Method. A culture of *S. aureus* (ATCC strain 29213) was grown in TSB growth media (Tryptic Soy Broth, Acumedia cat#7164A) at 32.5° C. for 2 hours to achieve log-phase growth ($OD_{600}$=0.3). The reaction was carried out in 96 well polycarbonate PCR plate (Fisher Scientific, Cat. No. 14230237). A reaction mixture (50 µL) containing 25 µL *S. aureus* cells (5,000 cells) in PBS-TBP or just PBS-TBP (no cells), 20 µL of SYBR®Green 1 dye (diluted 1:2000× in saline) was mixed and 5 µL of 0.005% w/v chicken anti-*S. aureus* Protein A magnetic particles (manufactured as described in example 4) were suspended into PBS-TBP solution. The assay reaction was mixed well by pipetting and incubated for 15 min at ambient temperature in dark. After incubation, 40 µL of reaction mixture was overlaid on 70 µL of cushion solution (consisted of 15% OptiPrep® Sigma Cat. No. D1556) and 5 mg/mL Chromotrope 2R (Sigma-Aldrich C3143)) pre-aliquoted in 96-well half-area diameter clear bottom black plate (Grainer, Cat. No. 675096). In order to select cell-particles complexes at the bottom of the well, the plate was subjected to magnetic selection by placing it on magnet. The plate was removed from the magnet and was placed in a high throughput automated imaging analyzer that used non-magnified imaging. The wells were then imaged with a 0.1 sec exposure, photobleached by illuminating the plate twice for 1 sec and then imaging again for 0.1 sec analyzer. Image analysis software then subtracted the second image from the first image. The remaining signal moieties were enumerated as *S. aureus* bacterial cells.

Results: The images in FIG. 41 demonstrate the method. The first image is the initial image, the second image is the image after photobleaching and the final image is a software generated image of image 2 subtracted from image 1 and shows the photobleached specifically labeled SYBR® Green labeled *S. aureus*. The images show that the large piece of fluorescent debris was subtracted from the data.

Conclusions: This example demonstrates the removal of non-specific signal in the assay through the combination of photobleaching with image analysis. The use of photobleaching in the invention with non-magnified imaging of targets without washing reduces interference from interfering materials in the assay and to produce a specific result.

Alternative embodiments. Other embodiments of this example include a different sequence of events. The assay well with reagents is first photobleached before the selection step, followed by selection and non-magnified imaging. This embodiment can be used in cases where the interfering materials can be photobleached.

Example 24

Automated Imaging Analyzer for Detecting Targets

Overview. This example demonstrates automatic performance of the invention in an automated analyzer (FIG. 43, 44). The analyzer accepts a cartridge containing imaging wells (FIG. 42), uses magnetic selection to deposit complexes of labeled targets selection moieties onto the detection surface of the imaging well. The analyzer incorporates a CMOS camera for imaging individual labeled target complexes and has software and hardware for sample container conveyance, incubation, focusing, image analysis, and results reporting. The analyzer has a throughput of up to 40 samples per hour, which is useful in high volume clinical laboratory testing applications. It could also be used in food processing and veterinary testing applications.

Description. The analyzer has two queues to accept stacks of sample containers (FIGS. 43, 44). The queue is designed to accept a stack between one and eight sample containers. When a stack is placed in either input queue opening, a photoelectric sensor (Omron photoelectric retro-reflective sensor E3T-SR21) is triggered and signaled the control software to activate a stepper motor (Arcus DMAX-KDRV-23) to move the stack into the analyzer for processing.

When a stack is ready to be processed in either queue, the analyzer processes the top sample container in the stack first. The top of the stack is found with a photoelectric sensor (Omron photoelectric retro-reflective sensor E3T-SR21) mounted to the gantry robot (FIG. 44). The robot scans each queue with the sensor starting at the maximum stack height and moved down until a sample container triggers the sensor. Once found, the gantry robot removes the top sample container.

Movement of the sample container in the system is accomplished by three motor systems (FIGS. 43, 44). These systems are called the input system, the main gantry system, and the imager gantry system. Each system is described in detail below. The systems are capable of operating independently, and occasionally required synchronization for specific operations.

The input system consists of a single conveyor belt powered by a stepper motor (Arcus DMAX-KDRV-23) as mentioned above (FIGS. 43, 44). The belt moves the sample container from the initial entry point to the space designated for gantry robot pickup. When a previous sample container is already in the pickup position, a new sample container moved with the belt until it contacted the sample container ahead of it. At that point, the belt slid under the sample containers that were queued for the pickup position.

Three stepper motors (Arcus DMAX-KDRV-17) were present in the gantry system (FIG. 44). Each motor is connected to linear stage (Automation Solutions, DL20DW-XZ) of a different length. The longest stage controlled the gantry Y (left and right) directions. This stage is anchored to the base plate. Attached to Y stage platform is the shortest stage which controlled the gantry X (forward and backward) directions. Attached to the X stage platform is the stage used to control the gantry Z (top and bottom) directions. Attached to the Z stage is a pair of forks. The forks have features that allowed alignment with features molded in the sample container (FIG. 42). Also attached to the Z stage platform is a photoelectric sensor (Omron photoelectric retro-reflective sensor E3T-SR21). The sensor is used to measure the stack height, as described above.

The gantry picks up the sample container using the forks by adjusting the X and Z stages. Once the sample container is held by the forks, the X stage moves backwards to give clearance to the Y stage. In this position, the Y stage can move the sample container to any station for processing without colliding with structures in the analyzer.

The imager gantry system consists of two stepper motors (Arcus DMAX-KDRV-17) attached to two linear stages (Automation Solutions, DL20DW-XZ). The longer stage is called the imager X stage. This stage controlled the forward and backward motions of the imager gantry. Attached to the imager X stage is the imager Z stage, which controlled the imager gantry's vertical motion. Attached to the Z stage is a platform that had alignment features on its surface that coincided with similar alignment features on the sample container (FIGS. 43, 44).

The imager Z stage differed from the other stages by having a fine pitched screw mechanism. It has a resolution of 5 microns, as opposed to the 50 micron resolution of the other stages on the analyzer. This difference permits fine focus adjustments as well as fine control of height for initiating the reaction assay. These features are discussed in detail below.

After the sample container is picked up from the input position by the main gantry robot, it is taken to a barcode reader (Microscan MS1). The 1D barcode on the sample container encoded information including lot number, test type, and test parameters. When read, the control program stored the information in a data structure for tracking the sample container and holding the analysis results.

Two types of incubation occur in this analyzer. They are fixed temperature incubation for sample growth and ambient temperature incubation for the assay reaction. After the sample container barcode is scanned, the initiation of the sample into the growth wells occurs. The main gantry robot moves the sample container to the imager gantry platform (FIG. 44). After the gantry placed the sample container onto the platform, the imager gantry raises the imaging platform until the plunger cap on the sample container (FIG. 42) is pressed by a feature at the top of the imager Z stage. By depressing the plunger, the liquid sample is mobilized from the sample input reservoir to the growth chambers were growth reagents were lyophilized. Next, the sample container is placed in the on-board fixed temperature incubator by the main gantry robot (FIGS. 43, 44). The sample containers can be at incubated at 35° C. for four hours to allow bacterial cell growth.

The incubator consists of a shelf constructed of machined parts (top, bottom, left, right, back, and front sides). The shelf bottom contains features that mated with the feature on the bottom of the sample container (FIGS. 43, 44). The incubator walls are constructed using insulation foam which divided the incubator into four chambers. The rear wall of the incubator is shaped to fit four machined doors in front of the four chambers. The doors are opened and closed using actuators (Firgelli L12-50-100-12-I). Heating of the incubator used heating strips (OMEGA, SRFG-310/10-P) across the outside top and bottom of the incubator. Heating strips, as well as any exposed outside surface, were covered in insulation foam with the exception of the doors.

Initiation of the assay occurs after growth incubation is completed. The main gantry robot removed the sample container from the growth incubator and moves it to the imager gantry platform (FIG. 44). After the gantry places the sample container onto the platform, the imager gantry initiates the assay by raising the platform until the plunger cap on the sample container (FIG. 42, 44) is completely pressed in by a feature at the top of the imager Z stage. By pressing down on the plunger a second time, the liquid sample is forced to move from the growth chambers into the imaging chambers where the assay reagents were lyophilized. As soon as the liquid entered the imaging chamber, the reagents are rehydrated and the assay reaction begins. The imager gantry returns to the pickup position and the main gantry robot moved the sample container to the reaction incubation station. This incubation lasts fifteen minutes and occurs at room temperature.

The reaction incubator consists of a system of fifteen shelves. The individual shelves have a feature that mates with the feature on the bottom of the sample container for positioning alignment.

After the reaction is complete, selection of the targets occurs by magnetic selection. The main gantry robot moves the sample container from the shelf to the magnet station (FIGS. 43, 44, 46). Magnetic selection is performed for five minutes before the main gantry moves the sample container to the imaging platform. As shown in FIG. 44, the magnetic capture station consisted of two identical magnet assemblies. The assemblies contained rare earth, solid state type magnets (neodymium-iron-boron N48 NdFeB, 22×22×100 mm bars) as shown on the FIG. 46. This allows for magnetic selection to occur for two sample containers during overlapping time periods.

After magnetic selection, imaging is performed. The imaging subsystem (FIG. 45) is designed to work with fluorescent signaling moieties. The signaling moieties are excited with blue light filtered through a band pass filter centered around a 475 nanometer wavelength. Emission light is collected after filtering the light through a band pass filter centered at about 535 nanometers in wavelength. The illumination components, detection optics, and camera are all positioned under the sample container in the imaging assembly (FIG. 44).

After magnetic capture is complete, the main gantry robot moves the sample container from the magnet station to the imager gantry robot (FIG. 44). The imager gantry robot moved the sample container over a distance sensor (Keyence LK-G37). The distance to each imaging well is measured and the focus distance is calculated. The imager gantry robot is positioned above the CMOS camera (Mightex BCN-B013) which acquires an 8 bit grayscale image of each well. Each well is imaged ten times and summed to result in a higher bit grayscale image for analysis.

Image analysis occurs using onboard software. Once the analysis is completed, the imager gantry robot moves the sample container to the ejection system. The sample container is then pushed off the platform and into the biohazard waste container (FIG. 43). Once the data is analyzed, the results, along with the cartridge information, are stored on a computer, printed (Seiko, DPU-30) and displayed on the LCD touchscreen monitor (AEI, ALCDP7WVGATS) (FIG. 43).

The system is designed to be controlled by a single small board computer (Ampro, RB800R) running Ubuntu Linux 2.6. All components are connected to the computer either directly or through controller boards. Components connected directly to the computer include the motor controller (Galil, DMC-2183-DC24-DIN), LCD monitor (AEI, ALCDP7WVGATS), CMOS camera (Mightex, BCN-B013), distance sensor (Keyence LK-G37), and printer (Seiko, DPU-30). The components connected through the motor controller include photoelectric sensors (Omron, E3T-SL22), stepper motors for the main gantry and imager gantry (Arcus, DMAX-KDRV-17), stepper motor for the input bay conveyor (Arcus DMAX-KDRV-23), and LEDs (Lumileds, LXHL-PB09).

Results. FIG. 47 shows detection of individual labeled *S. aureus* cells in the cartridge shown in FIG. 42 using the method of Example 16 and the automated imaging analyzer of this example (FIGS. 43, 44).

Conclusion. This analyzer can automatically process sample containers with minimal user interaction. The sample container interacts with an analyzer that supports on demand processing, sample growth, non-magnified imaging and integrated waste disposal. The analyzer allows for detection of individual targets that have been bound to signaling and selection moieties using a CMOS camera without magnification.

The invention claimed is:

1. A method for determining whether one or more targets is present in a sample, said method comprising:
   a) providing a vessel comprising a detection surface with a detection area having a shortest linear dimension of ≥1 mm;
   b) combining the sample with signaling moieties, selection moieties, and optionally a crosslinker, wherein either
      (i) signaling moieties and selection moieties bind to one or more targets when present in the sample to form complexes of said one or more targets, said signaling moieties, and said selection moieties; or
      (ii) signaling moieties and selection moieties bind to each other, and one or more targets when present in the sample compete with said binding thereby reducing the formation of complexes of said signaling moieties and said selection moieties; or
      (iii) signaling moieties and selection moieties bind to the crosslinker, and one or more targets when present in the sample compete with said binding thereby reducing the formation of complexes of said signaling moieties, said selection moieties, and said crosslinker;
   c) providing any complexes of (b)(i)-(b)(iii) in a liquid overlying layer that overlays an underlying cushion layer adjacent to the detection surface of the vessel, wherein the underlying cushion layer is denser than the overlying liquid layer and separates the overlying liquid layer from the detection surface and wherein said underlying cushion layer comprises a dye that interferes with the transmission of light to or from the signaling moieties;
   d) applying a selection force to move said selection moieties, either unbound or in a complexes of (b)(i), (b)(ii), or (b)(iii), in said overlying layer through said underlying cushion layer to deposit said selection moieties within a detection zone corresponding to said detection area, wherein the selection force does not move said one or more targets not bound to selection moieties into the detection zone; and
   e) simultaneously detecting individual complexes of (b)(i), (b)(ii), or (b)(iii) within the detection zone, at magnification of less than 5×, to determine whether said one or more targets is present in said sample, wherein said method does not comprise a washing step and wherein said targets measure less than 50 microns in at least two orthogonal dimensions, and wherein, for (b)(ii) and (b)(iii), the determining whether said one or more targets is present in said sample is made relative to a reference.

2. The method of claim 1, wherein said signaling moieties comprise photonic signaling character.

3. The method of claim 1, wherein said signaling moieties or selection moieties are conjugated to a category-binding molecule.

4. The method of claim 3, wherein said category-binding molecule is an antibody, an antigen, a lectin, a carbohydrate, a protein, a nucleic acid molecule, a ligand, a receptor, or a small molecule.

5. The method of claim 1, wherein said signaling moieties specifically bind to said targets.

6. The method of claim 1, wherein said targets are cells, viruses, or molecules.

7. The method of claim 6, wherein said cells are bacterial cells.

8. The method of claim 1, wherein said bacterial cells are *Staphylococcus aureus* cells, *E. coli* cells, or *Bacillus anthracis* cells.

9. The method of claim 6, further comprising contacting said cells with a second signaling moiety that specifically binds to an internal component of said cell.

10. The method of claim 9, wherein said internal component is a nucleic acid molecule or a lipid.

11. The method of claim 9, further comprising, after step (d), photobleaching said second signaling moiety and detecting said signaling moiety from step (b) within said overlying layer or said underlying cushion layer.

12. The method of claim 1, wherein said targets are molecules secreted by microbial cells.

13. The method of claim 1, wherein said signaling moieties are fluorescent particles.

14. The method of claim 1, wherein said signaling moieties comprise a DNA stain.

15. The method of claim 1, wherein, prior to step (b), said sample is combined with microbiological growth medium followed by incubation for more than 1 hour.

16. The method of claim 15, wherein said microbiological growth medium comprises an antibiotic or microbial growth inhibitor.

17. The method of claim 1, wherein said signaling moieties or said selection moieties are in dried form in said vessel in step (a).

18. The method of claim 1, wherein said underlying cushion layer is in dried form in said vessel in step (a).

19. The method of claim 18, wherein in step (c) a composition comprising said targets hydrates said underlying cushion.

20. The method of claim 19, wherein in step (c) a composition comprising said targets hydrates said overlying layer and said underlying cushion layer.

21. The method of claim 1, wherein said overlying layer further comprises a dye that interferes with the transmission of light to or from the signaling moieties.

22. The method of claim 1, wherein said targets are selected from human thyroid stimulating hormone, *C. albicans* or an antigen of *Bacillus anthracis*.

23. The method of claim 22, wherein said antigen is selected from lethal factor (LF), protective antigen (PA), and poly-D-γ-glutamic acid (PDGA) capsule polypeptide.

24. The method of claim 1, wherein said targets are methicillin-resistant *S. aureus* (MRSA) cells.

25. The method of claim 1, wherein said targets are present in, or obtained from, a biological sample.

26. The method of claim 25, wherein said biological sample is human whole blood, serum, plasma, mucus, urine, bile, synovial joint fluid, spinal fluid, amniotic fluid, sweat, nasal or respiratory fluid, vaginal secretions, ejaculate, wound exudates, sputum or bronchoalveloar lavage fluids, feces, bone, hair, dried cells, skin samples, fresh, frozen, or fixed pathology samples, or swabs taken from nasal, nasopharyngeal, throat, axillar, perineal, or rectal sites.

27. The method of claim 1, wherein said selection force is gravity, magnetism, electrical potential, centrifugal force, centripetal force, buoyant density, or pressure.

28. The method of claim 1, wherein said signaling moieties comprise fluorophores, chemiluminescent agents, bioluminescent agents, resonance light scattering particles, light absorption or chromogenic signaling agents, quantum dots, or up-converting phosphors.

29. The method of claim 1, wherein said selection moieties comprise magnetic particles, silica particles, or ferritin.

30. The method of claim 1, wherein the complexes are those of step (b)(ii) or (b)(iii); and the detection of said target occurs by a reduction in the number of complexes of (b)(ii) or (b)(iii) formed in the presence of the target compared to the number of complexes formed in the absence of the target.

31. The method of claim 1, wherein said vessel is an imaging well having an imaging depth of greater than 2 mm.

32. The method of claim 1, wherein the targets are cells, and step (e) determines the differential growth of said cells in the presence and absence of a growth inhibitor.

33. The method of claim 1, wherein said complexes are those of (b)(i).

* * * * *

UNITED STATES PATENT AND TRADEMARK OFFICE
CERTIFICATE OF CORRECTION

PATENT NO.         : 9,643,180 B2
APPLICATION NO.    : 13/120516
DATED              : May 9, 2017
INVENTOR(S)        : Ezra Abrams et al.

It is certified that error appears in the above-identified patent and that said Letters Patent is hereby corrected as shown below:

In the Claims

Column 67, Line 56, replace "in a complexes" with --in complexes--.

Signed and Sealed this
Fourteenth Day of August, 2018

Andrei Iancu
*Director of the United States Patent and Trademark Office*

UNITED STATES PATENT AND TRADEMARK OFFICE
CERTIFICATE OF CORRECTION

PATENT NO. : 9,643,180 B2
APPLICATION NO. : 13/120516
DATED : May 9, 2017
INVENTOR(S) : Ezra Abrams et al.

Page 1 of 1

It is certified that error appears in the above-identified patent and that said Letters Patent is hereby corrected as shown below:

In the Specification

Column 1, Line 2, add "Government Support" after the Title and before the "CROSS-REFERENCE TO RELATED APPLICATIONS" as follows:
Government Support
This invention was made with government support under grant numbers AI055195, AI080016, and AI078695 awarded by the National Institutes of Health. The government has certain rights in the invention.

Signed and Sealed this
Seventh Day of September, 2021

Drew Hirshfeld
*Performing the Functions and Duties of the*
*Under Secretary of Commerce for Intellectual Property and*
*Director of the United States Patent and Trademark Office*